US011158149B2

(12) United States Patent
Robertson et al.

(10) Patent No.: US 11,158,149 B2
(45) Date of Patent: Oct. 26, 2021

(54) PERSONAL AUTHENTICATION APPARATUS SYSTEM AND METHOD

(71) Applicant: OTSUKA PHARMACEUTICAL CO., LTD., Tokyo (JP)

(72) Inventors: Timothy Robertson, Belmont, CA (US); George Savage, Portola Valley, CA (US); Benedict Costello, Berkeley, CA (US); David O'Reilly, Palo Alto, CA (US)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 15/592,423

(22) Filed: May 11, 2017

(65) Prior Publication Data

US 2018/0096547 A1  Apr. 5, 2018

Related U.S. Application Data

(63) Continuation of application No. 13/843,307, filed on Mar. 15, 2013, now Pat. No. 9,659,423.

(51) Int. Cl.
*A61B 5/00* (2006.01)
*G07C 9/37* (2020.01)
(Continued)

(52) U.S. Cl.
CPC .............. *G07C 9/37* (2020.01); *A61B 5/0006* (2013.01); *A61B 5/0028* (2013.01); *A61B 5/053* (2013.01);
(Continued)

(58) Field of Classification Search
CPC ....... A61B 5/00; A61B 5/0002; A61B 5/0004; A61B 5/0015; A61B 5/0026;
(Continued)

(56) References Cited

U.S. PATENT DOCUMENTS 2,206,695 A * 7/1940 Guanella ................. H03J 7/042
455/263
2,463,504 A * 3/1949 Atkins ..................... H04K 1/02
380/38
(Continued)

FOREIGN PATENT DOCUMENTS

CN   1588649   3/2005
CN   1991868   7/2007
(Continued)

OTHER PUBLICATIONS

AADE, "AADE 37th Annual Meeting San Antonio Aug. 4-7, 2010" American Association of Diabetes Educators (2010); http://www.diabeteseducator.org/annualmeeting/2010/index.html; 2 pp.
(Continued)

*Primary Examiner* — Richard A McCoy
(74) *Attorney, Agent, or Firm* — Mannava & Kang, P.C.

(57) ABSTRACT

A target authentication device includes an electrode to detect an electrical signal associated with a user of the device. The electrical signal represents an authentication code for the device. An authentication receiver module is coupled to the electrode. The module receives the electrical signal from the electrode and determines whether the electrical signal matches a predetermined criterion to authenticate the identity of the user based on the electrical signal. An authentication module is also disclosed. The authentication module includes one electrode to couple an electrical signal associated with a user to a user of a target authentication device, the electrical signal represents an authentication code for the device. An authentication transmission module is coupled to the electrode. The authentication transmission module transmits the electrical signal from the electrode. A method of authenticating the identity of a user of a target authentication device also is disclosed.

17 Claims, 17 Drawing Sheets

(51) Int. Cl.
*G06F 21/34* (2013.01)
*A61B 5/332* (2021.01)
*A61B 5/053* (2021.01)
*A61B 5/117* (2016.01)
*G06K 9/00* (2006.01)
*H04B 13/00* (2006.01)
*A61B 5/30* (2021.01)
*A61B 5/282* (2021.01)
*A61B 5/0205* (2006.01)
*A61B 5/11* (2006.01)
*A61B 5/145* (2006.01)

(52) U.S. Cl.
CPC ............ *A61B 5/117* (2013.01); *A61B 5/332* (2021.01); *A61B 5/6898* (2013.01); *G06F 21/34* (2013.01); *G06K 9/00885* (2013.01); *H04B 13/005* (2013.01); *A61B 5/02055* (2013.01); *A61B 5/11* (2013.01); *A61B 5/1112* (2013.01); *A61B 5/145* (2013.01); *A61B 5/14532* (2013.01); *A61B 5/282* (2021.01); *A61B 5/30* (2021.01); *A61B 2560/0209* (2013.01); *A61B 2560/0412* (2013.01); *A61B 2560/0468* (2013.01); *A61B 2562/0219* (2013.01); *G06K 2009/00939* (2013.01)

(58) Field of Classification Search
CPC ... A61B 5/0031; A61B 5/0073; A61B 5/6861; A61B 5/6802; A61B 5/6846; A61B 5/117; A61B 5/6801; A61B 5/6887; A61B 5/68; A61B 5/72; A61B 5/02; A61B 5/02438; A61B 5/332; A61B 5/0006; A61B 5/0028; A61B 5/053; A61B 5/6898; A61B 5/30; A61B 2560/0209; A61B 2560/0412; A61B 2560/0468; A61B 2562/0219; A61B 5/282; A61B 5/11; A61B 5/1112; A61B 5/145; G07C 9/37; G06F 21/334; G06K 9/00885; G06K 2009/00939; H04B 13/005
See application file for complete search history.

(56) References Cited

U.S. PATENT DOCUMENTS

| | | | |
|---|---|---|---|
| 2,582,968 A * | 1/1952 | Labin | H04K 1/02 380/31 |
| 3,340,866 A | 9/1967 | Noller | |
| 3,607,788 A | 9/1971 | Adolph | |
| 3,642,008 A | 2/1972 | Bolduc | |
| 3,679,480 A | 7/1972 | Brown et al. | |
| 3,682,160 A | 8/1972 | Murata | |
| 3,719,183 A | 3/1973 | Schwartz | |
| 3,828,766 A | 8/1974 | Krasnow | |
| 3,837,339 A | 9/1974 | Aisenberg et al. | |
| 3,989,050 A | 11/1976 | Buchalter | |
| 4,067,014 A | 1/1978 | Wheeler et al. | |
| 4,077,397 A | 3/1978 | Ellis | |
| 4,077,398 A | 3/1978 | Ellis | |
| 4,082,087 A | 4/1978 | Howson | |
| 4,090,752 A | 5/1978 | Long | |
| 4,106,348 A | 8/1978 | Auphan | |
| 4,121,573 A | 10/1978 | Crovella et al. | |
| 4,129,125 A | 12/1978 | Lester | |
| 4,149,168 A | 4/1979 | Hose | |
| 4,166,453 A | 9/1979 | McClelland | |
| 4,185,172 A | 1/1980 | Melindo et al. | |
| 4,239,046 A | 12/1980 | Ong | |
| 4,269,189 A | 5/1981 | Abraham | |
| 4,331,654 A | 5/1982 | Morris | |
| 4,333,150 A | 6/1982 | Matty et al. | |
| 4,345,588 A | 8/1982 | Widder et al. | |
| 4,418,697 A | 12/1983 | Tama | |
| 4,425,117 A | 1/1984 | Hugemann | |
| 4,494,950 A | 1/1985 | Fischell | |
| 4,513,385 A | 4/1985 | Muri | |
| 4,559,950 A | 12/1985 | Vaughan | |
| 4,578,061 A | 3/1986 | Lemelson | |
| 4,635,641 A | 1/1987 | Hoffman | |
| 4,654,165 A | 3/1987 | Eisenber | |
| 4,669,479 A | 6/1987 | Dunseath | |
| 4,688,400 A * | 8/1987 | Chioffe | A44C 7/003 63/12 |
| 4,725,997 A | 2/1988 | Urquhart et al. | |
| 4,749,575 A | 6/1988 | Rotman et al. | |
| 4,763,659 A | 8/1988 | Dunseath | |
| 4,784,162 A | 11/1988 | Ricks | |
| 4,793,825 A | 12/1988 | Benjamin et al. | |
| 4,809,705 A | 3/1989 | Ascher | |
| 4,844,076 A | 7/1989 | Lesho | |
| 4,858,617 A | 8/1989 | Sanders | |
| 4,896,261 A | 1/1990 | Nolan | |
| 4,975,230 A | 12/1990 | Pinkhasov | |
| 4,987,897 A | 1/1991 | Funke | |
| 5,016,634 A | 5/1991 | Vock et al. | |
| 5,079,006 A | 1/1992 | Urquhart | |
| 5,113,859 A | 5/1992 | Funke | |
| 5,167,626 A | 12/1992 | Casper | |
| 5,176,626 A | 1/1993 | Soehendra | |
| 5,232,383 A | 8/1993 | Barnick | |
| 5,245,332 A | 9/1993 | Katzenstein et al. | |
| 5,261,402 A | 11/1993 | DiSabito | |
| 5,263,481 A | 11/1993 | Axelgaard et al. | |
| 5,281,287 A | 1/1994 | Lloyd | |
| 5,283,136 A | 2/1994 | Peled et al. | |
| 5,288,564 A | 2/1994 | Klein | |
| 5,318,557 A | 6/1994 | Gross | |
| 5,394,882 A | 3/1995 | Mawhinney | |
| 5,458,141 A | 10/1995 | Neil et al. | |
| 5,473,612 A | 12/1995 | Dehner, Jr. et al. | |
| 5,485,841 A | 1/1996 | Watkin et al. | |
| 5,511,548 A | 4/1996 | Riazzi et al. | |
| 5,551,020 A | 8/1996 | Flax et al. | |
| 5,596,302 A | 1/1997 | Mastrocola et al. | |
| D377,983 S | 2/1997 | Sabri et al. | |
| 5,623,520 A | 4/1997 | Kaiser | |
| 5,634,466 A | 6/1997 | Gruner | |
| 5,634,468 A | 6/1997 | Platt | |
| 5,645,063 A | 7/1997 | Straka et al. | |
| 5,720,771 A | 2/1998 | Snell | |
| 5,724,432 A | 3/1998 | Bouvet et al. | |
| 5,740,811 A | 4/1998 | Hedberg | |
| 5,792,048 A | 8/1998 | Schaefer | |
| 5,802,467 A | 9/1998 | Salazar | |
| 5,833,716 A | 11/1998 | Bar-Or | |
| 5,845,265 A | 12/1998 | Woolston | |
| 5,862,803 A | 1/1999 | Besson | |
| 5,862,808 A | 1/1999 | Albarello | |
| 5,868,136 A | 2/1999 | Fox | |
| 5,921,925 A | 7/1999 | Cartmell et al. | |
| 5,925,030 A | 7/1999 | Gross et al. | |
| 5,925,066 A | 7/1999 | Kroll et al. | |
| 5,937,059 A | 8/1999 | Kim et al. | |
| 5,957,854 A | 9/1999 | Besson et al. | |
| 5,974,124 A | 10/1999 | Schlueter, Jr. et al. | |
| 5,981,166 A | 11/1999 | Mandecki | |
| 5,999,846 A | 12/1999 | Pardey et al. | |
| 6,023,631 A | 2/2000 | Cartmell et al. | |
| 6,033,370 A | 3/2000 | Reinbold et al. | |
| 6,038,464 A | 3/2000 | Axelgaard et al. | |
| 6,042,710 A | 3/2000 | Dubrow | |
| 6,047,203 A | 4/2000 | Sackner | |
| 6,076,016 A | 6/2000 | Feierbach | |
| 6,081,734 A | 6/2000 | Batz | |
| 6,095,985 A | 8/2000 | Raymond et al. | |
| 6,115,636 A | 9/2000 | Ryan | |
| 6,117,077 A | 9/2000 | Del Mar et al. | |
| 6,122,351 A | 9/2000 | Schlueter, Jr. et al. | |
| 6,141,592 A | 10/2000 | Pauly | |
| 6,151,353 A | 11/2000 | Harrison et al. | |
| 6,200,265 B1 | 3/2001 | Walsh et al. | |

(56) References Cited

U.S. PATENT DOCUMENTS

| | | |
|---|---|---|
| 6,200,625 B1 | 3/2001 | Beckett |
| 6,204,764 B1 | 3/2001 | Maloney |
| 6,206,702 B1 | 3/2001 | Hayden et al. |
| 6,217,744 B1 | 4/2001 | Crosby |
| 6,231,593 B1 | 5/2001 | Meserol |
| 6,238,338 B1 | 5/2001 | DeLuca et al. |
| 6,245,057 B1 | 6/2001 | Sieben et al. |
| 6,275,476 B1 | 8/2001 | Wood |
| 6,285,897 B1 | 9/2001 | Kilcoyne et al. |
| 6,287,252 B1 | 9/2001 | Lugo |
| 6,289,238 B1 | 9/2001 | Besson et al. |
| 6,301,298 B1 | 10/2001 | Kuntz et al. |
| 6,315,719 B1 | 11/2001 | Rode et al. |
| 6,317,714 B1 | 11/2001 | Del Castillo |
| 6,327,486 B1 | 12/2001 | Nissila et al. |
| 6,358,202 B1 | 3/2002 | Arent |
| 6,364,834 B1 | 4/2002 | Reuss |
| 6,366,206 B1 | 4/2002 | Ishikawa et al. |
| 6,371,927 B1 | 4/2002 | Brune |
| 6,374,670 B1 | 4/2002 | Spelman |
| 6,380,858 B1 | 4/2002 | Yarin et al. |
| 6,394,953 B1 | 5/2002 | Devlin et al. |
| 6,394,997 B1 | 5/2002 | Lemelson |
| 6,409,674 B1 | 6/2002 | Brockway et al. |
| 6,426,863 B1 | 7/2002 | Munshi |
| 6,432,292 B1 | 8/2002 | Pinto et al. |
| 6,440,069 B1 | 8/2002 | Raymond et al. |
| 6,441,747 B1 | 8/2002 | Khair |
| 6,477,424 B1 | 11/2002 | Thompson et al. |
| 6,482,156 B2 | 11/2002 | Lliff |
| 6,494,829 B1 | 12/2002 | New et al. |
| 6,496,705 B1 | 12/2002 | Ng et al. |
| 6,526,315 B1 | 2/2003 | Inagawa |
| 6,544,174 B2 | 4/2003 | West |
| 6,564,079 B1 | 5/2003 | Cory |
| 6,577,893 B1 | 6/2003 | Besson et al. |
| 6,579,231 B1 | 6/2003 | Phipps |
| 6,605,038 B1 | 8/2003 | Teller et al. |
| 6,605,046 B1 | 8/2003 | Del Mar |
| 6,609,018 B2 | 8/2003 | Cory |
| 6,612,984 B1 | 9/2003 | Kerr |
| 6,632,175 B1 | 10/2003 | Marshall |
| 6,632,216 B2 | 10/2003 | Houzego et al. |
| 6,643,541 B2 | 11/2003 | Mok et al. |
| 6,654,638 B1 | 11/2003 | Sweeney |
| 6,663,846 B1 | 12/2003 | McCombs |
| 6,673,474 B2 | 1/2004 | Yamamoto |
| 6,680,923 B1 | 1/2004 | Leon |
| 6,689,117 B2 | 2/2004 | Sweeney et al. |
| 6,694,161 B2 | 2/2004 | Mehrotra |
| 6,704,602 B2 | 3/2004 | Berg et al. |
| 6,720,923 B1 | 4/2004 | Hayward et al. |
| 6,738,671 B2 | 5/2004 | Christophersom et al. |
| 6,740,033 B1 | 5/2004 | Olejniczak et al. |
| 6,745,082 B2 | 6/2004 | Axelgaard et al. |
| 6,755,783 B2 | 6/2004 | Cosentino |
| 6,757,523 B2 | 6/2004 | Fry |
| 6,800,060 B2 | 10/2004 | Marshall |
| 6,801,137 B2 | 10/2004 | Eggers et al. |
| 6,807,438 B1 | 10/2004 | Brun Del Re et al. |
| 6,814,706 B2 | 11/2004 | Barton et al. |
| 6,822,554 B2 | 11/2004 | Vrijens et al. |
| 6,836,862 B1 | 12/2004 | Erekson et al. |
| 6,839,659 B2 | 1/2005 | Tarassenko et al. |
| 6,840,904 B2 | 1/2005 | Goldberg |
| 6,842,636 B2 | 1/2005 | Perrault |
| 6,845,272 B1 | 1/2005 | Thomsen |
| 6,856,832 B1 | 2/2005 | Matsumura et al. |
| 6,864,780 B2 | 3/2005 | Doi |
| 6,879,810 B2 | 4/2005 | Bouet |
| 6,882,881 B1 | 4/2005 | Lesser et al. |
| 6,889,165 B2 | 5/2005 | Lind et al. |
| 6,897,788 B2 | 5/2005 | Khair et al. |
| 6,909,878 B2 | 6/2005 | Haller |
| 6,922,592 B2 | 7/2005 | Thompson et al. |
| 6,928,370 B2 | 8/2005 | Anuzis et al. |
| 6,929,636 B1 | 8/2005 | Von Alten |
| 6,937,150 B2 | 8/2005 | Medema |
| 6,942,616 B2 | 9/2005 | Kerr |
| 6,951,536 B2 | 10/2005 | Yokoi |
| 6,956,917 B2 | 10/2005 | Lenosky |
| 6,957,107 B2 | 10/2005 | Rogers et al. |
| 6,959,929 B2 | 11/2005 | Pugnet et al. |
| 6,961,601 B2 | 11/2005 | Mathews et al. |
| 6,968,153 B1 | 11/2005 | Heinonen |
| 6,987,965 B2 | 1/2006 | Ng et al. |
| 6,990,082 B1 | 1/2006 | Zehavi et al. |
| 7,002,476 B2 | 2/2006 | Rapchak |
| 7,004,395 B2 | 2/2006 | Koenck |
| 7,009,634 B2 | 3/2006 | Iddan et al. |
| 7,009,946 B1 | 3/2006 | Kardach |
| 7,013,162 B2 | 3/2006 | Gorsuch |
| 7,016,648 B2 | 3/2006 | Haller |
| 7,020,508 B2 | 3/2006 | Stivoric |
| 7,024,248 B2 | 4/2006 | Penner et al. |
| 7,031,745 B2 | 4/2006 | Shen |
| 7,031,857 B2 | 4/2006 | Tarassenko et al. |
| 7,039,453 B2 | 5/2006 | Mullick |
| 7,046,649 B2 | 5/2006 | Awater et al. |
| 7,076,437 B1 | 7/2006 | Levy |
| 7,116,252 B2 | 10/2006 | Teraguchi |
| 7,118,531 B2 | 10/2006 | Krill |
| 7,127,300 B2 | 10/2006 | Mazar et al. |
| 7,139,332 B2 | 11/2006 | Yu et al. |
| 7,146,228 B2 | 12/2006 | Nielsen |
| 7,146,449 B2 | 12/2006 | Do et al. |
| 7,148,828 B2 | 12/2006 | Fernandez |
| 7,149,581 B2 | 12/2006 | Goedeke et al. |
| 7,154,071 B2 | 12/2006 | Sattler et al. |
| 7,154,916 B2 | 12/2006 | Soloff |
| 7,155,232 B2 | 12/2006 | Godfrey et al. |
| 7,160,258 B2 | 1/2007 | Imran |
| 7,161,484 B2 | 1/2007 | Tsoukalis |
| 7,164,942 B2 | 1/2007 | Avrahami |
| 7,171,166 B2 | 1/2007 | Ng et al. |
| 7,171,177 B2 | 1/2007 | Park et al. |
| 7,171,259 B2 | 1/2007 | Rytky |
| 7,187,960 B2 | 3/2007 | Abreu |
| 7,188,199 B2 | 3/2007 | Leung et al. |
| 7,188,767 B2 | 3/2007 | Penuela |
| 7,194,038 B1 | 3/2007 | Inkinen |
| 7,206,630 B1 | 4/2007 | Tarler |
| 7,209,790 B2 | 4/2007 | Thompson et al. |
| 7,215,660 B2 | 5/2007 | Perlman |
| 7,215,991 B2 | 5/2007 | Besson |
| 7,218,967 B2 | 5/2007 | Bergelson |
| 7,231,451 B2 | 6/2007 | Law |
| 7,243,118 B2 | 7/2007 | Lou |
| 7,246,521 B2 | 7/2007 | Kim |
| 7,249,212 B2 | 7/2007 | Do |
| 7,252,792 B2 | 8/2007 | Perrault |
| 7,253,716 B2 | 8/2007 | Lovoi et al. |
| 7,261,690 B2 | 8/2007 | Teller |
| 7,270,633 B1 | 9/2007 | Goscha |
| 7,273,454 B2 | 9/2007 | Raymond et al. |
| 7,283,867 B2 | 10/2007 | Strother et al. |
| 7,285,090 B2 | 10/2007 | Stivoric et al. |
| 7,289,855 B2 | 10/2007 | Nghiem |
| 7,291,497 B2 | 11/2007 | Holmes |
| 7,292,139 B2 | 11/2007 | Mazar et al. |
| 7,294,105 B1 | 11/2007 | Islam |
| 7,311,665 B2 | 12/2007 | Hawthorne |
| 7,313,163 B2 | 12/2007 | Liu |
| 7,317,378 B2 | 1/2008 | Jarvis et al. |
| 7,318,808 B2 | 1/2008 | Tarassenko et al. |
| 7,336,929 B2 | 2/2008 | Yasuda |
| 7,342,895 B2 | 3/2008 | Serpa |
| 7,346,380 B2 | 3/2008 | Axelgaard et al. |
| 7,349,722 B2 | 3/2008 | Witkowski et al. |
| 7,352,998 B2 | 4/2008 | Palin |
| 7,353,258 B2 | 4/2008 | Washburn |
| 7,357,891 B2 | 4/2008 | Yang et al. |
| 7,359,674 B2 | 4/2008 | Markki |
| 7,366,558 B2 | 4/2008 | Virtanen et al. |

(56) References Cited

U.S. PATENT DOCUMENTS

| | | | |
|---|---|---|---|
| 7,373,196 | B2 | 5/2008 | Ryu et al. |
| 7,375,739 | B2 | 5/2008 | Robbins |
| 7,376,435 | B2 | 5/2008 | McGowan |
| 7,382,247 | B2 | 6/2008 | Welch et al. |
| 7,382,263 | B2 | 6/2008 | Danowski et al. |
| 7,387,607 | B2 | 6/2008 | Holt |
| 7,388,903 | B2 | 6/2008 | Godfrey et al. |
| 7,389,088 | B2 | 6/2008 | Kim |
| 7,392,015 | B1 | 6/2008 | Farlow |
| 7,395,105 | B2 | 7/2008 | Schmidt et al. |
| 7,395,106 | B2 | 7/2008 | Ryu et al. |
| 7,396,330 | B2 | 7/2008 | Banet |
| 7,404,968 | B2 | 7/2008 | Abrams et al. |
| 7,413,544 | B2 | 8/2008 | Kerr |
| 7,414,534 | B1 | 8/2008 | Kroll et al. |
| 7,415,242 | B1 | 8/2008 | Ngan |
| 7,424,268 | B2 | 9/2008 | Diener |
| 7,424,319 | B2 | 9/2008 | Muehlsteff |
| 7,427,266 | B2 | 9/2008 | Ayer et al. |
| 7,471,665 | B2 | 12/2008 | Perlman |
| 7,476,104 | B2 | 1/2009 | Marmaropoulos et al. |
| 7,499,674 | B2 | 3/2009 | Salokannel |
| 7,502,643 | B2 | 3/2009 | Farringdon et al. |
| 7,505,795 | B1 | 3/2009 | Lim et al. |
| 7,510,121 | B2 | 3/2009 | Koenck |
| 7,512,448 | B2 | 3/2009 | Malick |
| 7,515,043 | B2 | 4/2009 | Welch |
| 7,523,756 | B2 | 4/2009 | Minai |
| 7,525,426 | B2 | 4/2009 | Edelstein |
| 7,539,533 | B2 | 5/2009 | Tran |
| 7,542,878 | B2 | 6/2009 | Nanikashvili |
| 7,547,278 | B2 | 6/2009 | Miyazaki et al. |
| 7,551,590 | B2 | 6/2009 | Haller |
| 7,554,452 | B2 | 6/2009 | Cole |
| 7,575,005 | B2 | 8/2009 | Mumford |
| 7,599,003 | B2 | 10/2009 | Suzuki et al. |
| 7,616,111 | B2 | 11/2009 | Covannon |
| 7,616,710 | B2 | 11/2009 | Kim et al. |
| 7,617,001 | B2 | 11/2009 | Penner et al. |
| 7,626,387 | B2 | 12/2009 | Adachi |
| 7,640,802 | B2 | 1/2010 | King et al. |
| 7,647,112 | B2 | 1/2010 | Tracey |
| 7,647,185 | B2 | 1/2010 | Tarassenko et al. |
| 7,653,031 | B2 | 1/2010 | Godfrey et al. |
| 7,668,437 | B1 | 2/2010 | Yamada et al. |
| 7,672,703 | B2 | 3/2010 | Yeo et al. |
| 7,672,714 | B2 | 3/2010 | Kuo |
| 7,673,679 | B2 | 3/2010 | Harrison et al. |
| 7,678,043 | B2 | 3/2010 | Gilad |
| 7,688,204 | B2 | 3/2010 | Yamanaka et al. |
| 7,689,437 | B1 | 3/2010 | Teller et al. |
| 7,697,994 | B2 | 4/2010 | VanDanacker et al. |
| 7,720,036 | B2 | 5/2010 | Sadri |
| 7,729,776 | B2 | 6/2010 | Von Arx et al. |
| 7,733,224 | B2 | 6/2010 | Tran |
| 7,736,318 | B2 | 6/2010 | Costentino |
| 7,750,790 | B2 | 7/2010 | Yang et al. |
| 7,756,587 | B2 | 7/2010 | Penner et al. |
| 7,782,991 | B2 | 8/2010 | Sobchak et al. |
| 7,797,033 | B2 | 9/2010 | D'Andrea et al. |
| 7,809,399 | B2 | 10/2010 | Lu |
| 7,844,341 | B2 | 11/2010 | Von Arx et al. |
| 7,874,993 | B2 | 1/2011 | Bardy |
| 7,885,700 | B2 | 2/2011 | Clark et al. |
| 7,904,133 | B2 | 3/2011 | Gehman et al. |
| D639,437 | S | 6/2011 | Bishay et al. |
| 7,978,064 | B2 | 7/2011 | Zdeblick et al. |
| 7,983,189 | B2 | 7/2011 | Bugenhagen |
| 8,036,748 | B2 | 10/2011 | Zdeblick et al. |
| 8,055,334 | B2 | 11/2011 | Savage et al. |
| 8,073,707 | B2 | 12/2011 | Teller et al. |
| 8,083,128 | B2 | 12/2011 | Dembo et al. |
| 8,094,807 | B2 | 1/2012 | Ishibashi et al. |
| 8,114,021 | B2 | 2/2012 | Robertson et al. |
| 8,123,576 | B2 | 2/2012 | Kim |
| 8,140,143 | B2 | 3/2012 | Picard et al. |
| 8,160,672 | B2* | 4/2012 | Kim ............... A61B 1/041 128/899 |
| 8,170,515 | B2 | 5/2012 | Le Reverend et al. |
| 8,177,611 | B2 | 5/2012 | Kang |
| 8,180,425 | B2 | 5/2012 | Selvitelli et al. |
| 8,184,854 | B2 | 5/2012 | Bartsch |
| 8,185,191 | B1 | 5/2012 | Shapiro et al. |
| 8,185,646 | B2 | 5/2012 | Headley |
| 8,190,230 | B2 | 5/2012 | Rytky |
| 8,193,821 | B2 | 6/2012 | Mueller |
| 8,200,320 | B2 | 6/2012 | Kovacs |
| 8,214,007 | B2 | 7/2012 | Baker et al. |
| 8,238,998 | B2 | 8/2012 | Park |
| 8,249,686 | B2 | 8/2012 | Libbus et al. |
| 8,253,586 | B1 | 8/2012 | Matak |
| 8,254,853 | B2 | 8/2012 | Rofougaran |
| 8,285,356 | B2 | 10/2012 | Bly et al. |
| 8,290,574 | B2 | 10/2012 | Felid et al. |
| 8,301,232 | B2 | 10/2012 | Albert et al. |
| 8,308,640 | B2 | 11/2012 | Baldus et al. |
| 8,315,687 | B2 | 11/2012 | Cross et al. |
| 8,321,672 | B2 | 11/2012 | Asano |
| 8,332,009 | B2 | 12/2012 | McLaughlin et al. |
| 8,360,976 | B2 | 1/2013 | Imran |
| 8,369,936 | B2 | 2/2013 | Farringdon et al. |
| 8,386,009 | B2 | 2/2013 | Lindberg et al. |
| 8,404,275 | B2 | 3/2013 | Habboushe |
| 8,440,274 | B2 | 5/2013 | Wang |
| 8,454,528 | B2 | 6/2013 | Yuen et al. |
| 8,471,960 | B2 | 6/2013 | Lin et al. |
| 8,514,979 | B2 | 8/2013 | Laporte |
| 8,515,559 | B2 | 8/2013 | Roberts et al. |
| 8,538,544 | B2 | 9/2013 | Sivard |
| 8,545,436 | B2 | 10/2013 | Robertson et al. |
| 8,548,033 | B2 | 10/2013 | Nemeth et al. |
| 8,604,974 | B2 | 12/2013 | Ganeshan |
| 8,615,290 | B2 | 12/2013 | Lin et al. |
| 8,620,402 | B2 | 12/2013 | Parker, III et al. |
| 8,634,838 | B2 | 1/2014 | Hellwig et al. |
| 8,660,645 | B2 | 2/2014 | Stevenson et al. |
| 8,668,643 | B2 | 3/2014 | Kinast |
| 8,725,243 | B2 | 5/2014 | Dilorenzo et al. |
| 8,730,031 | B2 | 5/2014 | Thompson et al. |
| 8,754,799 | B2 | 6/2014 | Coln et al. |
| 8,773,258 | B2 | 7/2014 | Vosch et al. |
| 8,836,513 | B2 | 9/2014 | Hafezi et al. |
| 8,838,217 | B2 | 9/2014 | Myr |
| 8,858,432 | B2 | 10/2014 | Robertson |
| 8,886,281 | B2 | 11/2014 | Pernu et al. |
| 8,886,316 | B1* | 11/2014 | Juels ............... G06F 21/32 607/31 |
| 8,892,194 | B2 | 11/2014 | Balji et al. |
| 8,908,943 | B2 | 12/2014 | Berry et al. |
| 8,920,345 | B2 | 12/2014 | Greenberg |
| 8,923,956 | B2 | 12/2014 | Clark et al. |
| 8,926,509 | B2 | 1/2015 | Magar et al. |
| 8,932,221 | B2 | 1/2015 | Colliou et al. |
| 8,945,005 | B2 | 2/2015 | Hafezi et al. |
| 8,945,328 | B2 | 2/2015 | Longinotti et al. |
| 8,989,837 | B2 | 3/2015 | Weinstein et al. |
| 9,014,779 | B2 | 4/2015 | Zdeblick et al. |
| 9,031,658 | B2 | 5/2015 | Chiao et al. |
| 9,149,577 | B2 | 10/2015 | Robertson et al. |
| 9,158,890 | B2 | 10/2015 | Meredith et al. |
| 9,189,941 | B2 | 11/2015 | Eschelman et al. |
| 9,226,663 | B2 | 1/2016 | Fei |
| 9,226,679 | B2 | 1/2016 | Balda |
| 9,270,025 | B2 | 2/2016 | Robertson et al. |
| 9,270,503 | B2 | 2/2016 | Kushner et al. |
| 9,277,864 | B2 | 3/2016 | Yang et al. |
| 9,320,455 | B2 | 4/2016 | Hafezi et al. |
| 9,439,566 | B2 | 9/2016 | Arne et al. |
| 9,439,582 | B2 | 9/2016 | Berkman et al. |
| 9,439,599 | B2 | 9/2016 | Thompson et al. |
| 9,517,012 | B2 | 12/2016 | Lane et al. |
| 9,577,864 | B2 | 2/2017 | Kushner et al. |
| 9,597,010 | B2 | 3/2017 | Thompson et al. |
| 9,659,423 | B2 | 5/2017 | Robertson et al. |

(56) References Cited

U.S. PATENT DOCUMENTS

| | | |
|---|---|---|
| 9,756,874 B2 | 9/2017 | Arne et al. |
| 9,787,511 B2 | 10/2017 | Fleming et al. |
| 9,820,658 B2 | 11/2017 | Tran |
| 9,946,297 B2 | 4/2018 | Nazzaro et al. |
| 10,498,572 B2 | 12/2019 | Flemming et al. |
| 2001/0027331 A1 | 10/2001 | Thompson |
| 2001/0031071 A1 | 10/2001 | Nichols et al. |
| 2001/0044588 A1 | 11/2001 | Mault |
| 2001/0051766 A1 | 12/2001 | Gazdinski |
| 2001/0056262 A1 | 12/2001 | Cabiri et al. |
| 2002/0002326 A1 | 1/2002 | Causey et al. |
| 2002/0026111 A1 | 2/2002 | Ackerman |
| 2002/0040278 A1 | 4/2002 | Anuzis et al. |
| 2002/0077620 A1 | 6/2002 | Sweeney et al. |
| 2002/0128934 A1 | 9/2002 | Shaer |
| 2002/0132226 A1 | 9/2002 | Nair |
| 2002/0169696 A1 | 11/2002 | Zara |
| 2002/0192159 A1 | 12/2002 | Reitberg |
| 2002/0193669 A1 | 12/2002 | Glukhovsky |
| 2002/0198470 A1 | 12/2002 | Imran et al. |
| 2003/0017826 A1 | 1/2003 | Fishman |
| 2003/0023150 A1 | 1/2003 | Yokoi et al. |
| 2003/0028226 A1 | 2/2003 | Thompson |
| 2003/0065536 A1 | 4/2003 | Hansen |
| 2003/0076179 A1 | 4/2003 | Branch et al. |
| 2003/0083559 A1 | 5/2003 | Thompson |
| 2003/0091121 A1 | 5/2003 | Kenmochi |
| 2003/0126593 A1 | 7/2003 | Mault |
| 2003/0130714 A1 | 7/2003 | Nielsen et al. |
| 2003/0135128 A1 | 7/2003 | Suffin et al. |
| 2003/0135392 A1 | 7/2003 | Vrijens et al. |
| 2003/0152622 A1 | 8/2003 | Louie-Helm et al. |
| 2003/0158466 A1 | 8/2003 | Lynn et al. |
| 2003/0158756 A1 | 8/2003 | Abramson |
| 2003/0162556 A1 | 8/2003 | Libes |
| 2003/0164401 A1 | 9/2003 | Andreasson et al. |
| 2003/0167000 A1 | 9/2003 | Mullick et al. |
| 2003/0171791 A1 | 9/2003 | KenKnight |
| 2003/0171898 A1 | 9/2003 | Tarassenko et al. |
| 2003/0181788 A1 | 9/2003 | Yokoi et al. |
| 2003/0181815 A1 | 9/2003 | Ebner et al. |
| 2003/0185286 A1 | 10/2003 | Yuen |
| 2003/0187337 A1 | 10/2003 | Tarassenko et al. |
| 2003/0187338 A1 | 10/2003 | Say et al. |
| 2003/0195403 A1 | 10/2003 | Berner et al. |
| 2003/0208113 A1 | 11/2003 | Mault et al. |
| 2003/0213495 A1 | 11/2003 | Fujita et al. |
| 2003/0214579 A1 | 11/2003 | Iddan |
| 2003/0216622 A1 | 11/2003 | Meron et al. |
| 2003/0216625 A1 | 11/2003 | Phipps |
| 2003/0216666 A1 | 11/2003 | Ericson et al. |
| 2003/0216729 A1 | 11/2003 | Marchitto |
| 2003/0229382 A1 | 12/2003 | Sun et al. |
| 2004/0008123 A1 | 1/2004 | Carrender et al. |
| 2004/0018476 A1 | 1/2004 | LaDue |
| 2004/0019172 A1 | 1/2004 | Yang et al. |
| 2004/0034295 A1 | 2/2004 | Salganicoff |
| 2004/0049245 A1 | 3/2004 | Gass |
| 2004/0064728 A1* | 4/2004 | Scheurich ............ H04W 12/06 726/9 |
| 2004/0073095 A1 | 4/2004 | Causey et al. |
| 2004/0073454 A1 | 4/2004 | Urquhart et al. |
| 2004/0077995 A1 | 4/2004 | Ferek-Petric |
| 2004/0082982 A1 | 4/2004 | Gord et al. |
| 2004/0087839 A1 | 5/2004 | Raymond et al. |
| 2004/0092801 A1 | 5/2004 | Drakulic |
| 2004/0106859 A1 | 6/2004 | Say et al. |
| 2004/0115507 A1 | 6/2004 | Potter et al. |
| 2004/0115517 A1 | 6/2004 | Fukada et al. |
| 2004/0121015 A1 | 6/2004 | Chidlaw et al. |
| 2004/0122297 A1 | 6/2004 | Stahmann et al. |
| 2004/0148140 A1 | 7/2004 | Tarassenko et al. |
| 2004/0153007 A1 | 8/2004 | Harris |
| 2004/0165686 A1 | 8/2004 | Siwiak |
| 2004/0167226 A1 | 8/2004 | Serafini |
| 2004/0167801 A1 | 8/2004 | Say et al. |
| 2004/0193020 A1 | 9/2004 | Chiba |
| 2004/0193029 A1 | 9/2004 | Gluhovsky |
| 2004/0193446 A1 | 9/2004 | Mayer et al. |
| 2004/0199222 A1 | 10/2004 | Sun et al. |
| 2004/0215084 A1 | 10/2004 | Shimizu et al. |
| 2004/0218683 A1 | 11/2004 | Batra |
| 2004/0220643 A1 | 11/2004 | Schmidt |
| 2004/0224644 A1 | 11/2004 | Wu |
| 2004/0225199 A1 | 11/2004 | Evanyk |
| 2004/0240481 A1 | 12/2004 | Matsumoto |
| 2004/0253304 A1 | 12/2004 | Gross et al. |
| 2004/0260154 A1 | 12/2004 | Sidelnik |
| 2005/0010338 A1 | 1/2005 | Kraeling et al. |
| 2005/0017841 A1 | 1/2005 | Doi |
| 2005/0020887 A1 | 1/2005 | Goldberg |
| 2005/0021103 A1 | 1/2005 | DiLorenzo |
| 2005/0021370 A1 | 1/2005 | Riff |
| 2005/0024198 A1 | 2/2005 | Ward |
| 2005/0027205 A1 | 2/2005 | Tarassenko et al. |
| 2005/0038321 A1 | 2/2005 | Fujita et al. |
| 2005/0041752 A1* | 2/2005 | Rosen ............... H04L 27/001 375/268 |
| 2005/0043634 A1 | 2/2005 | Yokoi et al. |
| 2005/0055014 A1 | 3/2005 | Coppeta et al. |
| 2005/0062644 A1 | 3/2005 | Leci |
| 2005/0065407 A1 | 3/2005 | Nakamura et al. |
| 2005/0070778 A1 | 3/2005 | Lackey |
| 2005/0092108 A1 | 5/2005 | Andermo |
| 2005/0096514 A1 | 5/2005 | Starkebaum |
| 2005/0096562 A1 | 5/2005 | Delalic et al. |
| 2005/0101843 A1 | 5/2005 | Quinn |
| 2005/0101872 A1 | 5/2005 | Sattler |
| 2005/0115561 A1 | 6/2005 | Stahmann et al. |
| 2005/0116820 A1 | 6/2005 | Goldreich |
| 2005/0117389 A1 | 6/2005 | Worledge |
| 2005/0121322 A1 | 6/2005 | Say et al. |
| 2005/0131281 A1 | 6/2005 | Ayer et al. |
| 2005/0137480 A1 | 6/2005 | Alt et al. |
| 2005/0143623 A1 | 6/2005 | Kojima |
| 2005/0148883 A1 | 7/2005 | Boesen |
| 2005/0154428 A1 | 7/2005 | Bruinsma |
| 2005/0165323 A1 | 7/2005 | Montgomery |
| 2005/0177069 A1 | 8/2005 | Takizawa |
| 2005/0182389 A1 | 8/2005 | LaPorte |
| 2005/0187789 A1 | 8/2005 | Hatlestad et al. |
| 2005/0192489 A1 | 9/2005 | Marshall |
| 2005/0197680 A1 | 9/2005 | DelMain et al. |
| 2005/0228268 A1 | 10/2005 | Cole |
| 2005/0234307 A1 | 10/2005 | Heinonen |
| 2005/0240305 A1 | 10/2005 | Bogash et al. |
| 2005/0245794 A1 | 11/2005 | Dinsmoor |
| 2005/0259768 A1 | 11/2005 | Yang et al. |
| 2005/0261559 A1 | 11/2005 | Mumford |
| 2005/0267556 A1 | 12/2005 | Shuros et al. |
| 2005/0267756 A1 | 12/2005 | Schultz et al. |
| 2005/0277912 A1 | 12/2005 | John |
| 2005/0277999 A1 | 12/2005 | Strother et al. |
| 2005/0285746 A1 | 12/2005 | Sengupta |
| 2005/0288594 A1 | 12/2005 | Lewkowicz et al. |
| 2006/0001496 A1 | 1/2006 | Abrosimov et al. |
| 2006/0036134 A1 | 2/2006 | Tarassenko et al. |
| 2006/0061472 A1 | 3/2006 | Lovoi et al. |
| 2006/0065713 A1 | 3/2006 | Kingery |
| 2006/0074283 A1 | 4/2006 | Henderson |
| 2006/0078765 A1 | 4/2006 | Yang et al. |
| 2006/0095091 A1 | 5/2006 | Drew |
| 2006/0095093 A1 | 5/2006 | Bettesh et al. |
| 2006/0100533 A1 | 5/2006 | Han |
| 2006/0109058 A1 | 5/2006 | Keating |
| 2006/0110962 A1 | 5/2006 | Powell |
| 2006/0122474 A1 | 6/2006 | Teller et al. |
| 2006/0122667 A1 | 6/2006 | Chavan et al. |
| 2006/0129060 A1 | 6/2006 | Lee et al. |
| 2006/0136266 A1 | 6/2006 | Tarassenko et al. |
| 2006/0136744 A1* | 6/2006 | Lange ................ G06K 9/00536 713/186 |
| 2006/0142648 A1 | 6/2006 | Banet |
| 2006/0145876 A1 | 7/2006 | Kimura |

(56) References Cited

U.S. PATENT DOCUMENTS

| | | |
|---|---|---|
| 2006/0148254 A1 | 7/2006 | McLean |
| 2006/0149339 A1 | 7/2006 | Burnes |
| 2006/0155174 A1 | 7/2006 | Glukhovsky et al. |
| 2006/0155183 A1 | 7/2006 | Kroecker |
| 2006/0158820 A1 | 7/2006 | Takiguchi |
| 2006/0161225 A1 | 7/2006 | Sormann et al. |
| 2006/0179949 A1 | 8/2006 | Kim |
| 2006/0183993 A1 | 8/2006 | Horn |
| 2006/0184092 A1 | 8/2006 | Atanasoska et al. |
| 2006/0204738 A1 | 9/2006 | Dubrow et al. |
| 2006/0210626 A1 | 9/2006 | Spaeder |
| 2006/0216603 A1 | 9/2006 | Choi |
| 2006/0218011 A1 | 9/2006 | Walker |
| 2006/0235489 A1 | 10/2006 | Drew |
| 2006/0247505 A1 | 11/2006 | Siddiqui |
| 2006/0253005 A1 | 11/2006 | Drinan |
| 2006/0255064 A1 | 11/2006 | Donaldson |
| 2006/0265246 A1 | 11/2006 | Hoag |
| 2006/0268170 A1 | 11/2006 | Suzuki et al. |
| 2006/0269019 A1 | 11/2006 | Simmons et al. |
| 2006/0270346 A1 | 11/2006 | Ibrahim |
| 2006/0277097 A1 | 12/2006 | Shafron et al. |
| 2006/0280227 A1 | 12/2006 | Pinkney |
| 2006/0282001 A1 | 12/2006 | Noel |
| 2006/0289640 A1 | 12/2006 | Mercure |
| 2006/0293607 A1 | 12/2006 | Alt |
| 2007/0002038 A1 | 1/2007 | Suzuki |
| 2007/0006636 A1 | 1/2007 | King et al. |
| 2007/0008113 A1 | 1/2007 | Spoonhower et al. |
| 2007/0016089 A1 | 1/2007 | Fischell et al. |
| 2007/0027386 A1 | 2/2007 | Such |
| 2007/0027388 A1 | 2/2007 | Chou |
| 2007/0038054 A1 | 2/2007 | Zhou |
| 2007/0049339 A1 | 3/2007 | Barak et al. |
| 2007/0055098 A1 | 3/2007 | Shimizu et al. |
| 2007/0060797 A1 | 3/2007 | Ball |
| 2007/0073353 A1 | 3/2007 | Rooney et al. |
| 2007/0096765 A1 | 5/2007 | Kagan |
| 2007/0106346 A1 | 5/2007 | Bergelson |
| 2007/0123772 A1 | 5/2007 | Euliano |
| 2007/0129622 A1 | 6/2007 | Bourget |
| 2007/0130287 A1 | 6/2007 | Kumar |
| 2007/0135803 A1 | 6/2007 | Belson |
| 2007/0142721 A1 | 6/2007 | Berner et al. |
| 2007/0156016 A1 | 7/2007 | Betesh |
| 2007/0162089 A1 | 7/2007 | Mosesov |
| 2007/0162090 A1 | 7/2007 | Penner |
| 2007/0164752 A1* | 7/2007 | Kato .............. A61B 5/0006 324/606 |
| 2007/0167495 A1 | 7/2007 | Brown et al. |
| 2007/0167848 A1 | 7/2007 | Kuo et al. |
| 2007/0173701 A1 | 7/2007 | Al-Ali |
| 2007/0179347 A1 | 8/2007 | Tarassenko et al. |
| 2007/0180047 A1 | 8/2007 | Dong et al. |
| 2007/0185393 A1 | 8/2007 | Zhou |
| 2007/0191002 A1 | 8/2007 | Ge |
| 2007/0196456 A1 | 8/2007 | Stevens |
| 2007/0207793 A1 | 9/2007 | Myer |
| 2007/0213659 A1 | 9/2007 | Trovato et al. |
| 2007/0237719 A1 | 10/2007 | Jones |
| 2007/0244370 A1 | 10/2007 | Kuo et al. |
| 2007/0249946 A1 | 10/2007 | Kumar et al. |
| 2007/0255198 A1 | 11/2007 | Leong et al. |
| 2007/0255330 A1 | 11/2007 | Lee |
| 2007/0270672 A1 | 11/2007 | Hayter |
| 2007/0279217 A1 | 12/2007 | Venkatraman |
| 2007/0282174 A1 | 12/2007 | Sabatino |
| 2007/0282177 A1 | 12/2007 | Pilz |
| 2007/0291715 A1 | 12/2007 | Laroia et al. |
| 2007/0299480 A1 | 12/2007 | Hill |
| 2008/0014866 A1 | 1/2008 | Lipowshi |
| 2008/0015421 A1 | 1/2008 | Penner |
| 2008/0015494 A1 | 1/2008 | Santini et al. |
| 2008/0020037 A1 | 1/2008 | Robertson et al. |
| 2008/0021519 A1 | 1/2008 | DeGeest |
| 2008/0021521 A1 | 1/2008 | Shah |
| 2008/0027679 A1 | 1/2008 | Shklarski |
| 2008/0033273 A1 | 2/2008 | Zhou |
| 2008/0044025 A1* | 2/2008 | Corndorf .............. H04L 9/0631 380/270 |
| 2008/0045843 A1 | 2/2008 | Tsuji et al. |
| 2008/0046038 A1 | 2/2008 | Hill |
| 2008/0051667 A1 | 2/2008 | Goldreich |
| 2008/0051767 A1 | 2/2008 | Rossing et al. |
| 2008/0058614 A1 | 3/2008 | Banet |
| 2008/0062856 A1 | 3/2008 | Feher |
| 2008/0065168 A1 | 3/2008 | Bitton et al. |
| 2008/0069397 A1* | 3/2008 | Bartsch ................ G06F 19/321 382/100 |
| 2008/0074307 A1 | 3/2008 | Boric-Lubecke |
| 2008/0077015 A1 | 3/2008 | Botic-Lubecke |
| 2008/0077028 A1 | 3/2008 | Schaldach et al. |
| 2008/0077188 A1 | 3/2008 | Denker et al. |
| 2008/0091089 A1 | 4/2008 | Guillory et al. |
| 2008/0091114 A1 | 4/2008 | Min |
| 2008/0097549 A1 | 4/2008 | Colbaugh |
| 2008/0097917 A1 | 4/2008 | Dicks |
| 2008/0099366 A1 | 5/2008 | Niemic et al. |
| 2008/0103440 A1 | 5/2008 | Ferren et al. |
| 2008/0112885 A1 | 5/2008 | Okunev et al. |
| 2008/0114224 A1 | 5/2008 | Bandy et al. |
| 2008/0119705 A1 | 5/2008 | Patel |
| 2008/0119716 A1 | 5/2008 | Boric-Lubecke |
| 2008/0137566 A1 | 6/2008 | Marholev |
| 2008/0139907 A1 | 6/2008 | Rao et al. |
| 2008/0139953 A1* | 6/2008 | Baker .................. A61B 5/0006 600/509 |
| 2008/0140403 A1 | 6/2008 | Hughes et al. |
| 2008/0146871 A1 | 6/2008 | Arneson et al. |
| 2008/0146889 A1 | 6/2008 | Young |
| 2008/0146892 A1 | 6/2008 | LeBeouf |
| 2008/0154104 A1 | 6/2008 | Lamego |
| 2008/0166992 A1 | 7/2008 | Ricordi |
| 2008/0183245 A1 | 7/2008 | Van Oort |
| 2008/0188837 A1 | 8/2008 | Belsky et al. |
| 2008/0194912 A1 | 8/2008 | Trovato et al. |
| 2008/0208009 A1 | 8/2008 | Shklarski |
| 2008/0214901 A1 | 9/2008 | Gehman |
| 2008/0214985 A1 | 9/2008 | Yanaki |
| 2008/0243020 A1 | 10/2008 | Chou |
| 2008/0249360 A1 | 10/2008 | Li |
| 2008/0262320 A1 | 10/2008 | Schaefer et al. |
| 2008/0262336 A1 | 10/2008 | Ryu |
| 2008/0269664 A1 | 10/2008 | Trovato et al. |
| 2008/0275312 A1 | 11/2008 | Mosesov |
| 2008/0284599 A1 | 11/2008 | Zdeblick et al. |
| 2008/0288026 A1 | 11/2008 | Cross et al. |
| 2008/0288027 A1 | 11/2008 | Kroll |
| 2008/0294020 A1 | 11/2008 | Sapounas |
| 2008/0300572 A1 | 12/2008 | Rankers |
| 2008/0303638 A1 | 12/2008 | Nguyen |
| 2008/0306357 A1 | 12/2008 | Korman |
| 2008/0306359 A1 | 12/2008 | Zdeblick et al. |
| 2008/0306360 A1 | 12/2008 | Robertson et al. |
| 2008/0306362 A1 | 12/2008 | Davis |
| 2008/0311852 A1 | 12/2008 | Hansen |
| 2008/0312522 A1 | 12/2008 | Rowlandson |
| 2008/0316020 A1 | 12/2008 | Robertson |
| 2009/0009332 A1 | 1/2009 | Nunez et al. |
| 2009/0018409 A1 | 1/2009 | Banet et al. |
| 2009/0024045 A1 | 1/2009 | Prakash |
| 2009/0030293 A1 | 1/2009 | Cooper et al. |
| 2009/0030297 A1 | 1/2009 | Miller |
| 2009/0034209 A1 | 2/2009 | Joo |
| 2009/0043171 A1 | 2/2009 | Rule |
| 2009/0048498 A1 | 2/2009 | Riskey |
| 2009/0062634 A1 | 3/2009 | Say et al. |
| 2009/0062670 A1 | 3/2009 | Sterling |
| 2009/0062730 A1 | 3/2009 | Woo |
| 2009/0069642 A1 | 3/2009 | Gao |
| 2009/0069655 A1 | 3/2009 | Say et al. |
| 2009/0069656 A1 | 3/2009 | Say et al. |
| 2009/0069657 A1 | 3/2009 | Say et al. |
| 2009/0069658 A1 | 3/2009 | Say et al. |

(56) References Cited

U.S. PATENT DOCUMENTS

| | | |
|---|---|---|
| 2009/0069724 A1 | 3/2009 | Otto et al. |
| 2009/0076340 A1 | 3/2009 | Libbus et al. |
| 2009/0076343 A1 | 3/2009 | James |
| 2009/0076350 A1 | 3/2009 | Bly et al. |
| 2009/0076397 A1 | 3/2009 | Libbus et al. |
| 2009/0082645 A1 | 3/2009 | Hafezi et al. |
| 2009/0088618 A1 | 4/2009 | Ameson |
| 2009/0099435 A1 | 4/2009 | Say et al. |
| 2009/0110148 A1 | 4/2009 | Zhang |
| 2009/0112626 A1 | 4/2009 | Talbot |
| 2009/0124871 A1 | 5/2009 | Arshak |
| 2009/0131774 A1 | 5/2009 | Sweitzer |
| 2009/0135886 A1 | 5/2009 | Robertson et al. |
| 2009/0153397 A1 | 6/2009 | Li et al. |
| 2009/0157113 A1 | 6/2009 | Marcotte |
| 2009/0157358 A1 | 6/2009 | Kim |
| 2009/0161602 A1 | 6/2009 | Matsumoto |
| 2009/0163789 A1 | 6/2009 | Say et al. |
| 2009/0171180 A1 | 7/2009 | Pering |
| 2009/0173628 A1 | 7/2009 | Say et al. |
| 2009/0177055 A1 | 7/2009 | Say et al. |
| 2009/0177056 A1 | 7/2009 | Say et al. |
| 2009/0177057 A1 | 7/2009 | Say et al. |
| 2009/0177058 A1 | 7/2009 | Say et al. |
| 2009/0177059 A1 | 7/2009 | Say et al. |
| 2009/0177060 A1 | 7/2009 | Say et al. |
| 2009/0177061 A1 | 7/2009 | Say et al. |
| 2009/0177062 A1 | 7/2009 | Say et al. |
| 2009/0177063 A1 | 7/2009 | Say et al. |
| 2009/0177064 A1 | 7/2009 | Say et al. |
| 2009/0177065 A1 | 7/2009 | Say et al. |
| 2009/0177066 A1 | 7/2009 | Say et al. |
| 2009/0182206 A1 | 7/2009 | Najafi |
| 2009/0182212 A1 | 7/2009 | Say et al. |
| 2009/0182213 A1 | 7/2009 | Say et al. |
| 2009/0182214 A1 | 7/2009 | Say et al. |
| 2009/0182215 A1 | 7/2009 | Say et al. |
| 2009/0182388 A1 | 7/2009 | Von Arx |
| 2009/0187088 A1 | 7/2009 | Say et al. |
| 2009/0187089 A1 | 7/2009 | Say et al. |
| 2009/0187090 A1 | 7/2009 | Say et al. |
| 2009/0187091 A1 | 7/2009 | Say et al. |
| 2009/0187092 A1 | 7/2009 | Say et al. |
| 2009/0187093 A1 | 7/2009 | Say et al. |
| 2009/0187094 A1 | 7/2009 | Say et al. |
| 2009/0187095 A1 | 7/2009 | Say et al. |
| 2009/0187381 A1 | 7/2009 | King et al. |
| 2009/0192351 A1 | 7/2009 | Nishino |
| 2009/0192368 A1 | 7/2009 | Say et al. |
| 2009/0192369 A1 | 7/2009 | Say et al. |
| 2009/0192370 A1 | 7/2009 | Say et al. |
| 2009/0192371 A1 | 7/2009 | Say et al. |
| 2009/0192372 A1 | 7/2009 | Say et al. |
| 2009/0192373 A1 | 7/2009 | Say et al. |
| 2009/0192374 A1 | 7/2009 | Say et al. |
| 2009/0192375 A1 | 7/2009 | Say et al. |
| 2009/0192376 A1 | 7/2009 | Say et al. |
| 2009/0192377 A1 | 7/2009 | Say et al. |
| 2009/0192378 A1 | 7/2009 | Say et al. |
| 2009/0192379 A1 | 7/2009 | Say et al. |
| 2009/0198115 A1 | 8/2009 | Say et al. |
| 2009/0198116 A1 | 8/2009 | Say et al. |
| 2009/0198175 A1 | 8/2009 | Say et al. |
| 2009/0199282 A1* | 8/2009 | Tsitkova ............ G06K 9/00006 726/7 |
| 2009/0203964 A1 | 8/2009 | Shimizu et al. |
| 2009/0203971 A1 | 8/2009 | Sciarappa |
| 2009/0203972 A1 | 8/2009 | Heneghan |
| 2009/0203978 A1 | 8/2009 | Say et al. |
| 2009/0204265 A1 | 8/2009 | Hackett |
| 2009/0210164 A1 | 8/2009 | Say et al. |
| 2009/0216101 A1 | 8/2009 | Say et al. |
| 2009/0216102 A1 | 8/2009 | Say et al. |
| 2009/0227204 A1 | 9/2009 | Robertson et al. |
| 2009/0227876 A1 | 9/2009 | Tran |
| 2009/0227940 A1 | 9/2009 | Say et al. |
| 2009/0227941 A1 | 9/2009 | Say et al. |
| 2009/0228214 A1 | 9/2009 | Say et al. |
| 2009/0231125 A1 | 9/2009 | Baldus |
| 2009/0234200 A1 | 9/2009 | Husheer |
| 2009/0243833 A1 | 10/2009 | Huang |
| 2009/0253960 A1 | 10/2009 | Takenaka et al. |
| 2009/0256702 A1 | 10/2009 | Robertson |
| 2009/0258669 A1 | 10/2009 | Nie et al. |
| 2009/0264714 A1 | 10/2009 | Chou |
| 2009/0264964 A1 | 10/2009 | Abrahamson |
| 2009/0265186 A1 | 10/2009 | Tarassenko et al. |
| 2009/0273467 A1 | 11/2009 | Elixmann |
| 2009/0281539 A1 | 11/2009 | Selig |
| 2009/0287109 A1 | 11/2009 | Ferren et al. |
| 2009/0292194 A1 | 11/2009 | Libbus et al. |
| 2009/0295548 A1 | 12/2009 | Ronkka |
| 2009/0296677 A1 | 12/2009 | Mahany |
| 2009/0301925 A1 | 12/2009 | Alloro et al. |
| 2009/0303920 A1 | 12/2009 | Mahany |
| 2009/0309708 A1 | 12/2009 | Hasegawa |
| 2009/0312619 A1 | 12/2009 | Say et al. |
| 2009/0318761 A1 | 12/2009 | Rabinovitz |
| 2009/0318779 A1 | 12/2009 | Tran |
| 2009/0318783 A1 | 12/2009 | Rohde |
| 2009/0318793 A1 | 12/2009 | Datta |
| 2010/0010330 A1 | 1/2010 | Rankers |
| 2010/0033324 A1 | 2/2010 | Shimizu et al. |
| 2010/0036269 A1 | 2/2010 | Ferren et al. |
| 2010/0049006 A1 | 2/2010 | Magar |
| 2010/0049012 A1 | 2/2010 | Dijksman et al. |
| 2010/0049069 A1 | 2/2010 | Tarassenko et al. |
| 2010/0049263 A1 | 2/2010 | Reeve |
| 2010/0056878 A1 | 3/2010 | Partin |
| 2010/0056891 A1 | 3/2010 | Say et al. |
| 2010/0056939 A1 | 3/2010 | Tarassenko et al. |
| 2010/0057041 A1 | 3/2010 | Hayter |
| 2010/0060300 A1 | 3/2010 | Muller |
| 2010/0062709 A1 | 3/2010 | Kato |
| 2010/0063438 A1 | 3/2010 | Bengtsson |
| 2010/0063841 A1 | 3/2010 | D'Ambrosia et al. |
| 2010/0069002 A1 | 3/2010 | Rong |
| 2010/0069717 A1 | 3/2010 | Hafezi et al. |
| 2010/0099967 A1 | 4/2010 | Say et al. |
| 2010/0099968 A1 | 4/2010 | Say et al. |
| 2010/0099969 A1 | 4/2010 | Say et al. |
| 2010/0100077 A1 | 4/2010 | Rush |
| 2010/0100078 A1 | 4/2010 | Say et al. |
| 2010/0106001 A1 | 4/2010 | Say et al. |
| 2010/0113950 A1* | 5/2010 | Lin ................ A61B 5/02438 600/509 |
| 2010/0118853 A1 | 5/2010 | Godfrey |
| 2010/0121315 A1* | 5/2010 | Trovato ................ H04L 9/3278 604/890.1 |
| 2010/0128175 A1 | 5/2010 | Lin |
| 2010/0139672 A1 | 6/2010 | Kroll et al. |
| 2010/0160742 A1 | 6/2010 | Seidl et al. |
| 2010/0168659 A1 | 7/2010 | Say et al. |
| 2010/0179398 A1 | 7/2010 | Say et al. |
| 2010/0185055 A1* | 7/2010 | Robertson ............ A61B 5/0031 600/117 |
| 2010/0191073 A1 | 7/2010 | Tarassenko et al. |
| 2010/0210299 A1 | 8/2010 | Gorbachov |
| 2010/0218249 A1* | 8/2010 | Wilson ............... H04W 12/0608 726/19 |
| 2010/0222652 A1 | 9/2010 | Cho |
| 2010/0228113 A1 | 9/2010 | Solosko |
| 2010/0234706 A1 | 9/2010 | Gilland |
| 2010/0234715 A1 | 9/2010 | Shin |
| 2010/0234914 A1 | 9/2010 | Shen |
| 2010/0245091 A1 | 9/2010 | Singh |
| 2010/0249541 A1 | 9/2010 | Geva et al. |
| 2010/0249881 A1 | 9/2010 | Corndorf |
| 2010/0256461 A1 | 10/2010 | Mohamedali |
| 2010/0259543 A1 | 10/2010 | Tarassenko et al. |
| 2010/0268048 A1 | 10/2010 | Say et al. |
| 2010/0268049 A1 | 10/2010 | Say et al. |
| 2010/0268050 A1 | 10/2010 | Say et al. |
| 2010/0274111 A1 | 10/2010 | Say et al. |

(56) References Cited

U.S. PATENT DOCUMENTS

| | | |
|---|---|---|
| 2010/0280345 A1 | 11/2010 | Say et al. |
| 2010/0280346 A1 | 11/2010 | Say et al. |
| 2010/0298650 A1 | 11/2010 | Moon et al. |
| 2010/0298730 A1 | 11/2010 | Tarassenko et al. |
| 2010/0311482 A1* | 12/2010 | Lange .................. A61B 5/0404 463/1 |
| 2010/0312580 A1 | 12/2010 | Tarassenko et al. |
| 2011/0004079 A1 | 1/2011 | Al Ali et al. |
| 2011/0065983 A1 | 3/2011 | Hafezi et al. |
| 2011/0081860 A1 | 4/2011 | Brown et al. |
| 2011/0124983 A1 | 5/2011 | Kroll et al. |
| 2011/0134906 A1 | 6/2011 | Garudadri et al. |
| 2011/0144470 A1 | 6/2011 | Mazar et al. |
| 2011/0160549 A1 | 6/2011 | Saroka et al. |
| 2011/0166937 A1 | 7/2011 | Bangera et al. |
| 2011/0196454 A1 | 8/2011 | Strand et al. |
| 2011/0208013 A1* | 8/2011 | Phan .................. A61B 5/002 600/301 |
| 2011/0237922 A1* | 9/2011 | Parker, III .......... A61B 5/0006 600/382 |
| 2011/0237924 A1 | 9/2011 | McGusty et al. |
| 2011/0270135 A1 | 11/2011 | Dooley et al. |
| 2011/0279963 A1 | 11/2011 | Kumar et al. |
| 2012/0016231 A1 | 1/2012 | Westmoreland |
| 2012/0029307 A1 | 2/2012 | Paquet et al. |
| 2012/0029309 A1 | 2/2012 | Paquet et al. |
| 2012/0032816 A1 | 2/2012 | Cho et al. |
| 2012/0332778 | 2/2012 | Nakano et al. |
| 2012/0071743 A1 | 3/2012 | Todorov et al. |
| 2012/0083715 A1 | 4/2012 | Yuen et al. |
| 2012/0086550 A1* | 4/2012 | LeBlanc .............. A61B 5/1038 340/5.82 |
| 2012/0089000 A1 | 4/2012 | Bishay et al. |
| 2012/0101396 A1 | 4/2012 | Solosko et al. |
| 2012/0163426 A1 | 6/2012 | Nemeth |
| 2012/0179004 A1 | 7/2012 | Roesicke et al. |
| 2012/0197144 A1 | 8/2012 | Christ et al. |
| 2012/0299723 A1 | 11/2012 | Hafezi et al. |
| 2012/0306662 A1* | 12/2012 | Vosch .................. H04Q 9/00 340/870.07 |
| 2012/0310070 A1 | 12/2012 | Kumar et al. |
| 2012/0316413 A1 | 12/2012 | Liu et al. |
| 2012/0323136 A1 | 12/2012 | Shiftman et al. |
| 2013/0002435 A1* | 1/2013 | Utter, II ............ A61B 5/1118 340/575 |
| 2013/0021166 A1 | 1/2013 | Shah et al. |
| 2013/0027344 A1* | 1/2013 | Choon .................. G06F 3/044 345/174 |
| 2013/0030259 A1 | 1/2013 | Thomsen et al. |
| 2013/0057385 A1 | 3/2013 | Murakami et al. |
| 2013/0060115 A1 | 3/2013 | Gehman et al. |
| 2013/0171596 A1 | 7/2013 | French |
| 2013/0185228 A1 | 7/2013 | Dresner |
| 2013/0194118 A1 | 8/2013 | Coln et al. |
| 2013/0196012 A1 | 8/2013 | Dill |
| 2013/0218022 A1* | 8/2013 | Larsen .................. A61B 5/01 600/474 |
| 2013/0231188 A1 | 9/2013 | Berberich et al. |
| 2013/0238647 A1 | 9/2013 | Thompson |
| 2013/0275296 A1 | 10/2013 | Tietzen et al. |
| 2014/0051946 A1 | 2/2014 | Arne et al. |
| 2014/0066726 A1 | 3/2014 | Costello |
| 2014/0280125 A1 | 9/2014 | Bhardwaj et al. |
| 2014/0300490 A1* | 10/2014 | Kotz .................. A61B 5/0028 340/870.3 |
| 2014/0308930 A1 | 10/2014 | Tran |
| 2014/0349256 A1 | 11/2014 | Connor |
| 2014/0374276 A1 | 12/2014 | Guthrie et al. |
| 2015/0080678 A1 | 3/2015 | Frank et al. |
| 2015/0080679 A1 | 3/2015 | Frank et al. |
| 2015/0080680 A1 | 3/2015 | Zdeblick et al. |
| 2015/0080681 A1 | 3/2015 | Hafezi et al. |
| 2015/0127737 A1 | 5/2015 | Thompson et al. |
| 2015/0127738 A1 | 5/2015 | Thompson et al. |
| 2015/0149375 A1 | 5/2015 | Thompson et al. |
| 2015/0182170 A1 | 7/2015 | Zdeblick et al. |
| 2015/0248833 A1 | 9/2015 | Arne et al. |
| 2016/0324442 A1 | 11/2016 | Zdeblick et al. |
| 2018/0184698 A1 | 7/2018 | Arne et al. |
| 2019/0191006 A1 | 6/2019 | Thompson |
| 2019/0261888 A1 | 8/2019 | Zdeblick et al. |

FOREIGN PATENT DOCUMENTS

| | | |
|---|---|---|
| CN | 101005470 | 7/2007 |
| CN | 101032396 | 9/2007 |
| CN | 201076456 | 6/2008 |
| DE | 10313005 | 10/2004 |
| EP | 0526166 | 2/1993 |
| EP | 1246356 | 10/2002 |
| EP | 1451595 | 9/2004 |
| EP | 1530224 | 5/2005 |
| EP | 1789128 | 5/2007 |
| EP | 2063535 | 5/2009 |
| EP | 2143369 | 1/2010 |
| JP | 61072712 | 4/1986 |
| JP | S62112529 | 5/1987 |
| JP | 05228128 | 9/1993 |
| JP | 1014898 | 1/1998 |
| JP | H11195415 | 7/1999 |
| JP | 2000506410 | 5/2000 |
| JP | 2001070267 | 3/2001 |
| JP | 2001198096 | 7/2001 |
| JP | 2002224053 | 8/2002 |
| JP | 2002282219 | 10/2002 |
| JP | 2002291684 | 10/2002 |
| JP | 2003050867 | 2/2003 |
| JP | 2004007187 | 1/2004 |
| JP | 2004313242 | 11/2004 |
| JP | 2005073886 | 3/2005 |
| JP | 2005102959 | 4/2005 |
| JP | 2005137683 | 6/2005 |
| JP | 2005304880 | 11/2005 |
| JP | 2005532841 | 11/2005 |
| JP | 2005532849 | 11/2005 |
| JP | 2006508752 | 3/2006 |
| JP | 2006509574 | 3/2006 |
| JP | 2006136405 | 6/2006 |
| JP | 2006177699 | 7/2006 |
| JP | 2006268614 | 10/2006 |
| JP | 2007167448 | 7/2007 |
| JP | 2007200739 | 8/2007 |
| JP | 2007313340 | 12/2007 |
| JP | 2008011865 | 1/2008 |
| JP | 2008501415 | 1/2008 |
| JP | 2008086390 | 4/2008 |
| JP | 2008181295 | 8/2008 |
| JP | 2008191110 | 8/2008 |
| JP | 2008212488 | 9/2008 |
| JP | 2009528909 | 8/2009 |
| JP | 2010049490 | 3/2010 |
| JP | 2011086027 | 4/2011 |
| JP | 2012039370 | 2/2012 |
| JP | 2012200309 | 10/2012 |
| JP | 2012212362 | 11/2012 |
| KR | 927471 | 11/2009 |
| KR | 10-2012-099995 | 9/2012 |
| TW | 553735 | 9/2003 |
| TW | 200724094 | 7/2007 |
| WO | WO1988002237 | 4/1988 |
| WO | WO1993008734 | 5/1993 |
| WO | WO1993019667 | 10/1993 |
| WO | WO1997014112 | 4/1997 |
| WO | WO1998043537 | 10/1998 |
| WO | WO1999059465 | 11/1999 |
| WO | WO2000033246 | 6/2000 |
| WO | WO2001000085 | 1/2001 |
| WO | WO2001047466 | 7/2001 |
| WO | WO2001074011 | 10/2001 |
| WO | WO2001080731 | 11/2001 |
| WO | WO2002045489 | 6/2002 |
| WO | WO2002058330 | 7/2002 |
| WO | WO2002062276 | 8/2002 |

(56) References Cited

FOREIGN PATENT DOCUMENTS

| | | |
|---|---|---|
| WO | WO2002087681 | 11/2002 |
| WO | WO2003050643 | 6/2003 |
| WO | WO2003056491 | 7/2003 |
| WO | WO2004014225 | 2/2004 |
| WO | WO2004039256 | 5/2004 |
| WO | WO2004059551 | 7/2004 |
| WO | WO2004066834 | 8/2004 |
| WO | WO2004068748 | 8/2004 |
| WO | WO2004068881 | 8/2004 |
| WO | WO2004075751 | 9/2004 |
| WO | WO2004109316 | 12/2004 |
| WO | WO2005011237 | 2/2005 |
| WO | WO2005013503 | 2/2005 |
| WO | WO2005020023 | 3/2005 |
| WO | WO2005024687 | 3/2005 |
| WO | WO2005041767 | 5/2005 |
| WO | WO2005046575 | 5/2005 |
| WO | WO2005047837 | 5/2005 |
| WO | WO2005051166 | 6/2005 |
| WO | WO2005055448 | 6/2005 |
| WO | WO2005082436 | 9/2005 |
| WO | WO2005084533 | 9/2005 |
| WO | WO2005110238 | 11/2005 |
| WO | WO2006027586 | 3/2006 |
| WO | WO2006035351 | 4/2006 |
| WO | WO2006046648 | 5/2006 |
| WO | WO2006055892 | 5/2006 |
| WO | WO2006055956 | 5/2006 |
| WO | WO2006066566 | 6/2006 |
| WO | WO2006075016 | 7/2006 |
| WO | WO2006094513 | 9/2006 |
| WO | WO2006100620 | 9/2006 |
| WO | WO2006104843 | 10/2006 |
| WO | WO2006109072 | 10/2006 |
| WO | WO2006116718 | 11/2006 |
| WO | WO2006119345 | 11/2006 |
| WO | WO2006127355 | 11/2006 |
| WO | WO2007001724 | 1/2007 |
| WO | WO2007001742 | 1/2007 |
| WO | WO2007013952 | 2/2007 |
| WO | WO2007014084 | 2/2007 |
| WO | WO2007014527 | 2/2007 |
| WO | WO2007021496 | 2/2007 |
| WO | WO2007027660 | 3/2007 |
| WO | WO2007028035 | 3/2007 |
| WO | WO2007036687 | 4/2007 |
| WO | WO2007036741 | 4/2007 |
| WO | WO2007036746 | 4/2007 |
| WO | WO2007040878 | 4/2007 |
| WO | WO2007071180 | 6/2007 |
| WO | WO2007096810 | 8/2007 |
| WO | WO2007101141 | 9/2007 |
| WO | WO2007120946 | 10/2007 |
| WO | WO2007127316 | 11/2007 |
| WO | WO2007127455 | 11/2007 |
| WO | WO2007127879 | 11/2007 |
| WO | WO2007128165 | 11/2007 |
| WO | WO2007130491 | 11/2007 |
| WO | WO2007143535 | 12/2007 |
| WO | WO2007149546 | 12/2007 |
| WO | WO2008002239 | 1/2008 |
| WO | WO2008008281 | 1/2008 |
| WO | WO2008030482 | 3/2008 |
| WO | WO2008052136 | 5/2008 |
| WO | WO2008063626 | 5/2008 |
| WO | WO2008066617 | 6/2008 |
| WO | WO2008068695 | 6/2008 |
| WO | WO2008076464 | 6/2008 |
| WO | WO2008089232 | 7/2008 |
| WO | WO2008091683 | 7/2008 |
| WO | WO2008095183 | 8/2008 |
| WO | WO2008097652 | 8/2008 |
| WO | WO2008101107 | 8/2008 |
| WO | WO2008112577 | 9/2008 |
| WO | WO2008112578 | 9/2008 |
| WO | WO2008120156 | 10/2008 |
| WO | WO2008133394 | 11/2008 |
| WO | WO2008134185 | 11/2008 |
| WO | WO2008150633 | 12/2008 |
| WO | WO2009001108 | 12/2008 |
| WO | WO2009006615 | 1/2009 |
| WO | WO2009029453 | 3/2009 |
| WO | WO2009031149 | 3/2009 |
| WO | WO2009035773 | 3/2009 |
| WO | WO2009036334 | 3/2009 |
| WO | WO2009051829 | 4/2009 |
| WO | WO2009051830 | 4/2009 |
| WO | WO2009063377 | 5/2009 |
| WO | WO2009081348 | 7/2009 |
| WO | WO2009111664 | 9/2009 |
| WO | WO2009146082 | 12/2009 |
| WO | WO2010003175 | 1/2010 |
| WO | WO2010009100 | 1/2010 |
| WO | WO2010011833 | 1/2010 |
| WO | WO2010019778 | 2/2010 |
| WO | WO2010057049 | 5/2010 |
| WO | WO2010075115 | 7/2010 |
| WO | WO2010080843 | 7/2010 |
| WO | WO2010105053 | 9/2010 |
| WO | WO2010107563 | 9/2010 |
| WO | WO2010115194 | 10/2010 |
| WO | WO2010132331 | 11/2010 |
| WO | WO2010135516 | 11/2010 |
| WO | WO2012104657 | 8/2012 |
| WO | WO2012112561 | 8/2012 |
| WO | WO2012158190 | 11/2012 |
| WO | WO2013012869 | 1/2013 |
| WO | WO2015042411 | 3/2015 |
| WO | WO2015044722 | 4/2015 |
| WO | WO2015112603 | 7/2015 |

OTHER PUBLICATIONS

Arshak et al., A Review and Adaptation of Methods of Object Tracking to Telemetry Capsules IC-Med (2007) vol. 1, No. 1, Issue 1, 12 pp.
"ASGE Technology Status Evaluation Report: wireless capsule endoscopy" American Soc. for Gastrointestinal Endoscopy (2006) vol. 63, No. 4; 7 pp.
Au-Yeung, K., et al., "A Networked System for Self-Management of Drug Therapy and Wellness", Wireless Health '10, Oct. 5-7, 2010, San Diego, 9 pages.
Aydin et al., "Design and implementation considerations for an advanced wireless interface in miniaturized integrated sensor Microsystems" Sch. of Eng. & Electron., Edinburgh Univ., UK; (2003); abstract.
Barrie, Heidelberg pH capsule gastric analysis. Texbook of Natural Medicine, (1992), Pizzorno, Murray & Barrie.
Baskiyar, S. "A Real-time Fault Tolerant Intra-body Network" Dept. of Comp. Sci & Soft Eng; Auburn University; Proceedings of the 27th Annual IEEE Conference; 0742-1303/02 (2002) IEEE; 6 pp.
Bergogne C., et al., "A new frequency estimator applied to burst transmission", IEEE International Conference on Acoustics, Speech and Signal Processing, Apr. 21, 1997, vol. 1, pp. 267-270.
Brock, "Smart Medicine: The Application of Auto-ID Technology to Healthcare" Auto-ID Labs (2002) http://www.autoidlabs.org/uploads/media/MIT-AUTOID-WH-010.pdf.
Carlson et al., "Evaluation of a non-invasive respiratory monitoring system for sleeping subjects" Physiological Measurement (1999) 20(1): 53.
Delvaux et al., "Capsule endoscopy: Technique and indications" Clinical Gastoenterology (2008) vol. 22, Issue 5, pp. 813-837.
Description of ePatch Technology Platform for ECG and EMG, located it http://www.madebydelta.com/imported/images/DELTA_Web/documents/ME/ePatch_ECG_EMG.pdf, Dated Sep. 2, 2010.
Evanczuk, S., "PIC MCU software library uses human body for secure communications link" EDN Network; edn.com; Feb. 26, 2013 Retrieved from internet Jun. 19, 2013 at http://www.edn.com/electronics-products/other/4407842/PIC-MCU-software-library-uses-human-body-for-secure-communications-link; 5 pp.

(56) References Cited

OTHER PUBLICATIONS

Fawaz et al., "Enhanced Telemetry System using CP-QPSK Band-Pass Modulation Technique Suitable for Smart Pill Medical Application" IFIP IEEE Dubai Conference (2008); http://www.asic.fh-offenburg.de/downloads/ePille/IFIP_IEEE_Dubai_Conference.pdf.
Gilson, D.R. "Molecular dynamics simulation of dipole interactions", Department of Physics, Hull University, Dec. 2002, p. 1-43.
Given Imaging, "Agile Patency Brochure" (2006) http://www.inclino.no/documents/AgilePatencyBrochure_Global_GMB-0118-01.pdf; 4pp.
Gonzalez-Guillaumin et al., "Ingestible capsule for impedance and pH monitoring in the esophagus" IEEE Trans Biomed Eng. (2007) 54(12: 2231-6; abstract.
Greene, "Edible RFID microchip monitor can tell if you take your medicine" Bloomberg Businessweek (2010) 2 pp.; http://www.businessweek.com/idg/2010-03-31/edible-rfid-microchip-monitor-can-tell-if-you-take-your-medicine.html.
Halthion Medical Technologies "Providing Ambulatory Medical Devices Which Monitor, Measure and Record" webpage. Online website: http://www.halthion.com/; downloaded May 30, 2012.
Heydari et al., "Analysis of the PLL jitter due to power/ground and substrate noise"; IEEE Transactions on Circuits and Systems (2004) 51(12): 2404-16.
Hoover et al., "Rx for health: Engineers design pill that signals it has been swallowed" University of Florida News (2010) 2pp.; http://news.ufl.edu/2010/03/31/antenna-pill-2/.
Hotz "The Really Smart Phone" The Wall Street Journal, What They Know (2011); 6 pp.; http://online.wsj.com/article/SB10001424052748704547604576263261679848814.html?mod=djemTECH_t.
Intromedic, MicroCam Innovative Capsule Endoscope Pamphlet. (2006) 8 pp (http://www.intromedic.com/en/product/productinfo.asp).
ISFET—Ion Sensitive Field-Effect Transistor; Microsens S.A. pdf document. First cited in Office Action dated Jun. 13, 2011 for U.S. Appl. No. 12/238,345; 4pp.
Jung, S. "Dissolvable 'Transient Electronics' Will Be Good for Your Body and the Environment" MedGadget; Oct. 1, 2012; Onlne website: http://medgadget.com/2012/10/dissolvable-transient-electronics-will-be-good-for-your-body-and-the-environment.html; downloaded Oct. 24, 2012; 4 pp.
Juvenile Diabetes Research Foundation International (JDRF), "Artificial Pancreas Project" (2010); http://www.artificialpancreasproject.com/; 3 pp.
Li, P-Y, et al. "An electrochemical intraocular drug delivery device", Sensors and Actuators A 143 (2008) p. 41-48.
Lifescan, "OneTouch UltraLink™" http://www.lifescan.com/products/meters/ultralink (2010) 2 pp.
Mackay et al., "Radio Telemetering from within the Body" Inside Information is Revealed by Tiny Transmitters that can be Swallowed or Implanted in Man or Animal Science (1991) 1196-1202; 134; American Association for the Advancement of Science, Washington D.C.
Mackay et al., "Endoradiosonde" Nature, (1957) 1239-1240, 179 Nature Publishing Group.
Mckenzie et al., "Validation of a new telemetric core temperature monitor" J. Therm. Biol. (2004) 29(7-8):605-11.
Medtronic, "CareLink Therapy Management Software for Diabetes" (2010); https://carelink.minimed.com/patient/entry.jsp?bhcp=1; 1 pp.
Medtronic, "Carelink™ USB" (2008) http://www.medtronicdiabetes.com/pdf/carelink_usb_factsheet.pdf 2pp.
Medtronic "The New MiniMed Paradigm® Real-Time Revel™ System" (2010) http://www.medtronicdiabetes.com/products/index.html; 2 pp.
Medtronic, "Mini Med Paradigm® Revel™ Insulin Pump" (2010) http://www.medtronicdiabetes.com/products/insulinpumps/index.html; 2 pp.
Medtronic, Mini Med Paradigm™ Veo™ System: Factsheet (2010). http://www.medtronic-diabetes.com.au/downloads/Paradigm%20Veo%20Factsheet.pdf ; 4 pp.

Melanson, "Walkers swallow RFID pills for science" Engadget (2008); http://www.engadget.com/2008/07/29/walkers-swallow-rfid-pills-for-science/.
Minimitter Co. Inc. "Actiheart" Traditional 510(k) Summary. Sep. 27, 2005.
Minimitter Co. Inc. Noninvasive technology to help your studies succeed. Mini Mitter.com Mar. 31, 2009.
Mini Mitter Co, Inc. 510(k) Premarket Notification Mini-Logger for Diagnostic Spirometer. 9-21 (1999).
Mini Mitter Co, Inc. 510(k) Premarket Notification for VitalSense. Apr. 22, 2004.
Minimitter Co. Inc. VitalSense Integrated Physiological Monitoring System. Product Description. (2005).
Minimitter Co. Inc. VitalSense Wireless Vital Signs Monitoring. Temperatures.com Mar. 31, 2009.
Mojaverian et al., "Estimation of gastric residence time of the Heidelberg capsule in humans: effect of varying food composition" Gastroenterology (1985) 89:(2): 392-7.
"New 'smart pill' to track adherence" E-Health-Insider (2010) http://www.e-health-insider.com/news/5910/new_'smart_pill'_monitors_medicines.
Owano, N., "Study proposes smart sutures with sensors for wounds" phys.org. Aug. 2012. http://phys.org/news/2012-08-smart-sutures-sensors-wounds.html.
Park, "Medtronic to Buy MiniMed for $3.7 Billion" (2001) HomeCare; http://homecaremag.com/mag/medical_medtronic_buy_minimed/; 2 pp.
Radio Antennae, http://www.erikdeman.de/html/sail018h.htm; (2008) 5 pages.
"RFID "pill" monitors marchers" RFID News (2008) http://www.rfidnews.org/2008/07/23/rfid-pill-monitors-marchers/.
Sanduleanu et al., "Octave tunable, highly linear, RC-ring oscillator with differential fine-coarse tuning, quadrature outputs and amplitude control for fiber optic transceivers" (2002) IEEE MTT-S International Microwave Symposium Digest 545-8.
Santini, J.T. et al, "Microchips as controlled drug delivery-devices", Agnew. Chem. Int. Ed. (2000), vol. 39, p. 2396-2407.
"SensiVida minimally invasive clinical systems" Investor Presentation Oct. 2009 28pp; http://www.sensividamedtech.com/SensiVidaGeneralOctober09.pdf.
Shawgo, R.S. et al. "BioMEMS from drug delivery", Current Opinion in Solid State and Material Science 6 (2002), p. 329-334.
Shrivas et al., "A New Platform for Bioelectronics-Electronic Pill", Cummins College, (2010).; http://www.cumminscollege.org/downloads/electronics_and_telecommunication/Newsletters/Current%20Newsletters.pdf; First cited in third party client search conducted by Patent Eagle Search May 18, 2010 (2010).
"Smartlife awarded patent for knitted transducer" Innovation in Textiles News: http://www.innovationintextiles.com/articles/208.php; 2pp. (2009).
"The SmartPill Wireless Motility Capsule" SmartPill, The Measure of GI Health; (2010) http://www.smartpillcorp.com/index.cfm?pagepath=Products/The_SmartPill_Capsule&id=17814.
Solanas et al., "RFID Technology for the Health Care Sector" Recent Patents on Electrical Engineering (2008) 1, 22-31.
Soper, S.A. et al. "Bio-Mems Technologies and Applications", Chapter 12, "MEMS for Drug Delivery", p. 325-346 (2007).
Swedberg, "University Team Sees Ingestible RFID Tag as a Boon to Clinical Trials" RFID Journal Apr. 27, 2010; http://www.rfidjournal.com/article/view/7560/1.
Tajalli et al., "Improving the power-delay performance in subthreshold source-coupled logic circuits" Integrated Circuit and System Design. Power and Timing Modeling, Optimization and Simulation, Springer Berlin Heidelberg (2008) 21-30.
Tatbul et al., "Confidence-based data management for personal area sensor networks" ACM International Conference Proceeding Series (2004) 72.
Tierney, M.J. et al "Electroreleasing Composite Membranes for Delivery of Insulin and other Biomacromolecules", J. Electrochem. Soc., vol. 137, No. 6, Jun. 1990, p. 2005-2006.
Walkey, "MOSFET Structure and Processing"; 97.398* Physical Electronics Lecture 20, 24 pages, First cited in Office Action dated Jun. 13, 2011 for U.S. Appl. No. 12/238,345.

(56) References Cited

OTHER PUBLICATIONS

Xiaoming et al., "A telemedicine system for wireless home healthcare based on bluetooth and the internet" Telemedicine Journal and e-health (2004) 10(S2): S110-6.
Yang et al., "Fast-switching frequency synthesizer with a discriminator-aided phase detector" IEEE Journal of Solid-State Circuits (2000) 35(10): 1445-52.
Yao et al., "Low Power Digital Communication in Implantable Devices Using Volume Conduction of Biological Tissues" Proceedings of the 28th IEEE, EMBS Annual International Conference, Aug. 30-Sep. 3, 2006.
Zimmerman, "Personal Area Networks: Near-field intrabody communication" IBM Systems Journal (1996) 35 (3-4):609-17.
Zworykin, "A Radio Pill" Nature, (1957) 898, 179 Nature Publishing Group.
Kang et al., "Nonwoven Fabric Active Electrodes for Biopotential Measurement During Normal Daily Activity," IEEE Trans Biomed Eng. Jan. 2008; vol. 55, No. 1, pp. 188-195.

\* cited by examiner

PERSONAL AUTHENTICATION APPARATUS SYSTEM AND METHOD

CROSS-REFERENCE TO RELATED APPLICATIONS

This application is a continuation application claiming priority under 35 U.S.C. § 120 to U.S. patent application Ser. No. 13/843,307, entitled PERSONAL AUTHENTICATION APPARATUS SYSTEM AND METHOD, filed Mar. 15, 2013, now U.S. Pat. No. 9,659,423, the entire disclosure of which is hereby incorporated by reference herein.

INTRODUCTION

The present disclosure is related generally to authentication and/or passing value tokens, the process of confirming the identity of a person by verifying the validity of at least one form of identification by a target authentication device. More particularly, the present disclosure is related to employing personal authentication techniques to authenticate users of the target authentication device.

Conventional modes of authentication include the use of passwords generally composed of character strings composed of letters (a, b, c, . . . ), numbers (1, 2, 3, . . . ), and/or symbols (!, @, #, . . . ) arranged in various combinations.

A minimum level of security for accessing a target authentication device such as a mobile phone is achieved by requiring the owner/user of the mobile phone to enter a unique four-digit character string referred to generally as a Personal Identification Code (PIN), and a passcode in the case of the iPhone brand of mobile phones. The amount of time a mobile phone allows access before requiring re-entry of the PIN is configurable depending on the desired level of security of the owner. Entering a PIN/passcode, however, is a frequent burden for the owner. The owner may be required to enter a PIN/passcode several times per hour throughout the day, every day. In addition to being burdensome for the user, such minimum levels of security are easily hacked by someone skilled in exploiting weaknesses of computer systems.

More generally, however, ways in which someone may be authenticated fall into three categories, based on what are known as the factors of authentication: something the user knows, something the user has, and something the user is. Each authentication factor covers a range of elements used to authenticate or verify a person's identity prior to being granted access, approving a transaction request, signing a document or other work product, granting authority to others, and establishing a chain of authority. For a positive authentication, elements from at least two, and preferably all three, factors should be verified. The three factors (classes) and some of elements of each factor are: the ownership factors: Something the user has (e.g., wrist band, ID card, security token, software token, phone, or cell phone) the knowledge factors: Something the user knows (e.g., a password, pass phrase, or personal identification number (PIN), challenge response (the user must answer a question), pattern) the inherence factors: Something the user is or does (e.g., fingerprint, retinal pattern, DNA sequence (there are assorted definitions of what is sufficient), signature, face, voice, unique bio-electric signals, or other biometric identifier).

Two-factor authentication is when elements representing two factors are required for authentication, the term two-factor authentication is applied—e.g., a bankcard (something the user has) and a PIN (something the user knows). Business networks may require users to provide a password (knowledge factor) and a pseudorandom number from a security token (ownership factor). Access to a very-high-security system might require a mantrap screening of height, weight, facial, and fingerprint checks (several inherence factor elements) plus a PIN and a day code (knowledge factor elements), but this is still a two-factor authentication.

Conventional modes of authentication have become increasingly burdensome and inadequate means for security. Accordingly, new authentication approaches that are robust and less burdensome are needed.

SUMMARY

In one aspect, a target authentication device is provided. The target authentication device comprises at least one electrode configured to detect an electrical signal associated with a user of the target authentication device. The electrical signal represents an authentication code for the target authentication device. An authentication receiver module is coupled to the at least one electrode. The authentication receiver module is configured to receive the electrical signal from the at least one electrode and to determine whether the electrical signal matches a predetermined criteria to authenticate the identity of the user based on the electrical signal.

In another aspect, an authentication module is provided. The authentication module comprises at least one electrode configured to couple an electrical signal associated with a user to a user of a target authentication device, the electrical signal represents an authentication code for the target authentication device. An authentication transmission module is coupled to the at least one electrode. The authentication transmission module is configured to transmit the electrical signal from the at least one electrode.

In yet another aspect, a method of authenticating the identity of a user of a target authentication device is provided. According to the method, at least one electrode detects an electrical signal associated with a user of the target authentication device, the electrical signal representing an authentication code for the target authentication device. An authentication receiver module coupled to the at least one electrode receives the electrical signal from the at least one electrode. A processor determines whether the electrical signal matches a predetermined criterion to authenticate the identity of the user based on the electrical signal.

FIGURES

FIG. 11A shows an exploded view of the surface of dissimilar materials of FIG. 11.

Figure 17:
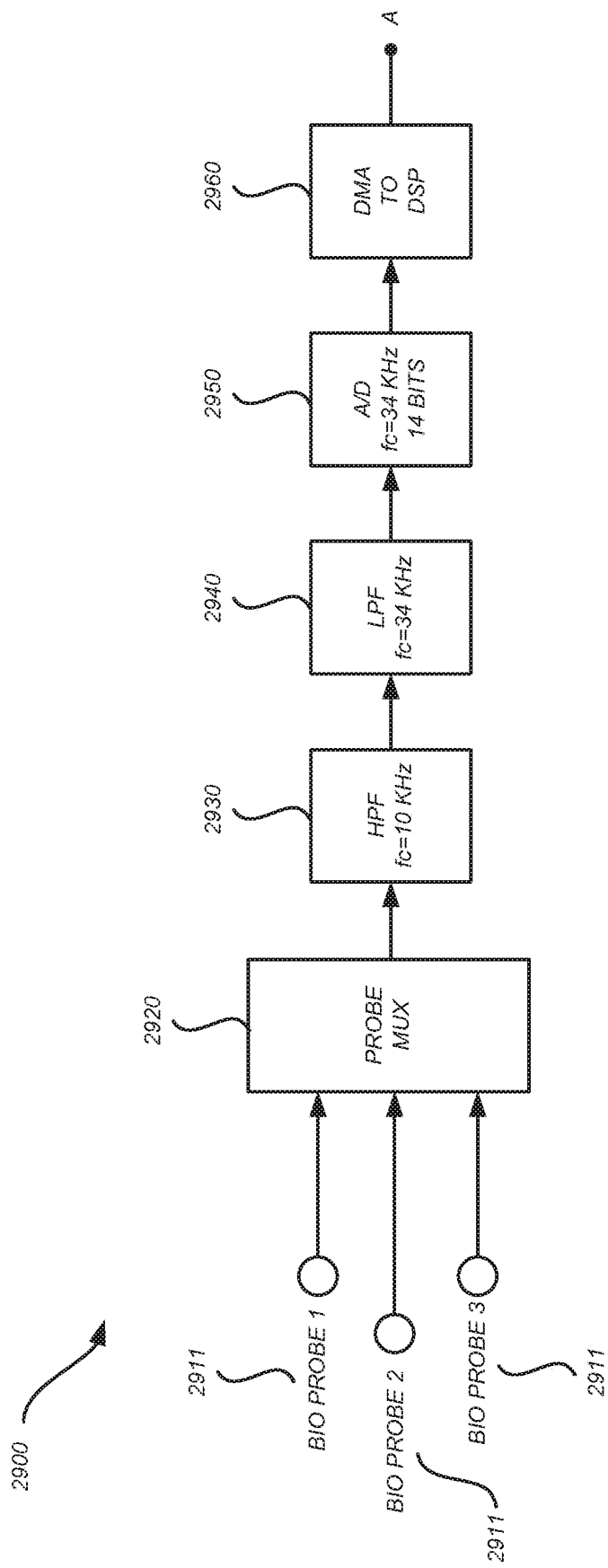

FIG. 17 provides a block diagram of a high frequency signal chain in a receiver, according to one aspect.

Figure 18A:
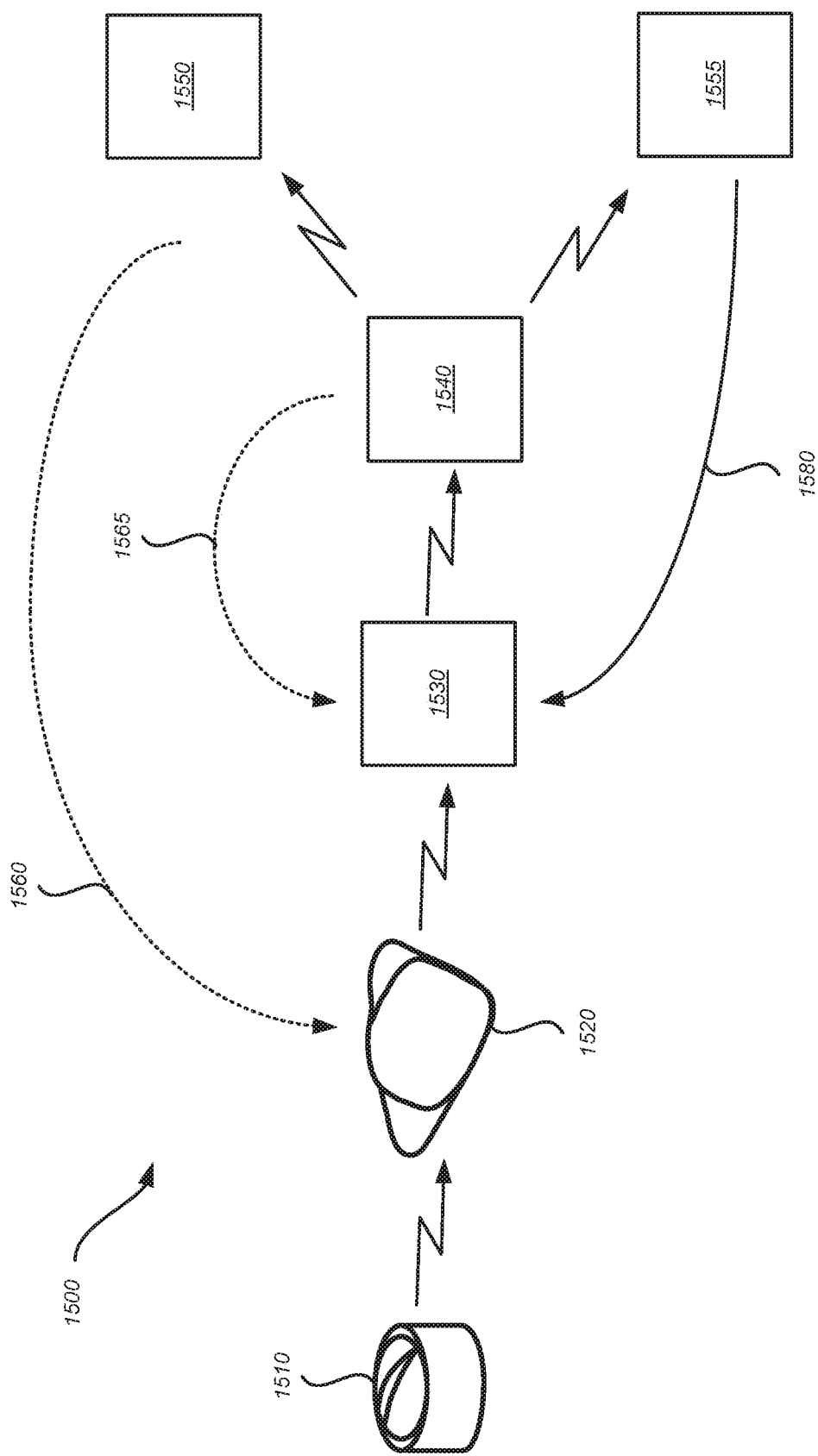

FIG. 18A provides a diagram of how a system that includes a signal receiver and an ingestible event marker may be employed, according to one aspect.

Figure 18B:
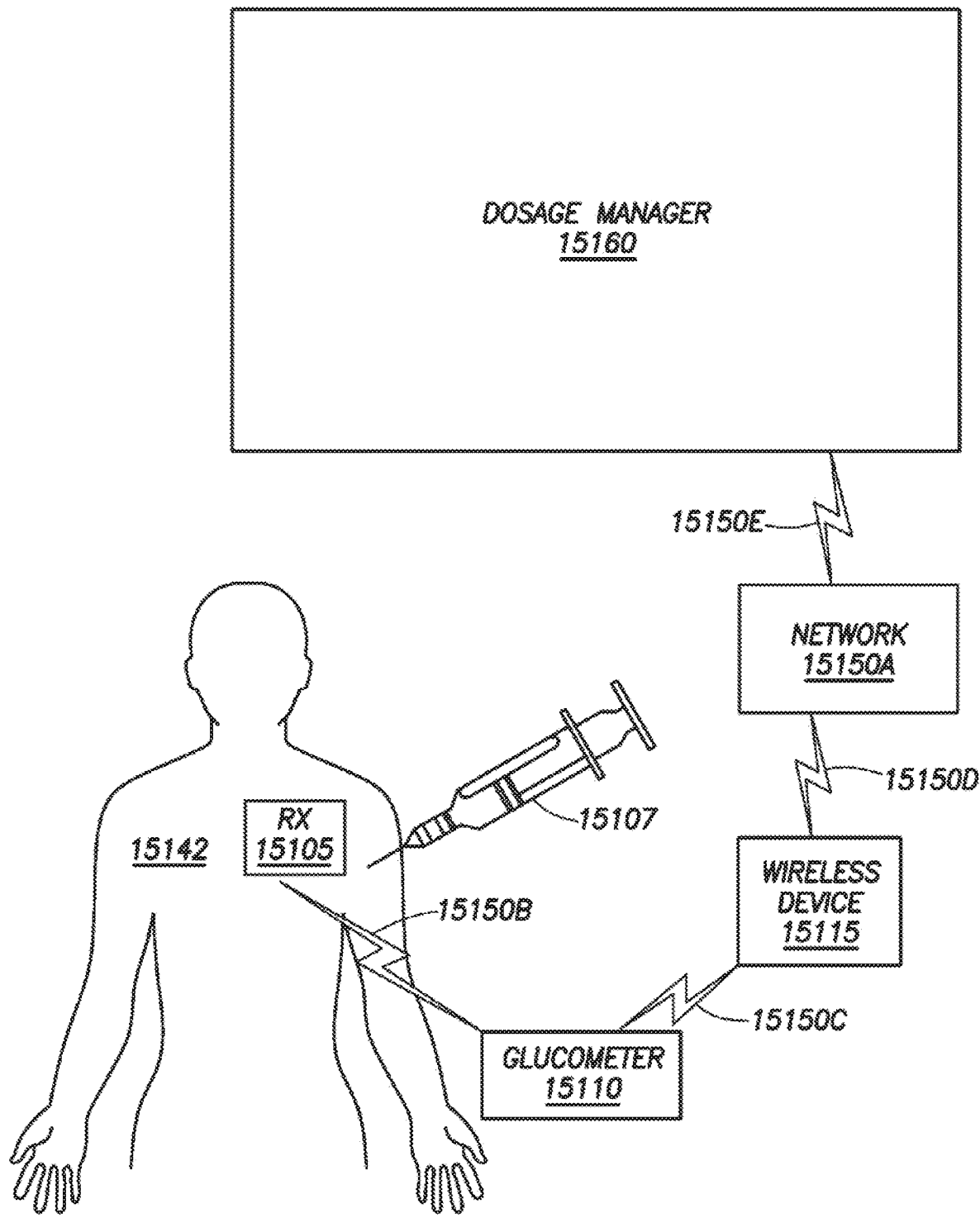

FIG. 18B provides a pharmaceutical delivery system that receives control information form a receiver and control the dosage delivery.

Figure 19:
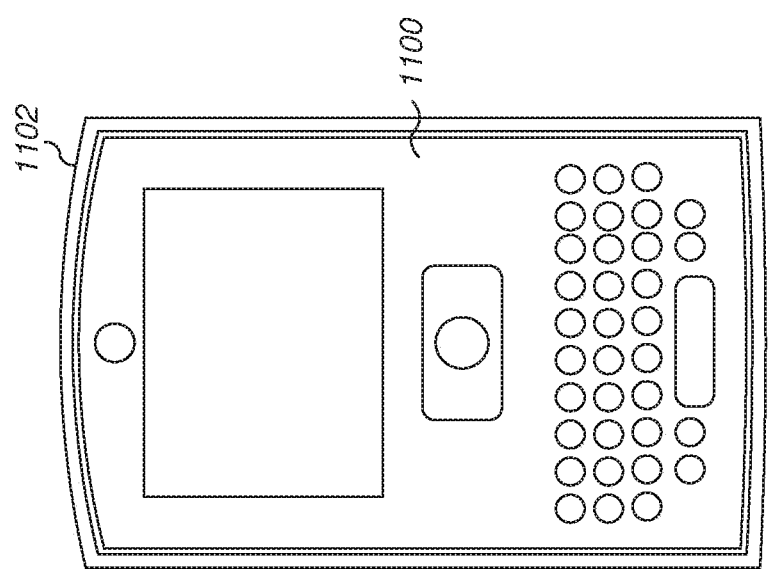

FIG. 19 illustrates one aspect of mobile device received in a mating configuration with a mobile device enclosing arrangement comprising a detection circuit integrated therewith for detecting an electrical signal generated by an ingestible event marker.

Figure 20:
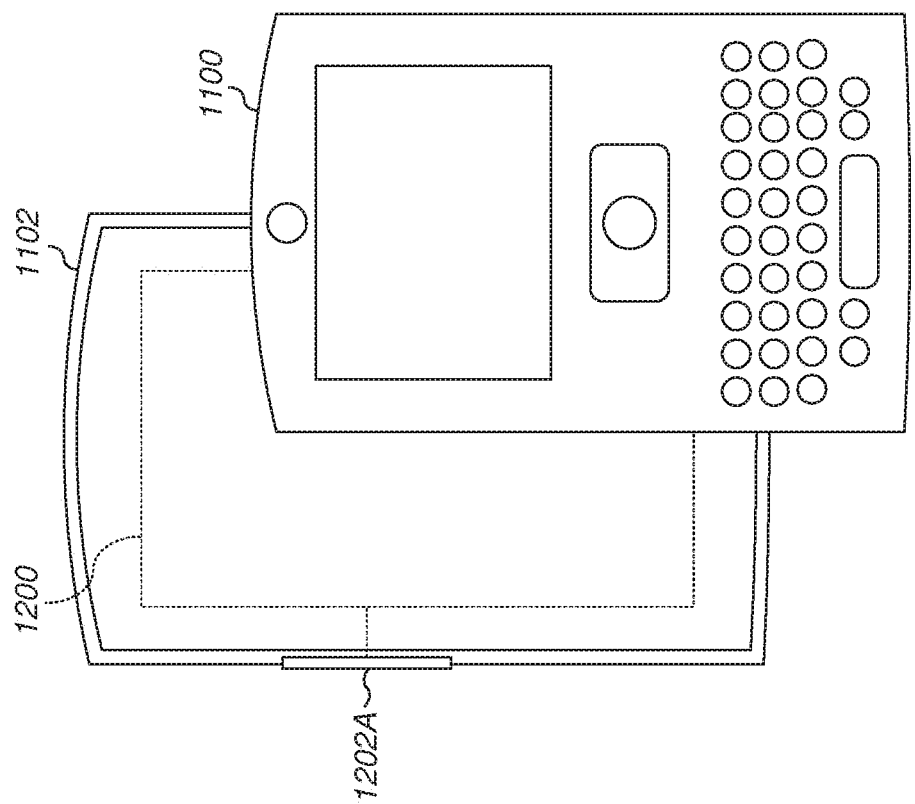

FIG. 20 illustrates the mobile device and the housing for receiving the mobile device shown in FIG. 19 in an unmated configuration.

Figure 21:
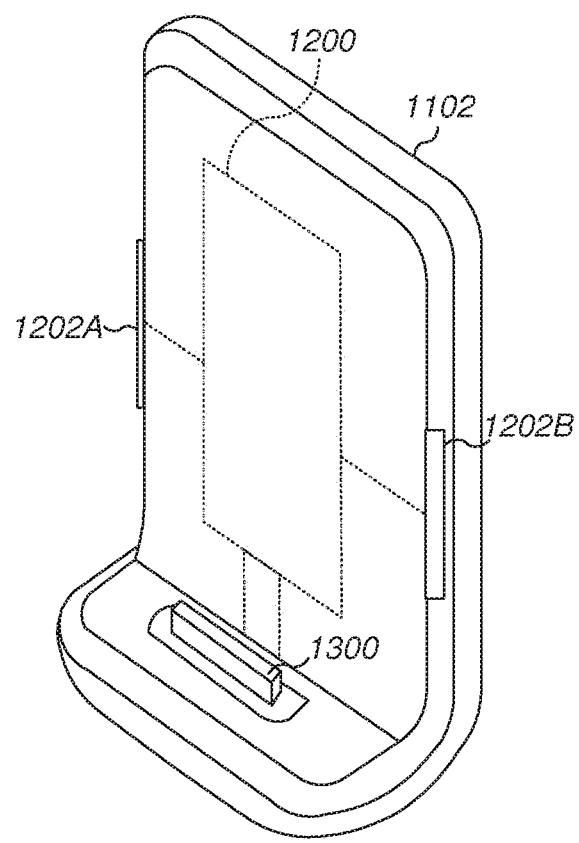

FIG. 21 illustrates one aspect of a housing for receiving a mobile device where the housing comprises a detection circuit for detecting an electrical signal generated by an ingestible event marker integrated therewith and a connector for electrically coupling the detection circuit to the functional modules of the mobile device.

DESCRIPTION

Before explaining the various aspects of authentication in detail, it should be noted that the various aspects disclosed herein are not limited in their application or use to the details of construction and arrangement of parts illustrated in the accompanying drawings and description. Rather, any disclosed aspect of authentication may be positioned or incorporated in other aspects of authentication, variations, and modifications thereof, and may be practiced or carried out in various ways. Accordingly, aspects of the authentication apparatus, system, and method disclosed herein are illustrative in nature and are not meant to limit the scope or application thereof. Furthermore, unless otherwise indicated, the terms and expressions employed herein have been chosen for the purpose of describing the aspects for the convenience of the reader and are not to limit the scope thereof. In addition, it should be understood that any one or more of the disclosed aspects, expressions of aspects, and/or examples thereof, can be combined with any one or more of the other disclosed aspects, expressions of aspects, and/or examples thereof, without limitation.

In the following description, like reference characters designate like or corresponding parts throughout the several views. Also, in the following description, it is to be understood that terms such as front, back, inside, outside, top, bottom and the like are words of convenience and are not to be construed as limiting terms. Terminology used herein is not meant to be limiting insofar as devices described herein, or portions thereof, may be attached or utilized in other orientations. The various aspects will be described in more detail with reference to the drawings.

The present disclosure is directed generally to various aspects of authentication by providing a physical connection between a user and a target authentication device. One example of a target authentication device is a computer system. As used herein, the term computer system in intended to encompass a broad category of devices including, without limitation, computer networks, desktop computers, laptop computers, notebook computers, tablet computers, tablet computers, mobile phones, personal digital assistants, appliances, positioning systems, media devices, automatic teller machines (ATM), kiosks, and the like. In addition, authentication is required when entering public modes of transportation (bus, train, subway, airplane, boat, rental car), building entrances, stadiums, turnstiles, and the like. Additional computer systems that may require authentication also may include medical systems that dispense medication in any form.

It will be appreciated that the term "medication" or "dose form" as used throughout this disclosure includes various forms of ingestible, inhalable, injectable, absorbable, or otherwise consumable medicaments and/or carriers therefor such as, for example, pills, capsules, gel caps, placebos, over capsulation carriers or vehicles, herbal, over-the-counter (OTC) substances, supplements, prescription-only medication, ingestible event markers (IEM), and the like.

Figure 1:
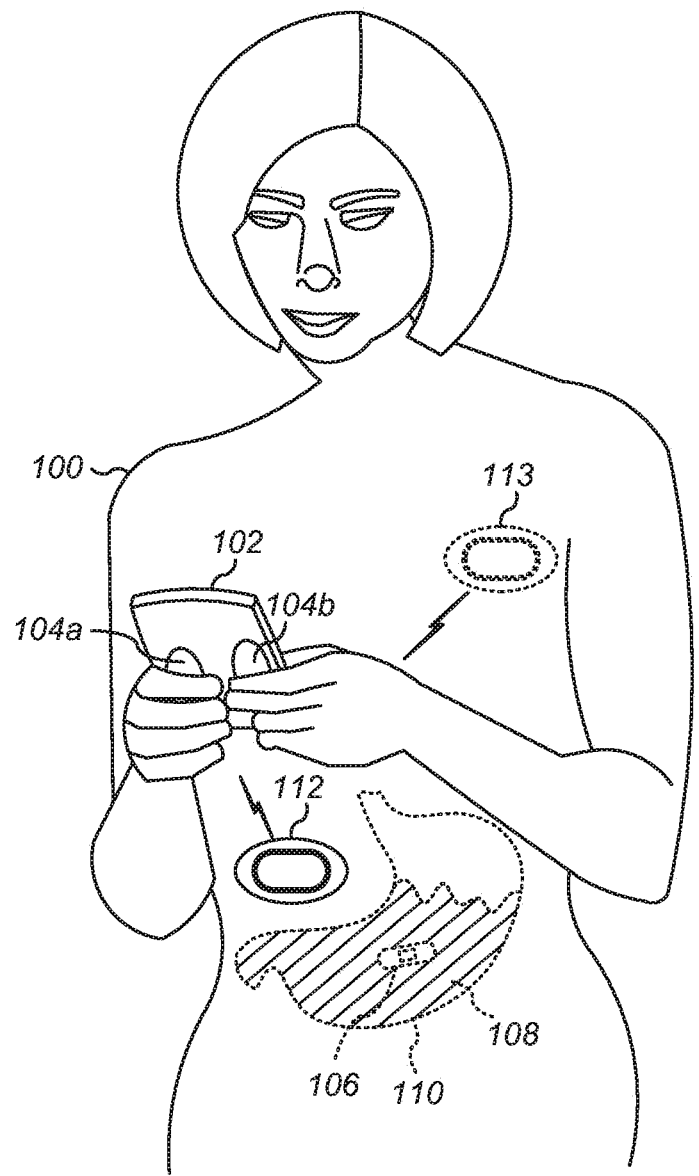
FIG. 1 illustrates a subject using a mobile device comprising electrodes for detecting personal electrical signals from the body of the subject.

Prior to describing various aspects of authentication techniques, the present disclosure first turns to FIG. 1 for a brief description of one aspect of a system employing a sensing subsystem coupled to a subject, an event indicator system, and/or a body associated device by way of at least one electrode. A subject can be person or thing that is requesting access to a target authentication device. The body associated device and the event indicator system are configured to generate a unique electrical current signal that is detectable by a detection subsystem. In addition, the detection subsystem may be configured to detect various physiological parameters associated with a living subject.

FIG. 1 illustrates a subject 100 using a mobile device 102 comprising electrodes 104a, 104b for detecting personal electrical signals conducted through the body of the subject 100. In the illustrated example, the mobile device 102 is the target authentication device. The mobile device 102 comprises electrodes 104a, 104b integrated into the housing for detecting electrical signals coupled from the subject 100 to the electrodes 104a, 104b. The term personal electrical signal is used to indicate that a signal is intimately associated with the subject 100 such that it can be used to confirm the identity of the subject 100 for purposes of authentication. Personal electrical signals include, without limitation, physiological signals associated with the subject, transbody conductive signals generated by an ingestible event marker system 106, transbody conductive signals generated by a body-associated device 112, e.g., an adhesive patch that is applied on the body of the subject 100, any object in physical contact with the subject for example watch, bracelet, necklace, ring, etc. and/or transbody conductive signals generated by an implanted body-associated device 113 that is located within the body of the subject 100. Physiological signals include, without limitation, skin impedance, electro cardiogram signals, conductively transmitted current signal, position of wearer, temperature, heart rate, perspiration rate, humidity, altitude/pressure, global positioning system (GPS), proximity, bacteria levels, glucose level, chemical markers, blood oxygen levels, among other physiological and physical parameters. Transbody conductive signals include, without limitation, electrical currents that are transmitted through the body of a subject, where the body acts as the conduction medium. In one aspect, transbody conductive signals can be generated by an ingestible event marker system 106, one example of which is described in connection with FIG. 5. In other aspects, transbody conductive signals can be generated by electrical circuits placed in electrical contact with the surface of the skin of the subject 100 by way of a body-associated device 112. In other aspects, transbody conductive signals can be generated by electrical circuits implanted within the body of the subject 100. Additional aspects of mobile devices 102 configured for detecting an electrical signal from an ingestible event marker system 106, among others, are described in commonly assigned International PCT Application PCT/US/2012/047076, international publication number WO 2013/012869, which is herein incorporated by reference in its entirety.

Regardless of the source, the unique electrical signals suitable for authentication are coupled to the target authentication device, e.g., the mobile device 102, through at least one of the electrodes 104a, 104b, which are suitable for sensing and sourcing electrical signals. In operation, the subject 100 holds the mobile device 102, or otherwise contacts electrodes on another type of computer system, and physically contacts at least one of the electrodes 104a, 104b. The electrical signals are coupled from the subject 100 through at least one of the electrodes 104a, 104b to an authentication subsystem. The authentication subsystem can be integrated with the mobile device 102 or may be added on.

When the ingestible event marker system 106 is the signal source, a unique electrical current signal is generated when the ingestible event marker system 106 contacts digestive fluids 108 in the stomach 110 of the subject 100. The unique electrical current signature is conducted through the body of the subject 100, is detected by at least one of the electrodes 104a, 104b, and is coupled to an authentication subsystem, which decodes the signal and provides a decoded signal to a processing subsystem to authenticate the subject 100.

When the body associated device 112 is the signal source, an electrical current signal is generated by circuits in the body associated device 112. The body associated device 112 is electrically coupled to the body of the subject 100 by another set of electrodes. The electrical signal is conducted by the body and detected by at least one of the input electrodes 104a, 104b on the mobile device 102. These and other aspects of the personal authentication techniques are discussed hereinbelow. Prior to describing such systems, however, the disclosure now turns to measurement subsystems for detecting electrical signals.

Figure 2:
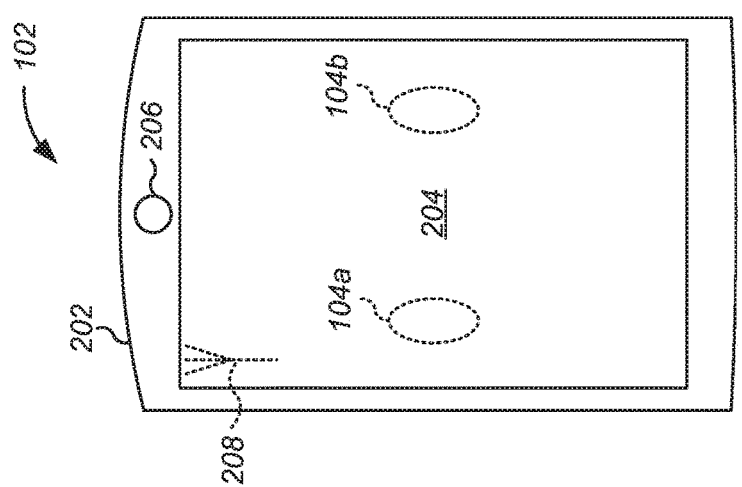
FIG. 2 illustrates one aspect of a mobile device comprising electrodes for detecting electrical signals that can be employed to authenticate the identity of the subject to enable the subject to get access to the mobile device.

FIG. 2 illustrates one aspect of a mobile device 102 comprising electrodes 104a, 104b for detecting personal electrical signals suitable for authenticating the identity of the subject 100. The mobile device 102 also comprises a housing 202, a display 204, an aperture 206 for capturing digital images, and an antenna 208. The electrodes 104a, 104b are located on the back of the housing 202 or at any convenient location of the mobile device 102. In one aspect, for example, the electrodes 104a, 104b may be located on or embedded within a skin or design cover for a mobile device 102 as described hereinbelow in connection with FIGS. 19-21.

Figure 3:
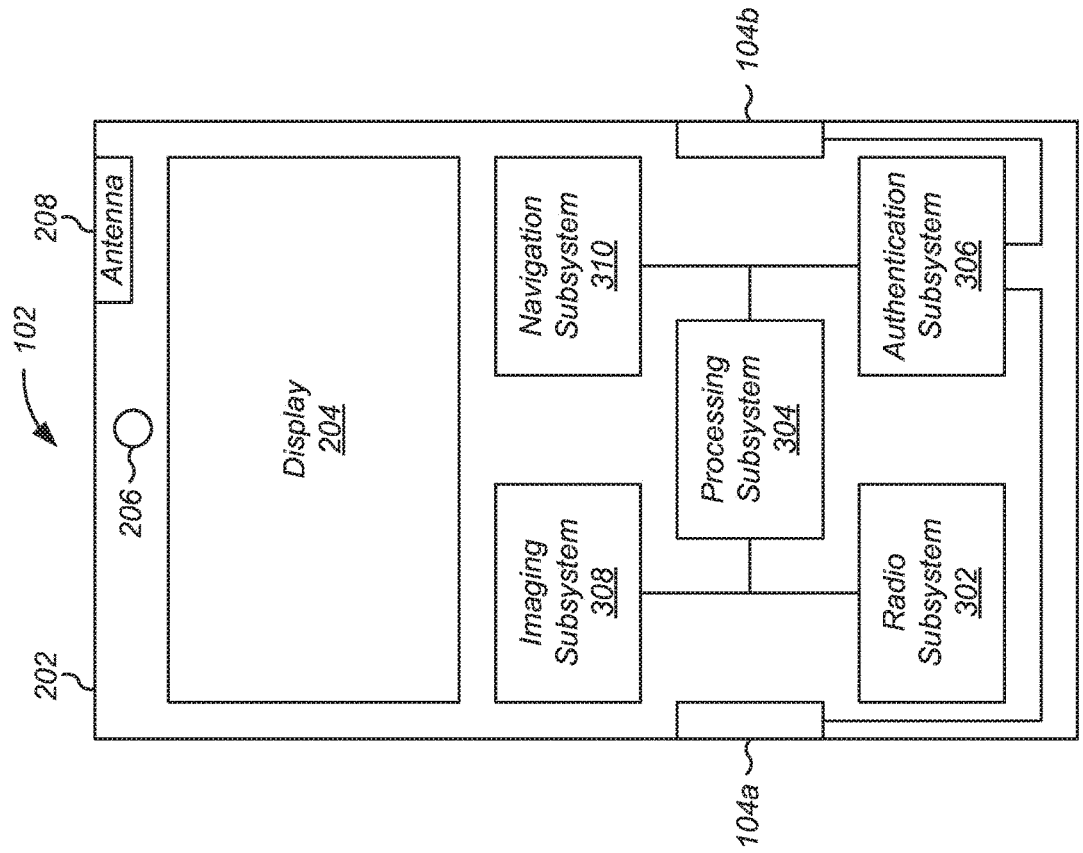
FIG. 3 is system diagram of one aspect of a mobile device configured to detect electrical signals for authenticating the identity of the subject.

FIG. 3 is a diagram of one aspect of a mobile device 102 configured for detecting electrical signals for authenticating the identity of a subject 100. The mobile device 102 may comprise multiple elements. Although FIG. 3 shows a limited number of elements in a certain topology by way of example, it can be appreciated that additional or fewer elements in any suitable topology may be used in the mobile device 102 as desired for a given implementation. Furthermore, any element as described herein may be implemented using hardware, software, or a combination of both, as previously described with reference to node implementations. Aspects of the mobile device 102, however, are not limited in this context.

In various aspects, in addition to a housing 202, a display 204, an aperture 206 for capturing digital images, and an antenna 208, the mobile device 102 comprises a radio subsystem 302 connected via a bus to a processing subsystem 304. The radio subsystem 302 may perform voice and data communications operations using wireless shared media for the mobile device 102. The processing subsystem 304 may execute software for the mobile device 102. A bus may comprise a USB or micro-USB bus and appropriate interfaces, as well as others.

In various aspects, an authentication and/or protection subsystem 306 is coupled to the electrodes 104a, 104b. The electrodes 104a, 104b are configured to be in physical contact with the subject 100 (FIG. 1) to electrically couple the unique electrical signals to and from the authentication subsystem 306. When the subject 100 physically contacts at least one of the electrodes 104a, 104b the authentication subsystem 306 can receive or transmit a unique electrical current signal for authenticating the identity of the subject 100 and, once authenticated, providing access to the mobile device 102. Also, when the authentication subsystem 306 detects physiological signals associated with the subject 100, the authentication subsystem 306 builds a database, which over time provides an average of the physiological signals associated with the subject 100. Authentication occurs only when the detected physiological signals match the running average physiological signals stored in the database.

In various aspects, the detection subsystem 306 is coupled to the processing subsystem 304. The detection subsystem 306 converts the detected electrical signals into a secret word or string of characters. A processing subsystem 304 coupled to the detection subsystem 306 uses the string of characters for user authentication to prove identity of the subject 100 (FIG. 1) or for access approval to gain access to the mobile device 102. When the subject 100 is authenticated, the processing subsystem 304 activates the radio subsystem 304 and other functional modules of the computing device 102, such as, for example, an imaging subsystem 308 or a navigation subsystem 310. When the subject 100 is not authenticated, the processing subsystem 304 denies access to the functional modules of the mobile device 102 until the proper electrical signals are detected by the detection subsystem 306.

In various aspects, the display 204 may comprise any suitable display unit for displaying information appropriate for a mobile device 102. The I/O system may comprise any suitable I/O device for entering information into the mobile device 102. Examples for the I/O system may include an alphanumeric keyboard, a numeric keypad, a touch pad, a capacitive touch screen panel, input keys, buttons, switches, rocker switches, voice recognition device and software, and so forth. The I/O system may comprise a microphone and speaker, for example. Information also may be entered into the mobile device 102 by way of the microphone. Such information may be digitized by a voice recognition device.

In various aspects, the radio subsystem 320 may perform voice and data communications operations using wireless shared media for the mobile device 102. The processing subsystem 304 may execute software for the mobile device 102. A bus may comprise a universal serial bus (USB), micro-USB bus, dataport, and appropriate interfaces, as well as others. In one aspect the radio subsystem 302 may be arranged to communicate voice information and control information over one or more assigned frequency bands of the wireless shared media.

In various aspects, the imaging subsystem 308 processes images captured through the aperture 206. A camera may be coupled (e.g., wired or wirelessly) to the processing subsystem 304 and is configured to output image data (photographic data of a person or thing, e.g., video data, digital still image data) to the processing subsystem 304 and to the display 204. In one aspect, the imaging subsystem 308 may comprise a digital camera implemented as an electronic device used to capture and store images electronically in a digital format. Additionally, in some aspects the digital camera may be capable of recording sound and/or video in addition to still images.

In various aspects, the imaging subsystem 308 may comprise a controller to provide control signals to components of a digital camera, including lens position component, microphone position component, and a flash control module, to provide functionality for the digital camera. In some aspects, the controller may be implemented as, for example, a host processor element of the processing subsystem 304 of the mobile device 102. Alternatively, the imaging controller may be implemented as a separate processor from the host processor.

In various aspects, the imaging subsystem 308 may comprise memory either as an element of the processing subsystem 304 of the mobile device 102 or as a separate element. It is worthy to note that in various aspects some portion or the entire memory may be included on the same integrated circuit as the controller. Alternatively, some portion or the entire memory may be disposed on an integrated circuit or other medium (e.g., hard disk drive) external to the integrated circuit of the controller.

In various aspects, the aperture 206 includes a lens component and a lens position component. The lens component may consist of a photographic or optical lens or arrangement of lenses made of a transparent material such as glass, plastic, acrylic or Plexiglass, for example. In one aspect, the one or more lens elements of the lens component may reproduce an image of an object and allow for zooming in or out on the object by mechanically changing the focal length of the lens elements. In various aspects, a digital zoom may be employed in the imaging subsystem 308 to zoom in or out on an image. In some aspects, the one or more lens elements may be used to focus on different portions of an image by varying the focal length of the lens elements. The desired focus can be obtained with an autofocus feature of the digital imaging subsystem 308 or by manually focusing on the desired portion of the image, for example.

In various aspects, the navigation subsystem 310 supports navigation using the mobile device 102. In various aspects the mobile device 102 may comprise location or position determination capabilities and may employ one or more location determination techniques including, for example, Global Positioning System (GPS) techniques, Cell Global Identity (CGI) techniques, CGI including timing advance (TA) techniques, Enhanced Forward Link Trilateration (EFLT) techniques, Time Difference of Arrival (TDOA) techniques, Angle of Arrival (AOA) techniques, Advanced Forward Link Trilateration (AFTL) techniques, Observed Time Difference of Arrival (OTDOA), Enhanced Observed Time Difference (EOTD) techniques, Assisted GPS (AGPS) techniques, hybrid techniques (e.g., GPS/CGI, AGPS/CGI, GPS/AFTL or AGPS/AFTL for CDMA networks, GPS/EOTD or AGPS/EOTD for GSM/GPRS networks, GPS/OTDOA or AGPS/OTDOA for UMTS networks), among others.

In various aspects, the mobile device 102 may be configured to operate in one or more location determination modes including, for example, a standalone mode, a mobile station (MS) assisted mode, and/or a MS-based mode. In a standalone mode, such as a standalone GPS mode, the mobile device 102 may be configured to determine its position without receiving wireless navigation data from the network, though it may receive certain types of position assist data, such as almanac, ephemeris, and coarse data. In a standalone mode, the mobile device 102 may comprise a local location determination circuit such as a GPS receiver which may be integrated within the housing 202 configured to receive satellite data via the antenna 208 and to calculate a position fix. Local location determination circuit may alternatively comprise a GPS receiver in a second housing separate from the housing 202 but in the vicinity of the mobile device 102 and configured to communicate with the mobile device 102 wirelessly (e.g., via a PAN, such as Bluetooth). When operating in an MS-assisted mode or an MS-based mode, however, the mobile device 102 may be configured to communicate over a radio access network (e.g., UMTS radio access network) with a remote computer (e.g., a location determination entity (LDE), a location proxy server (LPS) and/or a mobile positioning center (MPC), among others).

In various aspects, the mobile device 102 also may comprise a power management subsystem (not shown) to manage power for the mobile device 102, including the radio subsystem 302, the processing subsystem 304, and other elements of the mobile device 102. For example, the power management subsystem may include one or more batteries to provide direct current (DC) power, and one or more alternating current (AC) interfaces to draw power from a standard AC main power supply.

In various aspects, the radio subsystem 302 may include an antenna 208. The antenna 208 may broadcast and receive RF energy over the wireless shared media. Examples for the antenna 208 may include an internal antenna, an omnidirectional antenna, a monopole antenna, a dipole antenna, an end fed antenna, a circularly polarized antenna, a microstrip antenna, a diversity antenna, a dual antenna, an antenna array, a helical antenna, and so forth. The aspects are not limited in this context.

In various aspects, the antenna 208 may be connected to a multiplexer. The multiplexer multiplexes signals from a power amplifier for delivery to the antenna 208. The multiplexer demultiplexes signals received from the antenna for delivery to an RF chipset.

In various aspects, the multiplexer may be connected to a power amplifier, where the power amplifier may be used to amplify any signals to be transmitted over the wireless shared media. The power amplifier may work in all assigned frequency bands, such as four (4) frequency bands in a quad-band system. The power amplifier also may operate in various modulation modes, such as Gaussian Minimum Shift Keying (GMSK) modulation suitable for GSM systems and 8-ary Phase Shift Keying (8-PSK) modulation suitable for EDGE systems.

In various aspects, the power amplifier may be connected to an RF chipset. The RF chipset also may be connected to the multiplexer. In one aspect, the RF chipset may comprise an RF driver and an RF transceiver. The RF chipset performs all of the modulation and direct conversion operations required for GMSK and 8-PSK signal types for quad-band E-GPRS radio. The RF chipset receives analog in-phase (I) and quadrature (Q) signals from a baseband processor, and converts the I/Q signals to an RF signal suitable for amplification by the power amplifier. Similarly, the RF chipset converts the signals received from the wireless shared media via the antenna 208 and the multiplexer to analog I/Q signals to be sent to the baseband processor. Although the RF chipset may use two chips by way of example, it may be appreciated that the RF chipset may be implemented using more or less chips and still fall within the intended scope of the aspects.

In various aspects, the RF chipset may be connected to the baseband processor, where the baseband processor may perform baseband operations for the radio subsystem 514. The baseband processor may comprise both analog and digital baseband sections. The analog baseband section includes I/Q filters, analog-to-digital converters, digital-to-analog converters, audio circuits, and other circuits. The digital baseband section may include one or more encoders, decoders, equalizers/demodulators, GMSK modulators, GPRS ciphers, transceiver controls, automatic frequency control (AFC), automatic gain control (AGC), power amplifier (PA) ramp control, and other circuits.

In various aspects, the baseband processor also may be connected to one or more memory units via a memory bus. In one aspect, for example, the baseband processor may be connected to a flash memory unit and a secure digital (SD) memory unit. The memory units may be removable or non-removable memory. In one aspect, for example, the baseband processor may use approximately 1.6 megabytes of static read-only memory (SRAM) for E-GPRS and other protocol stack needs.

In various aspects, the baseband processor also may be connected to a subscriber identity module (SIM). The baseband processor may have a SIM interface for the SIM, where the SIM may comprise a smart card that encrypts voice and data transmissions and stores data about the specific user so that the user can be identified and authenticated to the network supplying voice or data communications. The SIM also may store data such as personal phone settings specific to the user and phone numbers. The SIM can be removable or non-removable.

In various aspects, the baseband processor may further include various interfaces for communicating with a host processor of the processing subsystem 304. For example, the baseband processor may have one or more universal asynchronous receiver-transmitter (UART) interfaces, one or more control/status lines to the host processor, one or more control/data lines to the host processor, and one or more audio lines to communicate audio signals to an audio subsystem of processing subsystem 514. The aspects are not limited in this context.

In various aspects, the processing subsystem 304 may provide computing or processing operations for the mobile device 102 and/or for the authentication subsystem 306. For example, the processing subsystem 304 may be arranged to execute various software programs for the mobile device 102 as well as several software programs for the authentication subsystem 306. Although the processing subsystem 304 may be used to implement operations for the various aspects as software executed by a processor, it may be appreciated that the operations performed by the processing subsystem 304 also may be implemented using hardware circuits or structures, or a combination of hardware and software, as desired for a particular implementation.

In various aspects, the processing subsystem 304 may include a processor implemented using any processor or logic device, such as a complex instruction set computer (CISC) microprocessor, a reduced instruction set computing (RISC) microprocessor, a very long instruction word (VLIW) microprocessor, a processor implementing a combination of instruction sets, or other processor device. In one aspect, for example, a processor may be implemented as a general purpose processor, such as a processor made by Intel Corporation, Santa Clara, Calif. The processor also may be implemented as a dedicated processor, such as a controller, microcontroller, embedded processor, a digital signal processor (DSP), a network processor, a media processor, an input/output (I/O) processor, a media access control (MAC) processor, a radio baseband processor, a field programmable gate array (FPGA), a programmable logic device (PLD), and so forth.

In one aspect, the processing subsystem 304 may include a memory to connect to the processor. The memory may be implemented using any machine-readable or computer-readable media capable of storing data, including both volatile and non-volatile memory. For example, the memory may include ROM, RAM, DRAM, DDRAM, SDRAM, SRAM, PROM, EPROM, EEPROM, flash memory, polymer memory such as ferroelectric polymer memory, ovonic memory, phase change or ferroelectric memory, silicon-oxide-nitride-oxide-silicon (SONOS) memory, magnetic or optical cards, or any other type of media suitable for storing information. It is worthy to note that some portion or all of the memory may be included on the same integrated circuit as the processor thereby obviating the need for a memory bus. Alternatively some portion or all of the memory may be disposed on an integrated circuit or other medium, for example a hard disk drive, that is external to the integrated circuit of the processor, and the processor may access the memory via a memory bus, for example.

In various aspects, the memory may store one or more software components (e.g., application client modules). A software component may refer to one or more programs, or a portion of a program, used to implement a discrete set of operations. A collection of software components for a given device may be collectively referred to as a software architecture or application framework. A software architecture for the mobile device 102 is described in more detail below.

A software architecture suitable for use with the mobile device 102 may include a user interface (UI) module, an interface module, a data source or backend services module (data source), and a third party API module. An optional LBS module may comprise a user based permission module, a parser module (e.g., National Maritime Electronic Association or NMEA), a location information source module, and a position information source module. In some aspects, some software components may be omitted and others added. Further, operations for some programs may be separated into additional software components, or consolidated into fewer software components, as desired for a given implementation. The mobile device 102 software architecture may comprise several elements, components or modules, collectively referred to herein as a "module." A module may be implemented as a circuit, an integrated circuit, an application specific integrated circuit (ASIC), an integrated circuit array, a chipset comprising an integrated circuit or an integrated circuit array, a logic circuit, a memory, an element of an integrated circuit array or a chipset, a stacked integrated circuit array, a processor, a digital signal processor, a programmable logic device, code, firmware, software, and any combination thereof.

Having described the mobile device 102 as one example of computer system, it will be appreciated that any of the following computer systems, without limitation, computer networks, desktop computers, laptop computers, notebook computers, tablet computers, tablet computers, mobile phones, personal digital assistants, appliances, positioning systems, media devices, automatic teller machines (ATM), kiosks, public modes of transportation (bus, train, subway, airplane, boat, rental car, . . . ), building entrances, stadiums, turnstiles, medical systems that dispense medication in any form could be equipped with at least one electrode and a detection subsystem to authenticate the user as the owner of the computer system for security purposes. For the sake of conciseness and clarity, not all of these computer systems will be discussed here.

Turning briefly now to FIGS. 19-21, which illustrate aspects of a mobile device 1100 received in a mating configuration with a mobile device enclosing arrangement 1102 comprising a detection circuit integrated therewith for detecting an electrical signal generated by an ingestible event marker, such as the IEM device, otherwise referred to herein as an ingestible event marker system 106, for example. They can be made of hard plastic or in the newer market adhesive-backed vinyl pieces. FIG. 19 illustrates one aspect of a mobile device 1100 received in a mating configuration with a mobile device enclosing arrangement 1102 comprising a detection circuit integrated therewith for detecting an electrical signal generated by an ingestible event marker system 106, for example.

The enclosing arrangement 1102 may be referred to as a housing, enclosure, attachment, skin, design cover, among other accessories for mobile devices, and may substantially or partially cover or enclose the mobile device 1100. FIG. 20 illustrates the mobile device 1100 and the enclosing arrangement 1102 (cradle, protective cover, skin, and the like) for receiving the mobile device 1100 in an unmated configuration. The mobile device 1100 shown in FIGS. 19 and 20 is substantially similar to the mobile devices 102 and others described hereinbefore and, therefore, a high level description of similar functional modules will not be repeated here for the sake of conciseness and clarity of disclosure.

As shown in FIGS. 19 and 20, the mobile device 1100 is configured to mate with the enclosing arrangement 1102. The enclosing arrangement 1102 contains a detection module 1200 integrated therewith. The detection module 1200 comprises a detection subsystem comprising an electrode input circuit similar to the detection subsystem 516 and electrode input circuit shown in FIG. 4 as electrode input/output interface circuit 401. Due to the similarity of the detection subsystem and electrode input circuit components, the particular details will not be repeated here for the sake of conciseness and clarity of disclosure. The enclosing arrangement 1102 also includes electrodes 1202A and 1202B (not shown in FIG. 20 and shown in FIG. 21) to couple the patient to the detection module 1200. The detection module 1200 may be electrically coupled to functional modules of the mobile device 1100 to detect and process the unique electrical signature generated by the ingestible event marker system 106 (e.g., IEM device). The detection module 1200 may be electrically coupled to the functional modules of the mobile device 1100 using any suitable techniques such as, for example, inductive coupling, wireless transmission, electrical connector, and the like. One example of a housing comprising a suitable connector to electrically couple the detection module 1200 to the functional modules of the mobile device 1100 is described in connection with FIG. 21.

FIG. 21 illustrates one aspect of a enclosing arrangement 1102 for receiving a mobile device where the enclosing arrangement 1102 comprises a detection circuit 1200 for detecting an electrical signal generated by an ingestible event marker integrated therewith and a connector 1300 for electrically coupling the detection circuit 1200 to the functional modules of the mobile device. In use, the mobile device (not shown) is slidably inserted over the enclosing arrangement 1102 and plugged into the connector 1300. The electrodes 1202A, 1202B are used tot couple the patient to the detection module 1200. The connector 1300 couples the detection module 1200 to the functional modules of the mobile device 1100 (FIG. 20) for communication purposes, among other purposes. In one aspect, the detection module 1200 integrated with the enclosing arrangement 1102 is a standalone module and includes all the necessary electronic modules to detect the unique electrical current signature generated by the IEM device.

Figure 4:
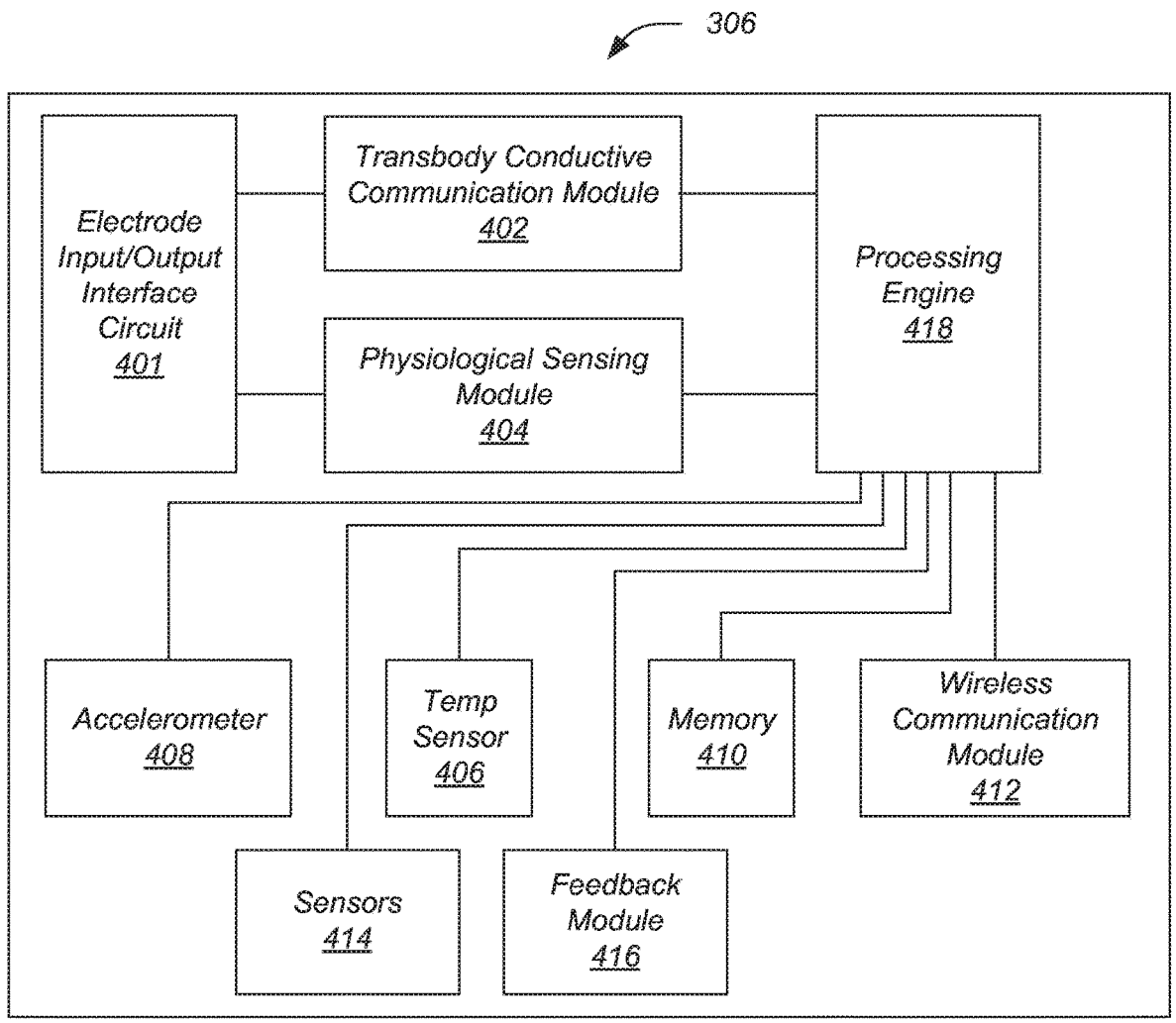
FIG. 4 is a block functional diagram of one aspect of an authentication subsystem for detecting and/or generating a transconductance signal to confirm the identity of a person.

Turning now back to FIG. 4, which is a block functional diagram of one aspect of an authentication subsystem 306 for detecting and/or generating personal electrical signals to authenticate the user and prove the identity of the subject 100 (FIG. 1). The authentication subsystem 306 comprises an electrode input/output interface circuit 401 to receive/transmit electrical signals from/to the electrodes 104a, 104b. The authentication subsystem 306 can be configured to operate in receive mode, broadcast mode, or combinations thereof. In receive mode, the input/output interface circuit 401 receives electrical signals from the electrodes 104a, 104b. In broadcast mode, the input/output interface circuit 401 transmits electrical signals to the electrodes 104a, 104b.

Figure 5:
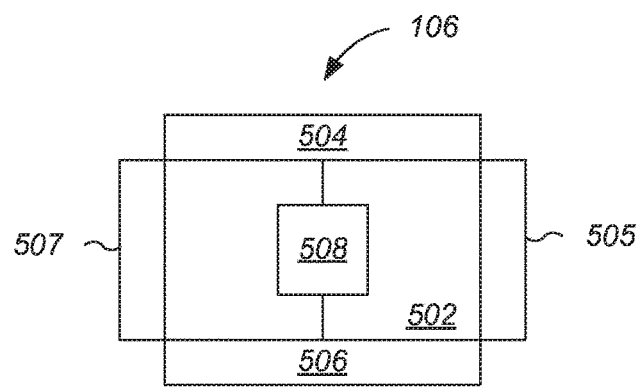
FIG. 5 illustrates one aspect of an ingestible event marker system configured to generate a unique transconductance signal for confirming the identity of a person.

A transbody conductive communication module 402 and a physiological sensing module 404 are electrically coupled to the electrode input/output interface circuit 401. In one aspect, the transbody conductive communication module 402 is implemented as a first, e.g., high, frequency (HF) signal chain and the physiological sensing module 404 is implemented as a second, e.g., low, frequency (LF) signal chain. Also shown are CMOS temperature sensing module 406 (for detecting ambient temperature) and a 3-axis accelerometer 408. The authentication subsystem 306 also comprises a processing engine 418 (for example, a microcontroller and digital signal processor), a non-volatile memory 410 (for data storage), and a wireless communication module 412 to receive data from and/or transmit data to another device, for example in a data download/upload action, respectively. In various aspects, the communication module 412 may comprise one or more transmitters/receivers ("transceiver") modules. As used herein, the term "transceiver" may be used in a very general sense to include a transmitter, a receiver, or a combination of both, without limitation. In one aspect, the transbody conductive communication module 402 is configured to communicate with an ingestible event marker system 106 (FIGS. 1, 5). In receive mode, the transbody conductive communication module 402 is configured to receive a transconduction current signal from the subject 100 (FIG. 1) via at least one of the electrodes 104a, 104b (FIG. 1). In broadcast mode, the transbody conductive communication module 402 is configured to transmit a transconduction current signal to the subject 100 via at least one of the electrodes 104a, 104b (FIG. 1). In one aspect, the transbody conductive communication module 402 is configured as a skin or design cover for a mobile device.

The sensors 414 typically contact the subject 100 (FIG. 1), e.g., are removably attachable to the torso. In various aspects, the sensors 414 may be removably or permanently attached to the authentication subsystem 306. For example, the sensors 414 may be removably connected to another device by snapping metal studs. The sensors 414 may comprise, for example, various devices capable of sensing or receiving the physiologic data. The types of sensors 414 include, for example, electrodes such as biocompatible electrodes. The sensors 414 may be configured, for example, as a pressure sensor, a motion sensor, an accelerometer, an electromyography (EMG) sensor, an event marker system, a biopotential sensor, an electrocardiogram sensor, a temperature sensor, a tactile event marker sensor, and an impedance sensor.

The feedback module 416 may be implemented with software, hardware, circuitry, various devices, and combinations thereof. The function of the feedback module 416 is to provide communication with the subject 100 (FIG. 1) in a discreet, tactful, circumspect manner as described above. In various aspects the feedback module 416 may be implemented to communicate with the subject 100 using techniques that employ visual, audio, vibratory/tactile, olfactory, and taste.

FIG. 5 illustrates one aspect of an ingestible event marker system 106 configured to generate a unique transconductance signal for confirming the identity of a person. In various aspects the ingestible event marker system 106 can be used in association with any medication product, as mentioned above, to determine the origin of the medication and to confirm that at least one of the right type and the right dosage of medication was delivered to the patient and in some aspects to determine when a patient takes the medication product. The scope of the present disclosure, however, is not limited by the environment and the medication product that may be used with the system 106. For example, the system 106 may be activated either in wireless mode, in galvanic mode by placing the system 106 within a capsule and then placing the capsule within a conducting fluid, or a combination thereof, or exposing the system 106 to air. Once placed in a conducting fluid, for example, the capsule would dissolve over a period of time and release the system 106 into the conducting fluid. Thus, in one aspect, the capsule would contain the system 106 and no product. Such a capsule may then be used in any environment where a conducting fluid is present and with any product. For example, the capsule may be dropped into a container filled with jet fuel, salt water, tomato sauce, motor oil, or any similar product. Additionally, the capsule containing the system 106 may be ingested at the same time that any pharmaceutical product is ingested in order to record the occurrence of the event, such as when the product was taken.

In the specific example of the system 106 combined with a medication or pharmaceutical product, as the product or pill is ingested, or exposed to air, the system 106 is activated in galvanic mode. The system 106 controls conductance to produce a unique current signature that is detected by the electrodes 104a, 104b (FIGS. 1-4), for example, thereby transmitting a unique transconduction signal that authenticates the user as the owner of the computer system (e.g., the mobile device 102). When activated in wireless mode, the system controls modulation of capacitive plates to produce a unique voltage signature associated with the system 106 that is detected.

In one aspect, the system 106 includes a framework 502. The framework 502 is a chassis for the system 106 and multiple components are attached to, deposited upon, or secured to the framework 502. In this aspect of the system 106, a digestible material 504 is physically associated with the framework 502. The material 504 may be chemically deposited on, evaporated onto, secured to, or built-up on the framework all of which may be referred to herein as "deposit" with respect to the framework 502. The material 504 is deposited on one side of the framework 502. The materials of interest that can be used as material 504 include, but are not limited to: Cu, CuCl, or CuI. The material 504 is deposited by physical vapor deposition, electrodeposition, or plasma deposition, among other protocols. The material 504 may be from about 0.05 to about 500 μm thick, such as from about 5 to about 100 μm thick. The shape is controlled by shadow mask deposition, or photolithography and etching. Additionally, even though only one region is shown for depositing the material, each system 106 may contain two or more electrically unique regions where the material 504 may be deposited, as desired.

At a different side, which is the opposite side as shown in FIG. 5, another digestible material 506 is deposited, such that the materials 504, 506 are dissimilar and insulated from each other. Although not shown, the different side selected may be the side next to the side selected for the material 504. The scope of the present disclosure is not limited by the side selected and the term "different side" can mean any of the multiple sides that are different from the first selected side. In various aspects, the dissimilar material may be located at different positions on a same side. Furthermore, although the shape of the system is shown as a square, the shape may be any geometrically suitable shape. The materials 504, 506 are selected such that they produce a voltage potential difference when the system 106 is in contact with conducting liquid, such as body fluids. The materials of interest for material 506 include, but are not limited to: Mg, Zn, or other electronegative metals. As indicated above with respect to the material 504, the material 506 may be chemically deposited on, evaporated onto, secured to, or built-up on the framework. Also, an adhesion layer may be necessary to help the material 506 (as well as material 504 when needed) to adhere to the framework 502. Typical adhesion layers for the material 506 are Ti, TiW, Cr or similar material. Anode material and the adhesion layer may be deposited by physical vapor deposition, electrodeposition or plasma deposition. The material 506 may be from about 0.05 to about 500

µm thick, such as from about 5 to about 100 µm thick. However, the scope of the present disclosure is not limited by the thickness of any of the materials nor by the type of process used to deposit or secure the materials to the framework 502.

According to the disclosure set forth, the materials 504, 506 can be any pair of materials with different electrochemical potentials. Additionally, in the aspects wherein the system 106 is used in-vivo, the materials 504, 506 may be vitamins that can be absorbed. More specifically, the materials 504, 506 can be made of any two materials appropriate for the environment in which the system 106 will be operating. For example, when used with an ingestible product, the materials 504, 506 are any pair of materials with different electrochemical potentials that are ingestible. An illustrative example includes the instance when the system 106 is in contact with an ionic solution, such as stomach acids, fluids excreted through the surface of the skin, fluids present below the surface of the skin, for example. Suitable materials are not restricted to metals, and in certain aspects the paired materials are chosen from metals and non-metals, e.g., a pair made up of a metal (such as Mg) and a salt (such as CuCl or CuI). With respect to the active electrode materials, any pairing of substances—metals, salts, or intercalation compounds—with suitably different electrochemical potentials (voltage) and low interfacial resistance are suitable.

Materials and pairings of interest include, but are not limited to, those reported in TABLE 1 below. In one aspect, one or both of the metals may be doped with a non-metal, e.g., to enhance the voltage potential created between the materials as they come into contact with a conducting liquid. Non-metals that may be used as doping agents in certain aspects include, but are not limited to: sulfur, iodine, and the like. In another aspect, the materials are copper iodine (CuI) as the anode and magnesium (Mg) as the cathode. Aspects of the present disclosure use electrode materials that are not harmful to the human body.

TABLE 1

|  | Anode | Cathode |
| --- | --- | --- |
| Metals | Magnesium, Zinc Sodium (†), Lithium (†) Iron |  |
| Salts |  | Copper salts: iodide, chloride, bromide, sulfate, formate, (other anions possible) $Fe^{3+}$ salts: e.g. orthophosphate, pyrophosphate, (other anions possible) Oxygen (††) on platinum, gold or other catalytic surfaces |
| Intercalation compounds | Graphite with Li, K, Ca, Na, Mg | Vanadium oxide Manganese oxide |

Thus, when the system 106 is in contact with the conducting fluid, a current path is formed through the conducting fluid between the dissimilar materials 504, 506. A control device 508 is secured to the framework 502 and electrically coupled to the materials 504, 506. The control device 508 includes electronic circuitry, for example control logic that is capable of controlling and altering the conductance between the materials 504, 506.

The voltage potential created between the dissimilar materials 504, 506 provides the power for operating the system as well as produces the current flow through the conducting fluid and the system 106. In one aspect, the system 106 operates in direct current mode. In an alternative aspect, the system 106 controls the direction of the current so that the direction of current is reversed in a cyclic manner, similar to alternating current. As the system reaches the conducting fluid or the electrolyte, where the fluid or electrolyte component is provided by a physiological fluid, e.g., stomach acid, the path for current flow between the dissimilar materials 504, 506 is completed external to the system 106; the current path through the system 106 is controlled by the control device 508. Completion of the current path allows for the current to flow and in turn a receiver, not shown, can detect the presence of the current and recognize that the system 106 has been activate and the desired event is occurring or has occurred.

In one aspect, the two dissimilar materials 504, 506 are similar in function to the two electrodes needed for a direct current power source, such as a battery. The conducting liquid acts as the electrolyte needed to complete the power source. The completed power source described is defined by the physical chemical reaction between the dissimilar materials 504, 506 of the system 106 and the surrounding fluids of the body. The completed power source may be viewed as a power source that exploits reverse electrolysis in an ionic or a conduction solution such as gastric fluid, blood, or other bodily fluids and some tissues. Additionally, the environment may be something other than a body and the liquid may be any conducting liquid. For example, the conducting fluid may be salt water or a metallic based paint.

In certain aspects, the two dissimilar materials 504, 506 are shielded from the surrounding environment by an additional layer of material. Accordingly, when the shield is dissolved and the two dissimilar materials 504, 506 are exposed to the target site, a voltage potential is generated.

In certain aspects, the complete power source or supply is one that is made up of active electrode materials, electrolytes, and inactive materials, such as current collectors, packaging. The active materials are any pair of materials with different electrochemical potentials. Suitable materials are not restricted to metals, and in certain aspects the paired materials are chosen from metals and non-metals, e.g., a pair made up of a metal (such as Mg) and a salt (such as CuI). With respect to the active electrode materials, any pairing of substances—metals, salts, or intercalation compounds—with suitably different electrochemical potentials (voltage) and low interfacial resistance are suitable.

A variety of different materials may be employed as the materials that form the electrodes. In certain aspects, electrode materials are chosen to provide for a voltage upon contact with the target physiological site, e.g., the stomach, sufficient to drive the system of the identifier. In certain aspects, the voltage provided by the electrode materials upon contact of the metals of the power source with the target physiological site is 0.001 V or higher, including 0.01 V or higher, such as 0.1 V or higher, e.g., 0.3 V or higher, including 0.5 volts or higher, and including 1.0 volts or higher, where in certain aspects, the voltage ranges from about 0.001 to about 10 volts, such as from about 0.01 to about 10 V.

Referring still to FIG. 5, the dissimilar materials 504, 506 provide the voltage potential to activate the control device 508. Once the control device 508 is activated or powered up, the control device 508 can alter conductance between the first and second materials 504, 506 in a unique manner. By altering the conductance between the first and second materials 504, 506, the control device 508 is capable of controlling the magnitude of the current through the conducting liquid that surrounds the system 106. This produces a unique current signature that can be detected and measured by a receiver (not shown), which can be positioned internal or external to the body. The receiver is disclosed in greater detail in U.S. patent application Ser. No. 12/673,326 entitled "BODY-ASSOCIATED RECEIVER AND METHOD" filed on Dec. 15, 2009, and published as 2010-0312188 A1 dated Dec. 9, 2010 which is incorporated herein by reference in its entirety. In addition to controlling the magnitude of the current path between the materials, non-conducting materials, membrane, or "skirt" are used to increase the "length" of the current path and, hence, act to boost the conductance path, as disclosed in the U.S. patent application Ser. No. 12/238,345 entitled, "IN-BODY DEVICE WITH VIRTUAL DIPOLE SIGNAL AMPLIFICATION" filed Sep. 25, 2008, the entire content of which is incorporated herein by reference. Alternatively, throughout the disclosure herein, the terms "non-conducting material," "membrane," and "skirt" are interchangeably used with the term "current path extender" without impacting the scope or the present aspects and the claims herein. The skirt, shown in portion at 505, 507, respectively, may be associated with, e.g., secured to, the framework 502. Various shapes and configurations for the skirt are contemplated as within the scope of the various aspects of the present invention. For example, the system 106 may be surrounded entirely or partially by the skirt and the skirt maybe positioned along a central axis of the system 106 or off-center relative to a central axis. Thus, the scope of the present invention as claimed herein is not limited by the shape or size of the skirt. Furthermore, in other aspects, the dissimilar materials 504, 506 may be separated by one skirt that is positioned in any defined region between the dissimilar materials 504, 506.

The system 106 may be grounded through a ground contact. The system 106 also may include a sensor module. In operation, ion or current paths are established between the first material 504 to the second material 506 and through a conducting fluid in contact with the system 106. The voltage potential created between the first and second materials 504, 506 is created through chemical reactions between the first and second materials 504, 506 and the conducting fluid. In one aspect, the surface of the first material 504 is not planar, but rather an irregular surface. The irregular surface increases the surface area of the material and, hence, the area that comes in contact with the conducting fluid.

In one aspect, at the surface of the first material 504, there is chemical reaction between the material 504 and the surrounding conducting fluid such that mass is released into the conducting fluid. The term mass as used herein refers to protons and neutrons that form a substance. One example includes the instant where the material is CuCl and when in contact with the conducting fluid, CuCl becomes Cu (solid) and Cl— in solution. The flow of ions into the conduction fluid is via ion paths. In a similar manner, there is a chemical reaction between the second material 506 and the surrounding conducting fluid and ions are captured by the second material 506. The release of ions at the first material 504 and capture of ion by the second material 506 is collectively referred to as the ionic exchange. The rate of ionic exchange and, hence the ionic emission rate or flow, is controlled by the control device 508. The control device 508 can increase or decrease the rate of ion flow by altering the conductance, which alters the impedance, between the first and second materials 504, 506. Through controlling the ion exchange, the system 106 can encode information in the ionic exchange process. Thus, the system 106 uses ionic emission to encode information in the ionic exchange.

The control device 508 can vary the duration of a fixed ionic exchange rate or current flow magnitude while keeping the rate or magnitude near constant, similar to when the frequency is modulated and the amplitude is constant. Also, the control device 508 can vary the level of the ionic exchange rate or the magnitude of the current flow while keeping the duration near constant. Thus, using various combinations of changes in duration and altering the rate or magnitude, the control device 508 encodes information in the current flow or the ionic exchange. For example, the control device 508 may use, but is not limited to any of the following techniques namely, Binary Phase-Shift Keying (PSK), Frequency Modulation (FM), Amplitude Modulation (AM), On-Off Keying, and PSK with On-Off Keying.

Various aspects of the system 106 may comprise electronic components as part of the control device 508. Components that may be present include but are not limited to: logic and/or memory elements, an integrated circuit, an inductor, a resistor, and sensors for measuring various parameters. Each component may be secured to the framework and/or to another component. The components on the surface of the support may be laid out in any convenient configuration. Where two or more components are present on the surface of the solid support, interconnects may be provided.

The system 106 controls the conductance between the dissimilar materials and, hence, the rate of ionic exchange or the current flow. Through altering the conductance in a specific manner the system is capable of encoding information in the ionic exchange and the current signature. The ionic exchange or the current signature is used to uniquely identify the specific system. Additionally, the system 106 is capable of producing various different unique exchanges or signatures and, thus, provides additional information. For example, a second current signature based on a second conductance alteration pattern may be used to provide additional information, which information may be related to the physical environment. To further illustrate, a first current signature may be a very low current state that maintains an oscillator on the chip and a second current signature may be a current state at least a factor of ten higher than the current state associated with the first current signature.

Figure 6:
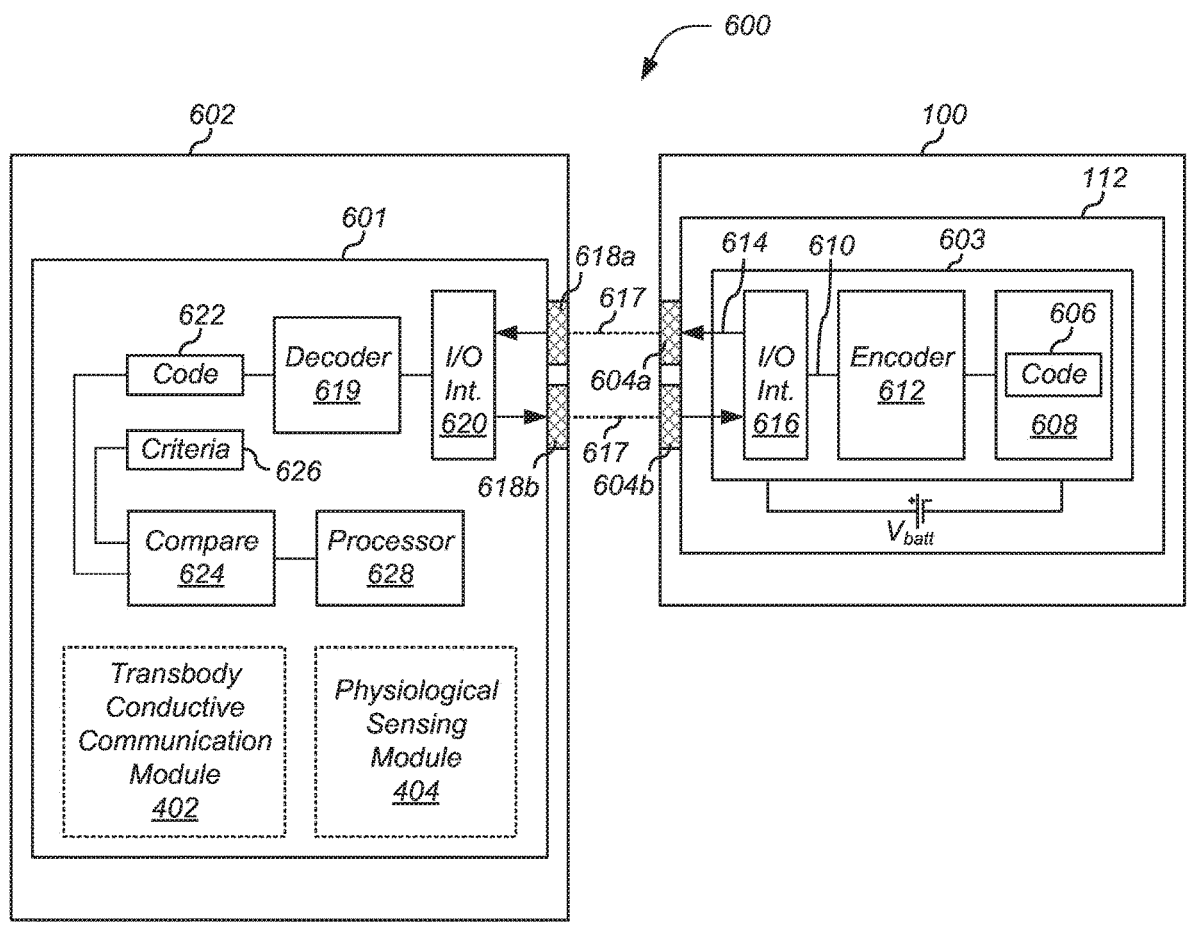
FIG. 6 illustrates one aspect of an authentication system comprising a target authentication device and an authentication module comprising a body-associated device.

Having now described the basic elements of a personal authentication system, the disclosure now turns to a description of various aspects of authentication systems. FIG. 6 illustrates one aspect of an authentication system 600 comprising a target authentication device 602 and an authentication module comprising a body-associated device 112. The target authentication device 602 comprises an authentication receiver module 601. The body-associated device 112 comprises a transmission device 603. In one embodiment, the body-associated device 112 is destroyed when it is removed from the body of the subject 100.

The body-associated device 112 is located on the surface of the skin and is electrically coupled to the subject 100 via electrodes 604a, 604b. In one aspect, the body-associated device 112 comprises a transmission device 603 that is configured, or programmed, with a secret code 606 that is stored in memory 608, such as a password or a private key for more sophisticated authentication mechanisms. The body-associated device 112 acts in broadcast mode (opposite to the receive mode). The secret code 606 is read from the memory 608 and is encoded into a signal 610 by an encoder 612. The encoded signal 610 is converted to an electrically conductive signal 614 by the I/O interface circuit 616. The encoded electrically conductive signal 614 is applied to the body 617 of the subject 100 via the electrodes 604a, 604b.

A battery $V_{batt}$ may be included in the body-associated device as a power source. Alternatively, a power source may be implemented by coupling energy through the electrodes 604a, 604b from the target authentication device 602. In yet another alternative, a power source similar to the power source described in connection with the ingestible event marker 106 (FIG. 5) may be employed where the power source may be activated by fluid excreted on the surface of the skin of the subject 100.

The electrically conductive signal 614 is conducted through the body 617 of the subject 100 to the authentication receiver module 601 of the target authentication device 602. Electrodes 618a, 618b detect the electrically conductive signal 614 from the body 617 and are coupled to a decoder 619 though an I/O interface circuit 620. The decoder 619 decodes the electrically conductive signal 614. The decoded code 622 is then compared by compare module 624 to established criteria 626. When the code 622 matches the established criteria 626, compare module 624 provides the results to the processor 628, which determines whether the electrical signal matches the predetermined criteria to authenticate the identity of the user based on the an electrical signal. If a match occurs, the processor 629 unlocks the target authentication device 602 and enables access by the subject 100. In one aspect, the authentication receiver module 601 is configured to encode the detected signal with a secret and retransmit the encoded signal back to the receiver module where it is compared to an expected result dependent on the mathematical properties of the encoding and the secret. In one aspect, the authentication receiver module 601 is configured to authenticate a challenge-response authentication, which is an authentication process that verifies an identity by requiring correct authentication information to be provided in response to a challenge. The authentication information may be usually a value that is computed in response to an unpredictable challenge value, but it may be just a password.

The target authentication device 602 may be any number of digital instruments. As previously discussed, the target authentication device 602 may be a mobile device 102 as described in connection with FIGS. 1-3. In other aspects, the target authentication device 602 may be any of the computer systems identified above. In one aspect, the target authentication device 602 may be located on a keyboard to ensure the identity of the user when the hands touch the keyboard, allowing the subject 100 to authenticate against web sites; a check-out terminal, which authenticates against the bank account of the subject 100 and allows the subject 100 to pay for transactions; a car that knows the subject 100 is the one holding the steering wheel and starts only for the subject 100; a doorknob that unlocks when authorized subjects 100 touch it; the target may even be another individual, so that when the subject 100 shake hands both parties are assured of the other's identity.

The body associated device 112 comprising the transmission device 603 may be a patch, implant, pendant, ring, article of clothing, piercing, or piece of jewelry. The body associated device 112 is physically and electrically associated with the subject 100, and contains a secret code 606.

In one aspect, the authentication receiver module 601 of the target authentication device 602 may comprise a trans-body conductive communication module 402 as described in connection with FIG. 4, shown in phantom to indicate that it is optional. Communication could be over the same transconductive link established with the ingestible event marker system 106 described in FIG. 5, where the transmitter drives a dipole located on the body 617 of the subject 100 and the target authentication device 602 also contains a dipole for receiving the encoded signal. Alternatively, either the target authentication device 602 or the transmission device 603 or both may comprise a single electrode in contact with the body 617, with the counter electrode being a capacitive connection to free space. All of these cases ensure that both the transmission device 603 containing the authentication code 606 and the target authentication device 602 are both in conductive contact with the same body 617 in order for authentication to be successful.

In another aspect, the authentication receiver module 601 of the target authentication device 602 may comprise a physiological sensing module 404 as described in connection with FIG. 4, shown in phantom to indicate that it is optional. The physiological sensing module 404 may be employed to monitor biometric signatures associated with the subject 100 to establish that it is in fact attached to the subject 100. A profile of physiologic activity, based on parameters like heart rate, activity patterns, GSR, body temperature, circadian rhythms, and so forth may be generated on the body-associated device 112. This signature could be hashed with the authentication code 606 and transmitted to the target authentication device 602. The target authentication device 602 would then compare the biometric signature to a baseline database to confirm the subject 100. In one aspect, the biometric signature is derived from the at least one physiological signal and the biometric signature is compared to a user-associated signature. The user associated-signature may be derived from biometric data stored in a memory over time to generate a baseline biometric signature, wherein the authentication module device compares the biometric signature to the baseline biometric signature to authenticate the identity of the user. The user-associated biometric signature also may be derived from other sources outside this system.

In another aspect, the target authentication device 602 acquires a biometric profile over time and compares past readings against current ones. In this way, a sudden change could indicate that the body-associated device 112 has been removed from one person and put on another.

The secret authentication code 606 may be a simple password based authentication, in which case the password may be programmed into the transmission device 603, or the secret authentication code 606 may be a more complex challenge-response scheme where bi-directional communication is used to establish authentication over a public channel. Other established authentication schemes known in the art are also applicable to this case.

In yet another aspect, is to put a lock on the body-associated device 112 of some kind. A PIN code or tap pattern could be required to unlock the body-associated device 112 and enable it to broadcast the key transconductively (e.g., use the body 617 of the subject 100 as a conductive medium to conduct a current).

The above is a specific instantiation of a key (in this case the body-associated device 112) communicating with and unlocking a lock (in this case the target authentication device 602, such as a mobile device 102, for example) via transconductive communication. In various other aspects, this may be generalized to a number of keys (e.g., patch, watch, key fob in pocket, smart shoes, jewelry, clothing, etc.) communicating with any number of locks (e.g., phone, computer, door, car, cash register, ATM, vending machine). In certain instances it may be beneficial for the communication to be two-way. For instance, in the case of a body-associated device 112 and a mobile device 102, the body-associated device 112 initiates a session by periodically broadcasting the authentication code 606. The mobile device 102 receives the code 606, verifies its authenticity and unlocks the mobile device 102 display 204 (FIGS. 2, 3). The mobile phone 102 may then send an acknowledgement back to the body-associated device 112 via transconduction or a wireless link, and the body-associated device 112 might then decide to download stored physiological data to the mobile device 102. In another instance, the body-associated device 112 may be pre-programmed for a limited number of authentications; after each time a pairing is established between the body-associated device 112 and the mobile device 102, a counter may be incremented until it reaches a limit and the body-associated device 112 is de-authorized.

In another aspect, the relationship between the target identification device 602 and the transmission device 603 can be broadened beyond security and use-related permissions to include assurance of use-related benefits and transactions. For example, in a loyalty management program related to the transmission device 603 (which in addition to the items listed above could include consumer-related product packaging such as drink containers), assured use by a specific individual could be confirmed by the transmission device 603, thereby allowing the loyalty or other benefits to be granted.

In another aspect, instead of being a personally associated authentication token, the transmission device 603 could serve as a value token, like a gift card or event pass. In this case, a temporary transmission device 603 like an adhesive sticker is sold in a conventional transaction. The buyer applies the adhesive sticker to his or her body 617, and the value is transferred to a mobile device 102 (FIGS. 1-3) upon contact with the body 617 of the subject 100. In another example, a club might apply a door key patch to customers that cannot be removed without rendering it inoperative to control access for the duration of an event.

In another aspect, the authentication process may be bidirectional in that the target authentication device 602 (e.g., the mobile device 102) can send a code through the body 617 of the subject 100 to the body-associated device 112 (e.g., a patch). The body-associated device 112 authenticates and sends a signal back to the target authentication device 602 which would then unlock. In another aspect, an electrical current signal from the ingestible event indicator system 106 may be sourced by a small implantable device, e.g., dog tag sized, that sends a signal that is collected by the target authentication device 602 for authentication. The implantable device also may be configured with a physiological sensing module 404 to collect other physiological information.

With reference now to FIGS. 1-6, in yet another aspect, a mobile device 102 could be modified to receive the transconduction signals produced by the ingestible event marker system 106 when the owner simply touches the mobile device 102. The transconduction signal carries authentication information that identifies the subject 100 touching the mobile device 102 as the rightful owner. This eliminates the need to manually enter a PIN, while still assuring that the rightful owner is the subject 100 accessing the target authentication device 102.

In one aspect, the source of the transconduction signal could be an ingested ingestible event marker system 106 or other transconduction signal transmission source, such as a body-associated device 112 or similar transmission device 603 in direct contact with the body 617 of the subject 100. This includes transmitters implanted in the body 617 of the subject 100.

Figure 7:
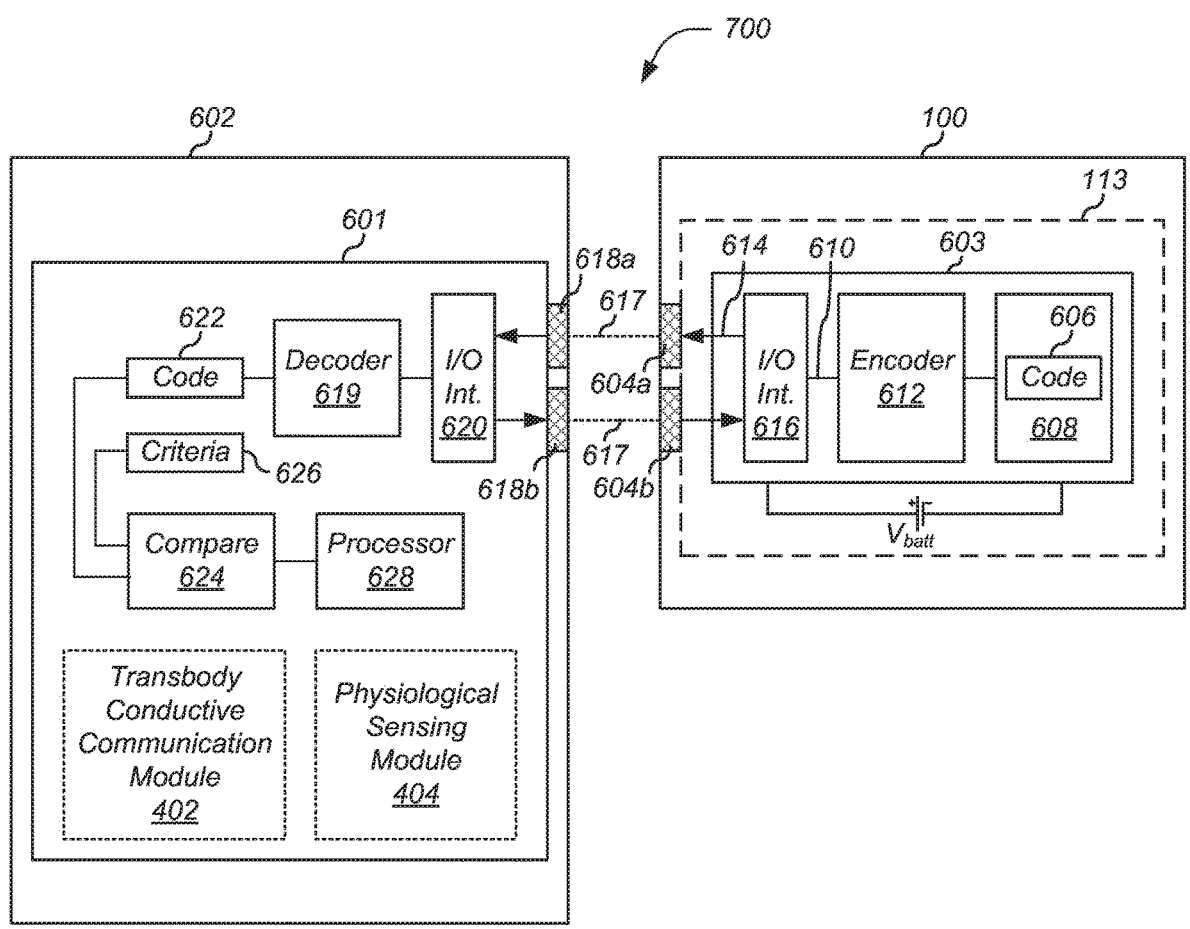
FIG. 7 illustrates one aspect of an authentication system comprising a target authentication device and an authentication transmission module comprising an implantable body-associated device that is located below the skin of the subject.

FIG. 7 illustrates one aspect of an authentication system 700 comprising a target authentication device 602 and an authentication transmission module comprising an implantable body-associated device 113 that is located below the skin of the subject 100. The implantable body-associated device 113 is similar in functionality to the body-associated device 112 described in connection with FIG. 6, with the exception that the implantable body-associated device 113 is shown in phantom to indicate that it is implanted below the skin of the subject 100.

Figure 8:
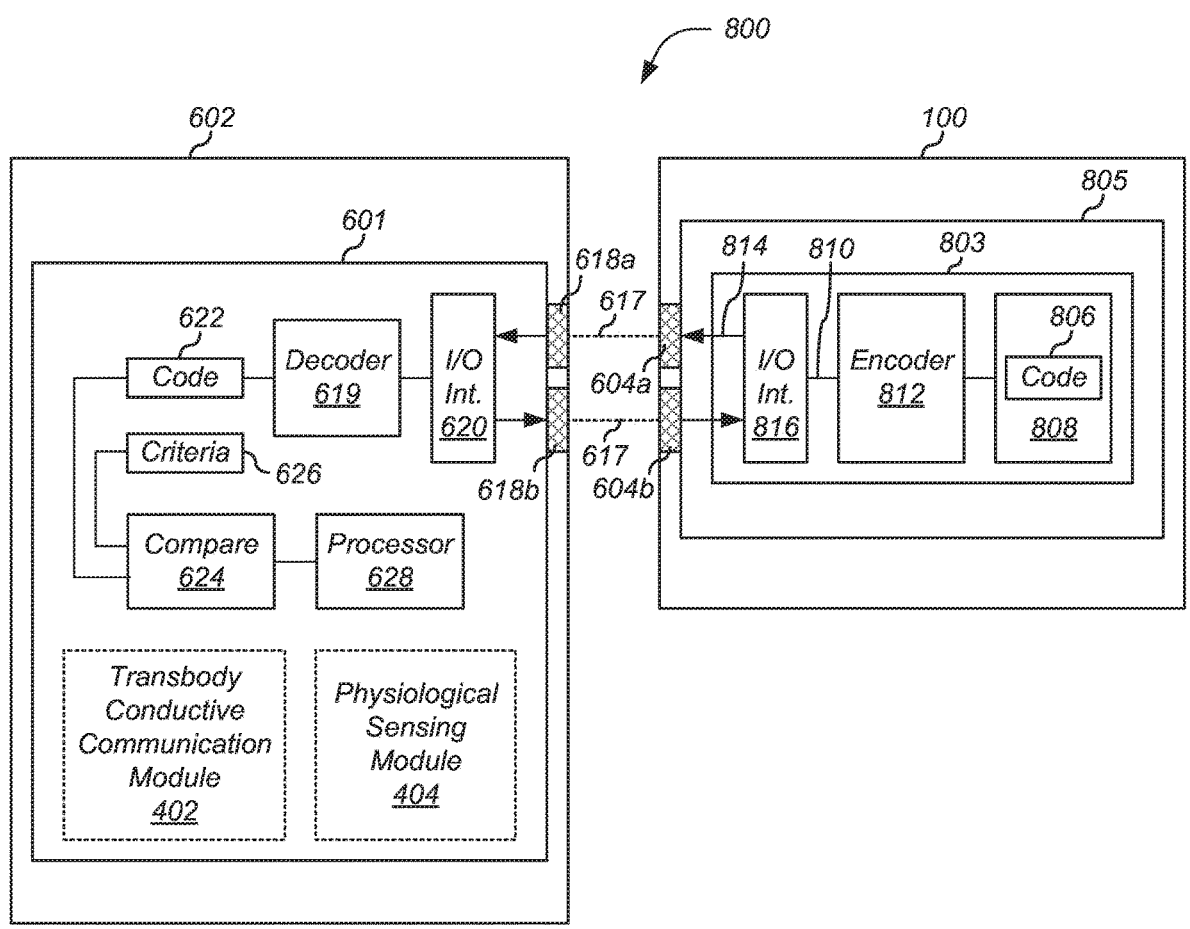
FIG. 8 illustrates one aspect of an authentication system comprising a target authentication device and an authentication transmission module comprising and an event marker system.

FIG. 8 illustrates one aspect of an authentication system 800 comprising a target authentication device 602 and an authentication transmission module comprising and an event marker system 805. The target authentication device 602 comprises an authentication receiver module 601. The event marker system 805 is located on the on or under the skin of the subject 100 and generates transbody conductive signals representative of an authentication code. The event marker system 805 comprises a transmission device 803.

The event marker system 805 is located on the surface of the skin and is electrically coupled to the subject 100 via electrodes 604a, 604b. In one aspect, the event marker system 805 comprises a transmission device 803 that is configured, or programmed, with a secret code 806 that is stored in memory 808, such as a password or a private key for more sophisticated authentication mechanisms. The event marker system 805 acts in broadcast mode. The secret code 806 is read from the memory 808 and is encoded into a signal 810 by an encoder 812. The encoded signal 810 is converted to an electrically conductive signal 814 by the I/O interface circuit 816. The encoded electrically conductive signal 814 is applied to the body 617 of the subject 100 via the electrodes 604a, 604b.

In various aspects, the event marker system 805 may include a power source, such as a power source made up of a pair of electrodes fabricated from dissimilar materials. The event marker system 805 may generate electrical power when it comes into contact with fluids excreted by the skin. Otherwise, the event marker system 805 is functionally equivalent to the operation of the ingestible event marker 106 discussed in connection with FIG. 5. It will be appreciated, however, that in certain circumstances a small battery may be provided in the event marker system 805. The event marker system 805 also may include a second power source electrically coupled to the non-conductive communication module, such as a coil, e.g., an RFID coil.

The electrically conductive signal 814 is conducted through the body 617 of the subject 100 to the authentication receiver module 601 of the target authentication device 602. Electrodes 618a, 618b detect the electrically conductive signal 814 from the body 617 and are coupled to a decoder 619 though an I/O interface circuit 620. The decoder 619 decodes the electrically conductive signal 814. The decoded code 622 is then compared by compare module 624 to established criteria 626. When the code 622 matches the established criteria 626, compare module 624 signals the processor 628, which determines whether the electrical signal matches the predetermined criteria to authenticate the identity of the user based on the an electrical signal. If a match occurs, the processor 629 unlocks the target authentication device 602 and enables access by the subject 100.

In some embodiments of interest, a non-conductive communication module may be provided, which is a wireless radio-frequency module. While the wireless radio-frequency communication module may vary, in some instances this module is a radio-frequency identification (RFID) module. For ease of description purposes only, embodiments of the invention will now be further described in terms of embodiments where the non-conductive communication module is an RFID communication module. However, as noted above the non-conductive communication module may vary widely.

In some instances, the RFID module incorporates, for example, an integrated circuit and an RF antenna. The RFID module may be communicatively associated with a conductive module incorporating, for example, an integrated circuit and a conductive antenna. Either of the RFID module or the conductive module, or both, may function in conjunction with medication and/or medication packaging to receive, process, store, and/or transmit information related to or associated with the medication. As indicated above, the devices and systems can be used across multiple and varied applications to provide secure, controlled, and accurate communications in viable, cost-effective implementations.

Although the present disclosure has been described in connection with a mobile phone, the application may be broadly extended to include other instances where a person needs to authenticate to a system, including, for example access through a locked door, access through a turnstile to get on the subway or into an entertainment venue, access to a computer, access to an ATM or payment terminal at a retailer, access to any other target authentication device 602 described herein.

In one aspect, the authentication receiver module is located inside of an extension chamber on the back of a mobile phone 102 housing 202 (FIG. 2). The electrode connections on the module are wired directly to two electrodes 618a, 618b in the form of metal buttons exposed on the back of the mobile phone housing 202. When the user touches the electrodes 618a, 618b with fingers from the left and right hand, the transbody conductive communication module 402 detects transconduction signals from an ingestable event marker system 106 or from a similar signal generated by an electronic pill emulator. In one aspect, the transbody conductive communication module 402 communicates to the target authentication device 602 via a short range wireless connection, such as Bluetooth, for example. A software module running on the target authentication device 602 monitors detection data delivered from the transbody conductive communication module 402 and flips its display from Locked to Authorized to show that the transconduction signal has been received. In an authentication system, the payload sent in the transconduction signal is configured to be secure and personal to the owner. The receiver is hard-wired directly into the electronics of the target authentication device 602, eliminating the Bluetooth link between receiver and phone.

Figure 9:
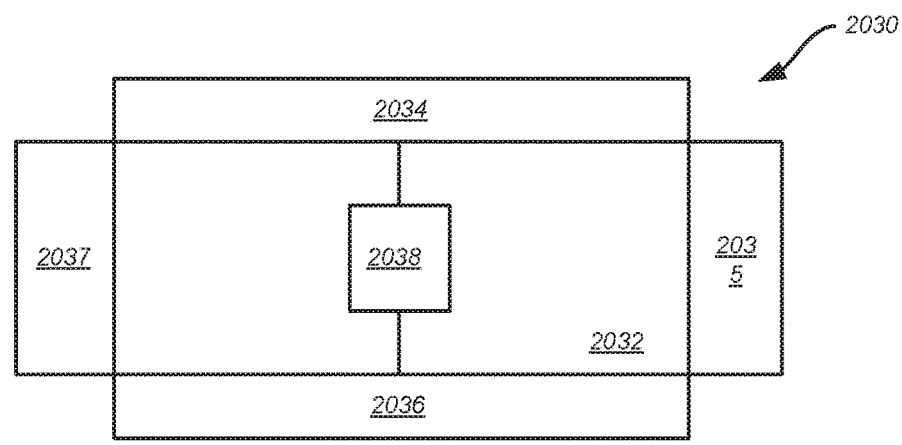
FIG. 9 is a block diagram representation of one aspect of the event indicator system with dissimilar metals positioned on opposite ends.

With reference to FIG. 9, there is shown one aspect of an ingestible device event indicator system with dissimilar metals positioned on opposite ends as system 2030. The system 2030 can be used in association with any pharmaceutical product, as mentioned above, to determine when a patient takes the pharmaceutical product. As indicated above, the scope of the present invention is not limited by the environment and the product that is used with the system 2030. For example, the system 2030 may be placed within a capsule and the capsule is placed within the conducting liquid. The capsule would then dissolve over a period of time and release the system 2030 into the conducting liquid. Thus, in one aspect, the capsule would contain the system 2030 and no product. Such a capsule may then be used in any environment where a conducting liquid is present and with any product. For example, the capsule may be dropped into a container filled with jet fuel, salt water, tomato sauce, motor oil, or any similar product. Additionally, the capsule containing the system 2030 may be ingested at the same time that any pharmaceutical product is ingested in order to record the occurrence of the event, such as when the product was taken.

In the specific example of the system 2030 combined with the pharmaceutical product, as the product or pill is ingested, the system 2030 is activated. The system 2030 controls conductance to produce a unique current signature that is detected, thereby signifying that the pharmaceutical product has been taken. The system 2030 includes a framework 2032. The framework 2032 is a chassis for the system 2030 and multiple components are attached to, deposited upon, or secured to the framework 2032. In this aspect of the system 2030, a digestible material 2034 is physically associated with the framework 2032. The material 2034 may be chemically deposited on, evaporated onto, secured to, or built-up on the framework all of which may be referred to herein as "deposit" with respect to the framework 2032. The material 2034 is deposited on one side of the framework 2032. The materials of interest that can be used as material 2034 include, but are not limited to: Cu or CuI. The material 2034 is deposited by physical vapor deposition, electrodeposition, or plasma deposition, among other protocols. The material 2034 may be from about 0.05 to about 500 .mu.m thick, such as from about 5 to about 100 .mu.m thick. The shape is controlled by shadow mask deposition, or photolithography and etching. Additionally, even though only one region is shown for depositing the material, each system 2030 may contain two or more electrically unique regions where the material 2034 may be deposited, as desired.

At a different side, which is the opposite side as shown in FIG. 9, another digestible material 2036 is deposited, such that materials 2034 and 2036 are dissimilar. Although not shown, the different side selected may be the side next to the side selected for the material 2034. The scope of the present invention is not limited by the side selected and the term "different side" can mean any of the multiple sides that are different from the first selected side. Furthermore, even though the shape of the system is shown as a square, the shape maybe any geometrically suitable shape. Material 2034 and 2036 are selected such that they produce a voltage potential difference when the system 2030 is in contact with conducting liquid, such as body fluids. The materials of interest for material 2036 include, but are not limited to: Mg, Zn, or other electronegative metals. As indicated above with respect to the material 2034, the material 2036 may be chemically deposited on, evaporated onto, secured to, or built-up on the framework. Also, an adhesion layer may be necessary to help the material 2036 (as well as material 2034 when needed) to adhere to the framework 2032. Typical adhesion layers for the material 2036 are Ti, TiW, Cr or similar material. Anode material and the adhesion layer may be deposited by physical vapor deposition, electrodeposition or plasma deposition. The material 2036 may be from about 0.05 to about 500 .mu.m thick, such as from about 5 to about 100 .mu.m thick. However, the scope of the present invention is not limited by the thickness of any of the materials nor by the type of process used to deposit or secure the materials to the framework 2032.

Figure 11:
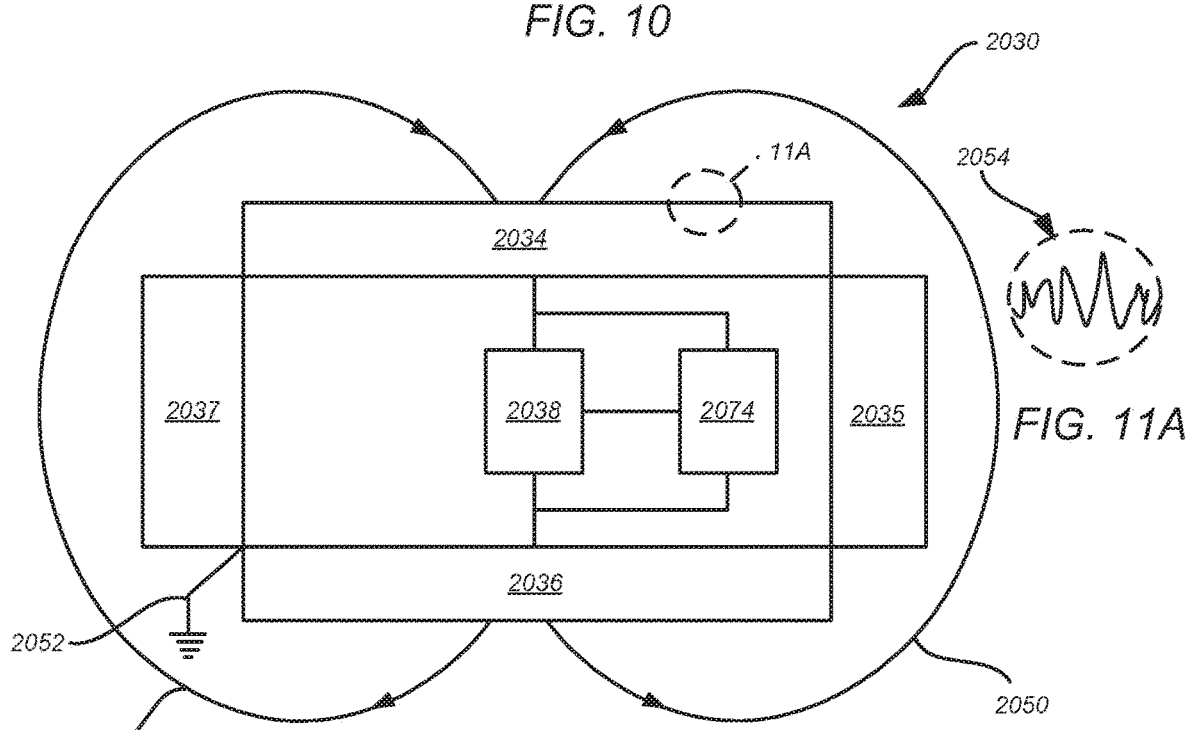
FIG. 11 shows ionic transfer or the current path through a conducting fluid when the event indicator system of FIG. 9 is in contact with conducting liquid and in an active state.

Thus, when the system 2030 is in contact with the conducting liquid, a current path, an example is shown in FIG. 11, is formed through the conducting liquid between material 2034 and 2036. A control device 2038 is secured to the framework 2032 and electrically coupled to the materials 2034 and 2036. The control device 2038 includes electronic circuitry, for example control logic that is capable of controlling and altering the conductance between the materials 2034 and 2036.

The voltage potential created between the materials 2034 and 2036 provides the power for operating the system as well as produces the current flow through the conducting fluid and the system. In one aspect, the system operates in direct current mode. In an alternative aspect, the system controls the direction of the current so that the direction of current is reversed in a cyclic manner, similar to alternating current. As the system reaches the conducting fluid or the electrolyte, where the fluid or electrolyte component is provided by a physiological fluid, e.g., stomach acid, the path for current flow between the materials 2034 and 2036 is completed external to the system 2030; the current path through the system 2030 is controlled by the control device 2038. Completion of the current path allows for the current to flow and in turn a receiver, not shown, can detect the presence of the current and recognize that the system 2030 has been activate and the desired event is occurring or has occurred.

In one aspect, the two materials 2034 and 2036 are similar in function to the two electrodes needed for a direct current power source, such as a battery. The conducting liquid acts as the electrolyte needed to complete the power source. The completed power source described is defined by the physical chemical reaction between the materials 2034 and 2036 of the system 2030 and the surrounding fluids of the body. The completed power source may be viewed as a power source that exploits reverse electrolysis in an ionic or a conductive solution such as gastric fluid, blood, or other bodily fluids and some tissues. Additionally, the environment may be something other than a body and the liquid may be any conducting liquid. For example, the conducting fluid may be salt water or a metallic based paint.

In certain aspects, these two materials are shielded from the surrounding environment by an additional layer of material. Accordingly, when the shield is dissolved and the two dissimilar materials are exposed to the target site, a voltage potential is generated.

Referring again to FIG. 9, the materials 2034 and 2036 provide the voltage potential to activate the control device 2038. Once the control device 2038 is activated or powered up, the control device 2038 can alter conductance between the materials 2034 and 2036 in a unique manner. By altering the conductance between materials 2034 and 2036, the control device 2038 is capable of controlling the magnitude of the current through the conducting liquid that surrounds the system 2030. This produces a unique current signature that can be detected and measured by a receiver (not shown), which can be positioned internal or external to the body. In addition to controlling the magnitude of the current path between the materials, non-conducting materials, membrane, or "skirt" are used to increase the "length" of the current path and, hence, act to boost the conductance path, as disclosed in the U.S. patent application Ser. No. 12/238, 345 entitled, "In-Body Device with Virtual Dipole Signal Amplification" filed Sep. 25, 2008, the entire content of which is incorporated herein by reference. Alternatively, throughout the disclosure herein, the terms "non-conducting material", "membrane", and "skirt" are interchangeably with the term "current path extender" without impacting the scope or the present aspects and the claims herein. The skirt, shown in portion at 2035 and 2037, respectively, may be associated with, e.g., secured to, the framework 2032. Various shapes and configurations for the skirt are contemplated as within the scope of the present invention. For example, the system 2030 may be surrounded entirely or partially by the skirt and the skirt maybe positioned along a central axis of the system 2030 or off-center relative to a central axis. Thus, the scope of the present invention as claimed herein is not limited by the shape or size of the skirt. Furthermore, in other aspects, the materials 2034 and 2036 may be separated by one skirt that is positioned in any defined region between the materials 2034 and 2036.

Figure 10:
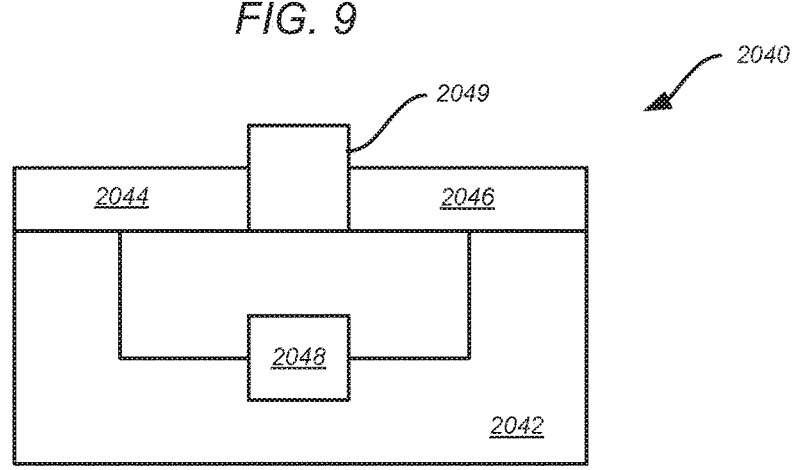
FIG. 10 is a block diagram representation of another aspect of the event indicator system with dissimilar metals positioned on the same end and separated by a non-conducting material.

Referring now to FIG. 10, in another aspect of an ingestible device is shown in more detail as system 2040. The system 2040 includes a framework 2042. The framework 2042 is similar to the framework 2032 of FIG. 9. In this aspect of the system 2040, a digestible or dissolvable material 2044 is deposited on a portion of one side of the framework 2042. At a different portion of the same side of the framework 2042, another digestible material 2046 is deposited, such that materials 2044 and 2046 are dissimilar. More specifically, material 2044 and 2046 are selected such that they form a voltage potential difference when in contact with a conducting liquid, such as body fluids. Thus, when the system 2040 is in contact with and/or partially in contact with the conducting liquid, then a current path, an example is shown in FIG. 11, is formed through the conducting liquid between material 2044 and 2046. A control device 2048 is secured to the framework 2042 and electrically coupled to the materials 2044 and 2046. The control device 2048 includes electronic circuitry that is capable of controlling part of the conductance path between the materials 2044 and 2046. The materials 2044 and 2046 are separated by a non-conducting skirt 2049. Various examples of the skirt 2049 are disclosed in U.S. Provisional Application No. 61/173,511 filed on Apr. 28, 2009 and entitled "HIGHLY RELIABLE INGESTIBLE EVENT MARKERS AND METHODS OF USING SAME" and U.S. Provisional Application No. 61/173,564 filed on Apr. 28, 2009 and entitled "INGESTIBLE EVENT MARKERS HAVING SIGNAL AMPLIFIERS THAT COMPRISE AN ACTIVE AGENT"; as well as U.S. application Ser. No. 12/238,345 filed Sep. 25, 2008 and published as 2009-0082645, entitled "IN-BODY DEVICE WITH VIRTUAL DIPOLE SIGNAL AMPLIFICATION"; the entire disclosure of each is incorporated herein by reference.

Once the control device 2048 is activated or powered up, the control device 2048 can alter conductance between the materials 2044 and 2046. Thus, the control device 2048 is capable of controlling the magnitude of the current through the conducting liquid that surrounds the system 2040. As indicated above with respect to system 2030, a unique current signature that is associated with the system 2040 can be detected by a receiver (not shown) to mark the activation of the system 2040. In order to increase the "length" of the current path the size of the skirt 2049 is altered. The longer the current path, the easier it may be for the receiver to detect the current.

Referring now to FIG. 11, the system 2030 of FIG. 9 is shown in an activated state and in contact with conducting liquid. The system 2030 is grounded through ground contact 2052. The system 2030 also includes a sensor module 2074, which is described in greater detail with respect to FIG. 11 Ion or current paths 2050 form between material 2034 to material 2036 through the conducting fluid in contact with the system 2030. The voltage potential created between the material 2034 and 2036 is created through chemical reactions between materials 2034/2036 and the conducting fluid.

FIG. 11A shows an exploded view of the surface of the material 2034. The surface of the material 2034 is not planar, but rather an irregular surface 2054 as shown. The irregular surface 2054 increases the surface area of the material and, hence, the area that comes in contact with the conducting fluid.

In one aspect, at the surface of the material 2034, there is chemical reaction between the material 2034 and the surrounding conducting fluid such that mass is released into the conducting fluid. The term "mass" as used herein refers to protons and neutrons that form a substance. One example includes the instant where the material is CuCl and when in contact with the conducting fluid, CuCl becomes Cu (solid) and Cl.sup.-in solution. The flow of ions into the conduction fluid is depicted by the ion paths 2050. In a similar manner, there is a chemical reaction between the material 2036 and the surrounding conducting fluid and ions are captured by the material 2036. The release of ions at the material 2034 and capture of ion by the material 2036 is collectively referred to as the ionic exchange. The rate of ionic exchange and, hence the ionic emission rate or flow, is controlled by the control device 2038. The control device 2038 can increase or decrease the rate of ion flow by altering the conductance, which alters the impedance, between the materials 2034 and 2036. Through controlling the ion exchange, the system 2030 can encode information in the ionic exchange process. Thus, the system 2030 uses ionic emission to encode information in the ionic exchange.

The control device 2038 can vary the duration of a fixed ionic exchange rate or current flow magnitude while keeping the rate or magnitude near constant, similar to when the frequency is modulated and the amplitude is constant. Also, the control device 2038 can vary the level of the ionic exchange rate or the magnitude of the current flow while keeping the duration near constant. Thus, using various combinations of changes in duration and altering the rate or magnitude, the control device 2038 encodes information in the current flow or the ionic exchange. For example, the control device 2038 may use, but is not limited to any of the following techniques namely, Binary Phase-Shift Keying (PSK), Frequency modulation, Amplitude modulation, on-off keying, and PSK with on-off keying.

As indicated above, the various aspects disclosed herein, such as systems 2030 and 2040 of FIGS. 9 and 10, respectively, include electronic components as part of the control device 2038 or the control device 2048. Components that may be present include but are not limited to: logic and/or memory elements, an integrated circuit, an inductor, a resistor, and sensors for measuring various parameters. Each component may be secured to the framework and/or to another component. The components on the surface of the support may be laid out in any convenient configuration. Where two or more components are present on the surface of the solid support, interconnects may be provided.

As indicated above, the system, such as system 2030 and 2040, control the conductance between the dissimilar materials and, hence, the rate of ionic exchange or the current flow. Through altering the conductance in a specific manner the system is capable of encoding information in the ionic exchange and the current signature. The ionic exchange or the current signature is used to uniquely identify the specific system. Additionally, the systems 2030 and 2040 are capable of producing various different unique exchanges or signatures and, thus, provide additional information. For example, a second current signature based on a second conductance alteration pattern may be used to provide additional information, which information may be related to the physical environment. To further illustrate, a first current signature may be a very low current state that maintains an oscillator on the chip and a second current signature may be a current state at least a factor of ten higher than the current state associated with the first current signature.

Figure 12:
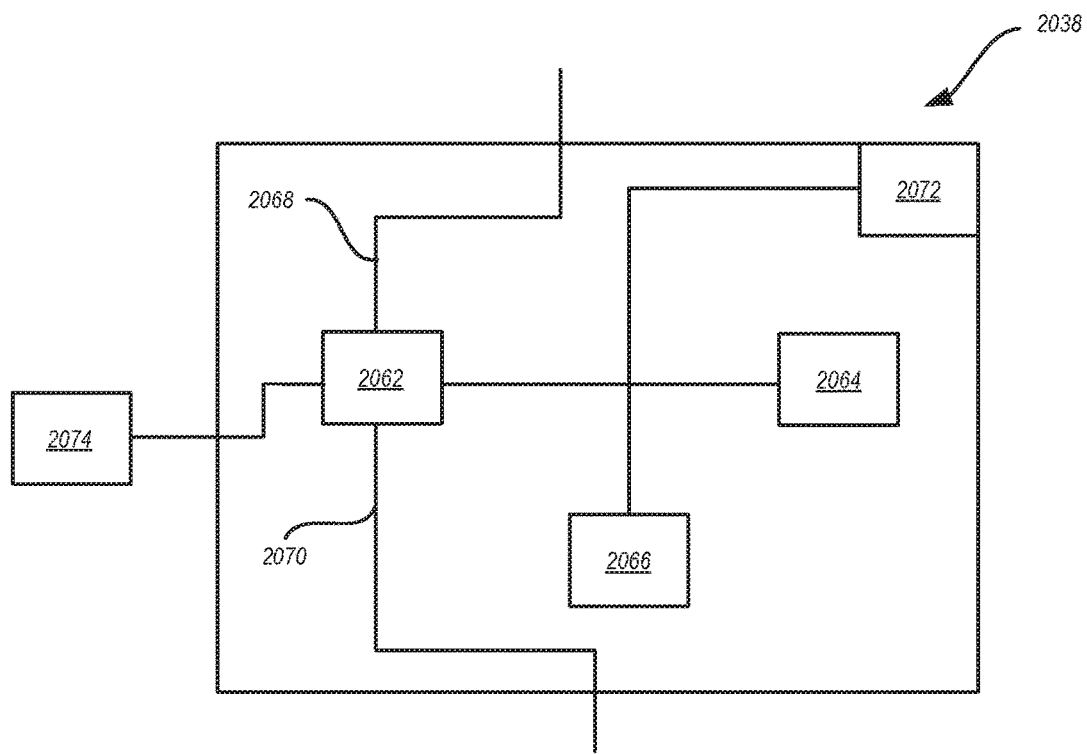
FIG. 12 is a block diagram illustration of one aspect of the control device used in the system of FIGS. 9 and 4**.

Referring now to FIG. 12, a block diagram representation of the control device 2038 is shown. The device 2030 includes a control module 2062, a counter or clock 2064, and a memory 2066. Additionally, the device 2038 is shown to include a sensor module 2072 as well as the sensor module 2074, which was referenced in FIG. 11. The control module 2062 has an input 2068 electrically coupled to the material 2034 and an output 2070 electrically coupled to the material 2036. The control module 2062, the clock 2064, the memory 2066, and the sensor modules 2072/2074 also have power inputs (some not shown). The power for each of these components is supplied by the voltage potential produced by the chemical reaction between materials 2034 and 2036 and the conducting fluid, when the system 2030 is in contact with the conducting fluid. The control module 2062 controls the conductance through logic that alters the overall impedance of the system 2030. The control module 2062 is electrically coupled to the clock 2064. The clock 2064 provides a clock cycle to the control module 2062. Based upon the programmed characteristics of the control module 2062, when a set number of clock cycles have passed, the control module 2062 alters the conductance characteristics between materials 2034 and 2036. This cycle is repeated and thereby the control device 2038 produces a unique current signature characteristic. The control module 2062 is also electrically coupled to the memory 2066. Both the clock 2064 and the memory 2066 are powered by the voltage potential created between the materials 2034 and 2036.

The control module 2062 is also electrically coupled to and in communication with the sensor modules 2072 and 2074. In the aspect shown, the sensor module 2072 is part of the control device 2038 and the sensor module 2074 is a separate component. In alternative aspects, either one of the sensor modules 2072 and 2074 can be used without the other and the scope of the present invention is not limited by the structural or functional location of the sensor modules 2072 or 2074. Additionally, any component of the system 2030 may be functionally or structurally moved, combined, or repositioned without limiting the scope of the present invention as claimed. Thus, it is possible to have one single structure, for example a processor, which is designed to perform the functions of all of the following modules: the control module 2062, the clock 2064, the memory 2066, and the sensor module 2072 or 2074. On the other hand, it is also within the scope of the present invention to have each of these functional components located in independent structures that are linked electrically and able to communicate.

Referring again to FIG. 12, the sensor modules 2072 or 2074 can include any of the following sensors: temperature, pressure, pH level, and conductivity. In one aspect, the sensor modules 2072 or 2074 gather information from the environment and communicate the analog information to the control module 2062. The control module then converts the analog information to digital information and the digital information is encoded in the current flow or the rate of the transfer of mass that produces the ionic flow. In another aspect, the sensor modules 2072 or 2074 gather information from the environment and convert the analog information to digital information and then communicate the digital information to control module 2062. In the aspect shown in FIG. 11, the sensor modules 2074 is shown as being electrically coupled to the material 2034 and 2036 as well as the control device 2038. In another aspect, as shown in FIG. 12, the sensor module 2074 is electrically coupled to the control device 2038 at connection 2078. The connection 2078 acts as both a source for power supply to the sensor module 2074 and a communication channel between the sensor module 2074 and the control device 2038.

Figure 11B:
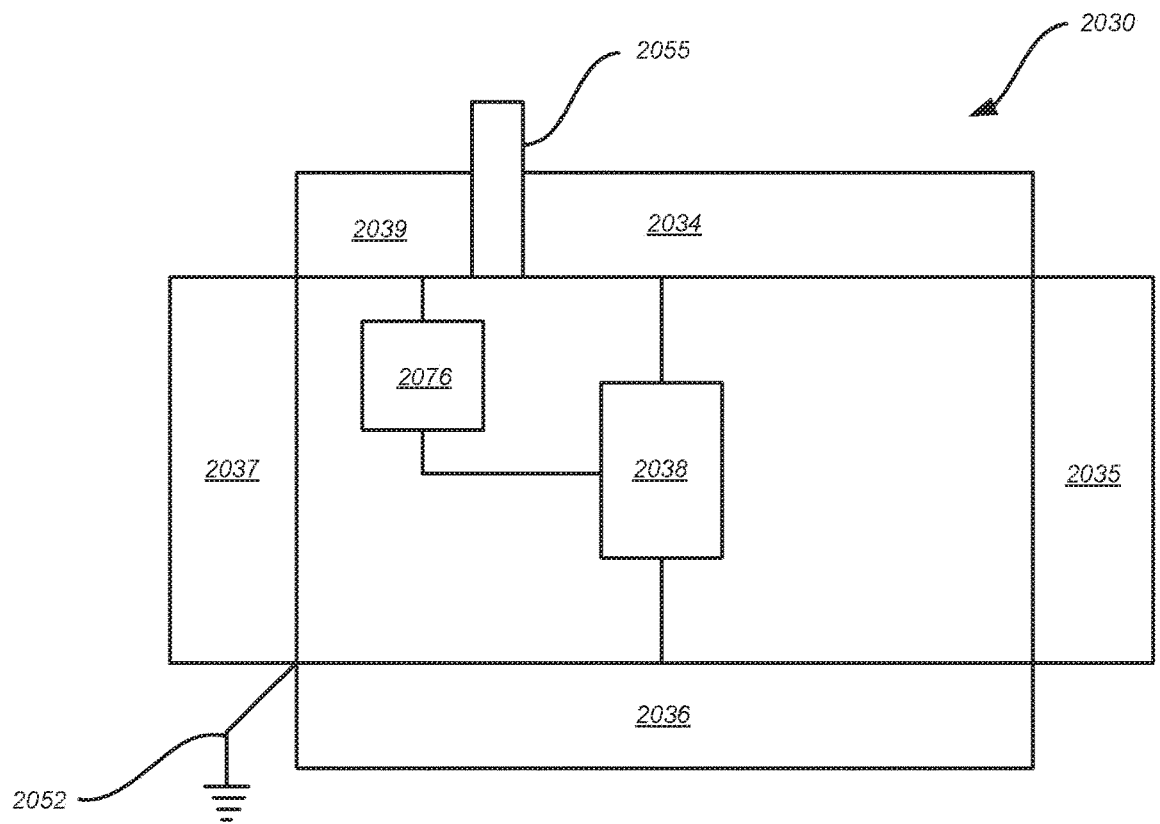
FIG. 11B shows the event indicator system of FIG. 11 with a pH sensor unit.

Referring now to FIG. 11B, the system 2030 includes a pH sensor module 2076 connected to a material 2039, which is selected in accordance with the specific type of sensing function being performed. The pH sensor module 2076 is also connected to the control device 2038. The material 2039 is electrically isolated from the material 2034 by a non-conductive barrier 2055. In one aspect, the material 2039 is platinum. In operation, the pH sensor module 2076 uses the voltage potential difference between the materials 2034/2036. The pH sensor module 2076 measures the voltage potential difference between the material 2034 and the material 2039 and records that value for later comparison. The pH sensor module 2076 also measures the voltage potential difference between the material 2039 and the material 2036 and records that value for later comparison. The pH sensor module 2076 calculates the pH level of the surrounding environment using the voltage potential values. The pH sensor module 2076 provides that information to the control device 2038. The control device 2038 varies the rate of the transfer of mass that produces the ionic transfer and the current flow to encode the information relevant to the pH level in the ionic transfer, which can be detected by a receiver (not shown). Thus, the system 2030 can determine and provide the information related to the pH level to a source external to the environment.

As indicated above, the control device 2038 can be programmed in advance to output a pre-defined current signature. In another aspect, the system can include a receiver system that can receive programming information when the system is activated. In another aspect, not shown, the switch 2064 and the memory 2066 can be combined into one device.

In addition to the above components, the system 2030 may also include one or other electronic components. Electrical components of interest include, but are not limited to: additional logic and/or memory elements, e.g., in the form of an integrated circuit; a power regulation device, e.g., battery, fuel cell or capacitor; a sensor, a stimulator, etc.; a signal transmission element, e.g., in the form of an antenna, electrode, coil, etc.; a passive element, e.g., an inductor, resistor, etc.

Figure 13:
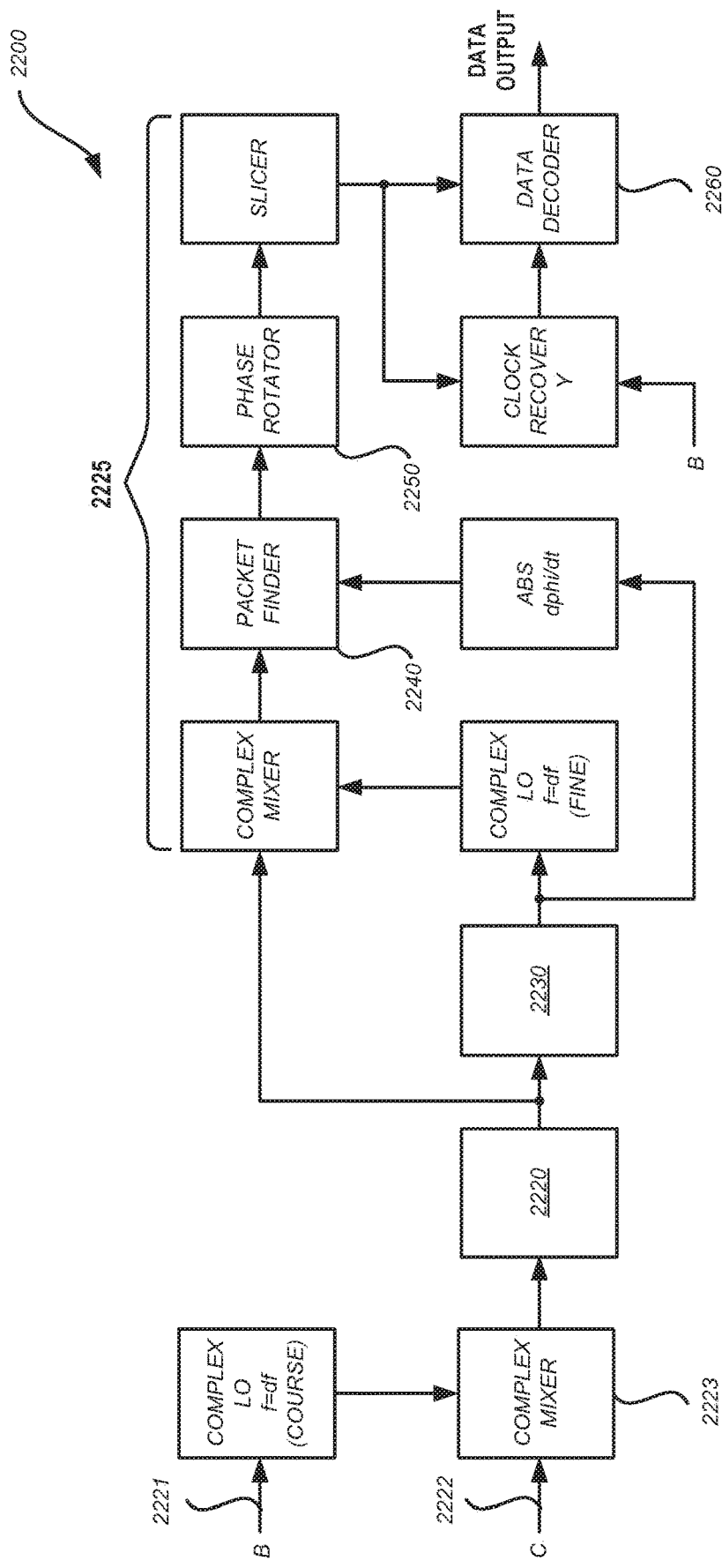
FIG. 13 is a functional block diagram of a demodulation circuit that performs coherent demodulation that may be present in a receiver, according to one aspect.

FIG. 13 provides a functional block diagram of how a receiver may implement a coherent demodulation protocol, according to one aspect of the invention. It should be noted that only a portion of the receiver is shown in FIG. 13. FIG. 13 illustrates the process of mixing the signal down to baseband once the carrier frequency (and carrier signal mixed down to carrier offset) is determined. A carrier signal 2221 is mixed with a second carrier signal 2222 at mixer 2223. A narrow low-pass filter 2220 is applied of appropriate bandwidth to reduce the effect of out-of-bound noise. Demodulation occurs at functional blocks 2225 in accordance with the coherent demodulation scheme of the present invention. The unwrapped phase 2230 of the complex signal is determined. An optional third mixer stage, in which the phase evolution is used to estimate the frequency differential between the calculated and real carrier frequency can be applied. The structure of the packet is then leveraged to determine the beginning of the coding region of the BPSK signal at block 2240. Mainly, the presence of the sync header, which appears as an FM porch in the amplitude signal of the complex demodulated signal is used to determine the starting bounds of the packet. Once the starting point of the packet is determined the signal is rotated at block 2250 on the IQ plane and standard bit identification and eventually decoded at block 2260.

In addition to demodulation, the transbody communication module may include a forward error correction module, which module provides additional gain to combat interference from other unwanted signals and noise. Forward error correction functional modules of interest include those described in PCT Application Serial No. PCT/US2007/024225; the disclosure of which is herein incorporated by reference. In some instances, the forward error correction module may employ any convenient protocol, such as Reed-Solomon, Golay, Hamming, BCH, and Turbo protocols to identify and correct (within bounds) decoding errors.

Receivers of the invention may further employ a beacon functionality module. In various aspects, the beacon switching module may employ one or more of the following: a beacon wakeup module, a beacon signal module, a wave/frequency module, a multiple frequency module, and a modulated signal module.

The beacon switching module may be associated with beacon communications, e.g., a beacon communication channel, a beacon protocol, etc. For the purpose of the present disclosure, beacons are typically signals sent either as part of a message or to augment a message (sometimes referred to herein as "beacon signals"). The beacons may have well-defined characteristics, such as frequency. Beacons may be detected readily in noisy environments and may be used for a trigger to a sniff circuit, such as described below. In one aspect, the beacon switching module may comprise the beacon wakeup module, having wakeup functionality. Wakeup functionality generally comprises the functionality to operate in high power modes only during specific times, e.g., short periods for specific purposes, to receive a signal, etc. An important consideration on a receiver portion of a system is that it be of low power. This feature may be advantageous in an implanted receiver, to provide for both small size and to preserve a long-functioning electrical supply from a battery. The beacon switching module enables these advantages by having the receiver operate in a high power mode for very limited periods of time. Short duty cycles of this kind can provide optimal system size and energy draw features.

In practice, the receiver may "wake up" periodically, and at low energy consumption, to perform a "sniff function" via, for example, a sniff circuit. For the purpose of the present application, the term "sniff function" generally refers to a short, low-power function to determine if a transmitter is present. If a transmitter signal is detected by the sniff function, the device may transition to a higher power communication decode mode. If a transmitter signal is not present, the receiver may return, e.g., immediately return, to sleep mode. In this manner, energy is conserved during relatively long periods when a transmitter signal is not present, while high-power capabilities remain available for efficient decode mode operations during the relatively few periods when a transmit signal is present. Several modes, and combination thereof, may be available for operating the sniff circuit. By matching the needs of a particular system to the sniff circuit configuration, an optimized system may be achieved.

Figure 14:
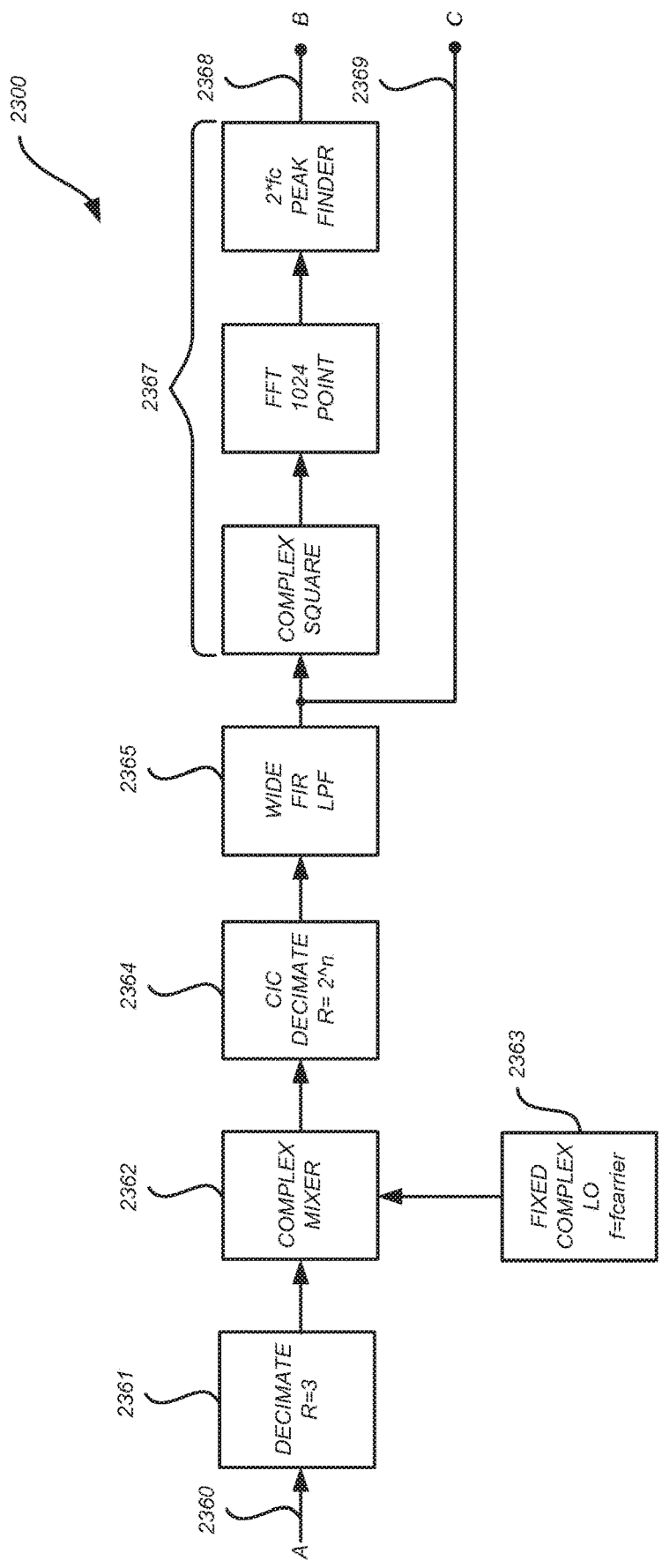
FIG. 14 illustrates a functional block diagram for a beacon module within a receiver, according to one aspect.

Another view of a beacon module is provided in the functional block diagram shown in FIG. 14. The scheme outlined in FIG. 14 outlines one technique for identifying a valid beacon. The incoming signal 2360 represents the signals received by electrodes, bandpass filtered (such as from 10 KHz to 34 KHz) by a high frequency signaling chain (which encompasses the carrier frequency), and converted from analog to digital. The signal 2360 is then decimated at block 2361 and mixed at the nominal drive frequency (such as, 12.5 KHz, 20 KHz, etc.) at mixer 2362. The resulting signal is decimated at block 2364 and low-pass filtered (such as 5 KHz BW) at block 2365 to produce the carrier signal mixed down to carrier offset—signal 2369. Signal 2369 is further processed by blocks 2367 (fast Fourier transform and then detection of two strongest peaks) to provide the true carrier frequency signal 2368. This protocol allows for accurate determination of the carrier frequency of the transmitted beacon.

Figure 15:
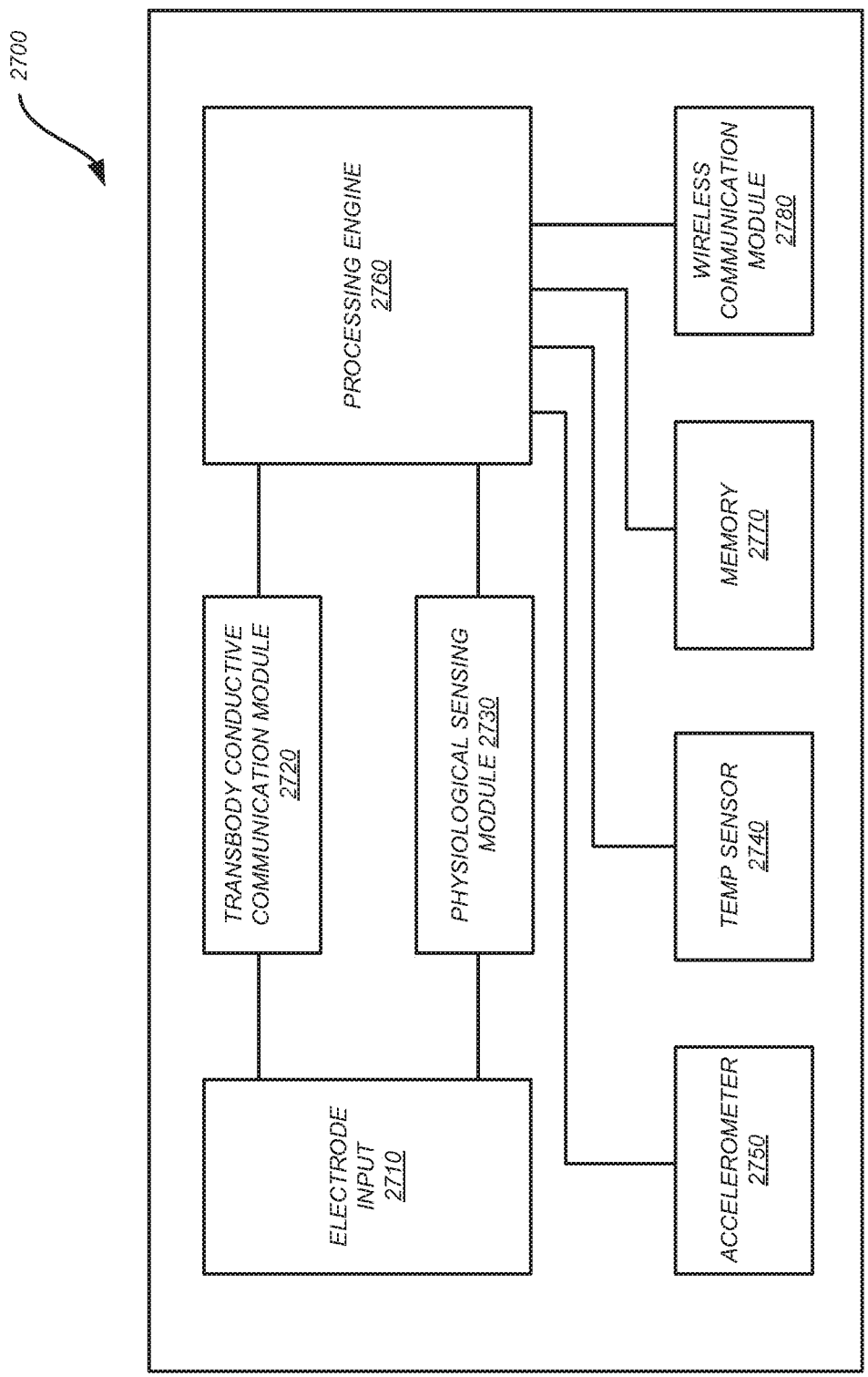
FIG. 15 is a block diagram of the different functional modules that may be present in a receiver, according to one aspect.

FIG. 15 provides a block functional diagram of an integrated circuit component of a signal receiver according to an aspect of the invention. In FIG. 15, receiver 2700 includes electrode input 2710. Electrically coupled to the electrode input 2710 are transbody conductive communication module 2720 and physiological sensing module 2730. In one aspect, transbody conductive communication module 2720 is implemented as a high frequency (HF) signal chain and physiological sensing module 2730 is implemented as a low frequency (LF) signal chain. Also shown are CMOS temperature sensing module 2740 (for detecting ambient temperature) and a 3-axis accelerometer 2750. Receiver 2700 also includes a processing engine 2760 (for example, a microcontroller and digital signal processor), non-volatile memory 2770 (for data storage) and wireless communication module 2780 (for data transmission to another device, for example in a data upload action).

Figure 16:
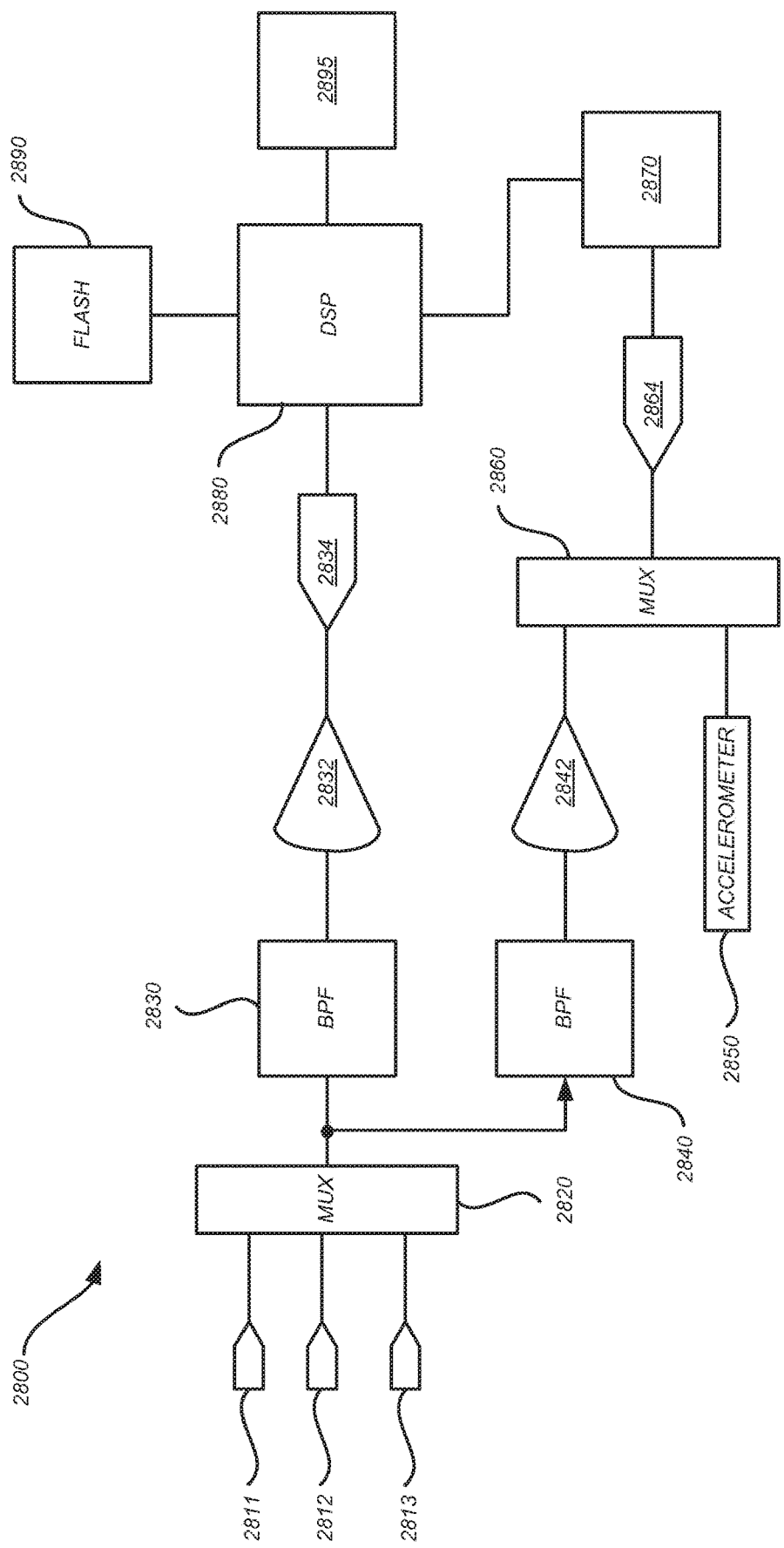
FIG. 16 is a block diagram of a receiver, according to one aspect.

FIG. 16 provides a more detailed block diagram of a circuit configured to implement the block functional diagram of the receiver depicted in FIG. 15, according to one aspect of the invention. In FIG. 16, receiver 800 includes electrodes e1, e2 and e3 (2811, 2812 and 2813) which, for example, receive the conductively transmitted signals by an IEM and/or sense physiological parameters or biomarkers of interest. The signals received by the electrodes 2811, 2812, and 2813 are multiplexed by multiplexer 820 which is electrically coupled to the electrodes.

Multiplexer 2820 is electrically coupled to both high band pass filter 2830 and low band pass filter 2840. The high and low frequency signal chains provide for programmable gain to cover the desired level or range. In this specific aspect, high band pass filter 2830 passes frequencies in the 10 KHz to 34 KHz band while filtering out noise from out-of-band frequencies. This high frequency band may vary, and may include, for example, a range of 3 KHz to 300 KHz. The passing frequencies are then amplified by amplifier 2832 before being converted into a digital signal by converter 2834 for input into high power processor 2880 (shown as a DSP) which is electrically coupled to the high frequency signal chain.

Low band pass filter 2840 is shown passing lower frequencies in the range of 0.5 Hz to 150 Hz while filtering out out-of-band frequencies. The frequency band may vary, and may include, for example, frequencies less than 300 Hz, such as less than 200 Hz, including less than 150 Hz. The passing frequency signals are amplified by amplifier 842. Also shown is accelerometer 850 electrically coupled to second multiplexer 2860. Multiplexer 2860 multiplexes the signals from the accelerometer with the amplified signals from amplifier 2842. The multiplexed signals are then converted to digital signals by converter 864 which is also electrically coupled to low power processor 2870.

In one aspect, a digital accelerometer (such as one manufactured by Analog Devices), may be implemented in place of accelerometer 2850. Various advantages may be achieved by using a digital accelerometer. For example, because the signals the digital accelerometer would produce signals already in digital format, the digital accelerometer could bypass converter 2864 and electrically couple to the low power microcontroller 2870—in which case multiplexer 2860 would no longer be required. Also, the digital signal may be configured to turn itself on when detecting motion, further conserving power. In addition, continuous step counting may be implemented. The digital accelerometer may include a FIFO buffer to help control the flow of data sent to the low power processor 2870. For instance, data may be buffered in the FIFO until full, at which time the processor may be triggered to turn awaken from an idle state and receive the data.

Low power processor 2870 may be, for example, an MSP430 microcontroller from Texas Instruments. Low power processor 2870 of receiver 2800 maintains the idle state, which as stated earlier, requires minimal current draw—e.g., 10 µA or less, or 1 µA or less.

High power processor 2880 may be, for example, a VC5509 digital signal process from Texas Instruments. The high power processor 2880 performs the signal processing actions during the active state. These actions, as stated earlier, require larger amounts of current than the idle state—e.g., currents of 30 µA or more, such as 50 µA or more—and may include, for example, actions such as scanning for conductively transmitted signals, processing conductively transmitted signals when received, obtaining and/or processing physiological data, etc.

The receiver may include a hardware accelerator module to process data signals. The hardware accelerator module may be implemented instead of, for example, a DSP. Being a more specialized computation unit, it performs aspects of the signal processing algorithm with fewer transistors (less cost and power) compared to the more general purpose DSP. The blocks of hardware may be used to "accelerate" the performance of important specific function(s). Some architectures for hardware accelerators may be "programmable" via microcode or VLIW assembly. In the course of use, their functions may be accessed by calls to function libraries.

The hardware accelerator (HWA) module comprises an HWA input block to receive an input signal that is to be processed and instructions for processing the input signal; and, an HWA processing block to process the input signal according to the received instructions and to generate a resulting output signal. The resulting output signal may be transmitted as needed by an HWA output block.

Also shown in FIG. 16 is flash memory 2890 electrically coupled to high power processor 2880. In one aspect, flash memory 2890 may be electrically coupled to low power processor 2870, which may provide for better power efficiency.

Wireless communication element 2895 is shown electrically coupled to high power processor 2880 and may include, for example, a BLUETOOTH™ wireless communication transceiver. In one aspect, wireless communication element 2895 is electrically coupled to high power processor 2880. In another aspect, wireless communication element 2895 is electrically coupled to high power processor 2880 and low power processor 2870. Furthermore, wireless communication element 2895 may be implemented to have its own power supply so that it may be turned on and off independently from other components of the receiver—e.g., by a microprocessor.

FIG. 17 provides a view of a block diagram of hardware in a receiver according to an aspect of the invention related to the high frequency signal chain. In FIG. 17, receiver 2900 includes receiver probes (for example in the form of electrodes 2911, 2912 and 2913) electrically coupled to multiplexer 2920. Also shown are high pass filter 2930 and low pass filter 2940 to provide for a band pass filter which eliminates any out-of-band frequencies. In the aspect shown, a band pass of 10 KHz to 34 KHz is provided to pass carrier signals falling within the frequency band. Example carrier frequencies may include, but are not limited to, 12.5 KHz and 20 KHz. One or more carriers may be present. In addition, receiver 2900 includes analog to digital converter 2950—for example, sampling at 500 KHz. The digital signal can thereafter be processed by the DSP. Shown in this aspect is DMA to DSP unit 960 which sends the digital signal to dedicated memory for the DSP. The direct memory access provides the benefit of allowing the rest of the DSP to remain in a low power mode.

Example Configurations for Various States

As stated earlier, for each receiver state, the high power functional block may be cycled between active and inactive states accordingly. Also, for each receiver state, various receiver elements (such as circuit blocks, power domains within processor, etc.) of a receiver may be configured to independently cycle from on and off by the power supply module. Therefore, the receiver may have different configurations for each state to achieve power efficiency.

In certain aspects, the receivers are part of a body-associated system or network of devices, such as sensors, signal receivers, and optionally other devices, which may be internal and/or external, which provide a variety of different types of information that is ultimately collected and processed by a processor, such as an external processor, which then can provide contextual data about a living subject, such as a patient, as output. For example, the receiver may be a member of an in-body network of devices which can provide an output that includes data about IEM ingestion, one or more physiological sensed parameters, implantable device operation, etc., to an external collector of the data. The external collector, e.g., in the form of a health care network server, etc., of the data then combines this receiver provided data with additional relevant data about the patient, e.g., weight, weather, medical record data, etc., and may process this disparate data to provide highly specific and contextual patient specific data.

Systems of the invention include, in certain aspects, a signal receiver aspect of a receiver and one or more IEMs. IEMs of interest include those described in PCT application serial no. PCT/US2006/016370 published as WO/2006/116718; PCT application serial no. PCT/US2007/082563 published as WO/2008/052136; PCT application serial no. PCT/US2007/024225 published as WO/2008/063626; PCT application serial no. PCT/US2007/022257 published as WO/2008/066617; PCT application serial no. PCT/US2008/052845 published as WO/2008/095183; PCT application serial no. PCT/US2008/053999 published as WO/2008/101107; PCT application serial no. PCT/US2008/056296 published as WO/2008/112577; PCT application serial no. PCT/US2008/056299 published as WO/2008/112578; and PCT application serial no. PCT/US2008/077753 published as WO 2009/042812; the disclosures of which applications are herein incorporated by reference.

In certain aspects the systems include an external device which is distinct from the receiver (which may be implanted or topically applied in certain aspects), where this external device provides a number of functionalities. Such an external device can include the capacity to provide feedback and appropriate clinical regulation to the patient. Such a device can take any of a number of forms. For example, the device can be configured to sit on the bed next to the patient, e.g., a bedside monitor. Other formats include, but are not limited to, PDAs, smart phones, home computers, etc.

An example of a system of the invention is shown in FIG. 18A. In FIG. 18A, system 1500 includes a pharmaceutical composition 1510 that comprises an IEM. Also present in system 1500 is signal receiver 1520, such as the signal receiver illustrated in FIGS. 10 to 12. Signal receiver 1520 is configured to detect a signal emitted from the identifier of the IEM 1510. Signal receiver 1520 also includes physiologic sensing capability, such as ECG and movement sensing capability. Signal receiver 1520 is configured to transmit data to a patient's an external device or PDA 1530 (such as a smart phone or other wireless communication enabled device), which in turn transmits the data to a server 1540. Server 1540 may be configured as desired, e.g., to provide for patient directed permissions. For example, server 1540 may be configured to allow a family caregiver 1550 to participate in the patient's therapeutic regimen, e.g., via an interface (such as a web interface) that allows the family caregiver 1550 to monitor alerts and trends generated by the server 1540, and provide support back to the patient, as indicated by arrow 1560. The server 1540 may also be configured to provide responses directly to the patient, e.g., in the form of patient alerts, patient incentives, etc., as indicated by arrow 1565 which are relayed to the patient via PDA 1530. Server 1540 may also interact with a health care professional (e.g., RN, physician) 1555, which can use data processing algorithms to obtain measures of patient health and compliance, e.g., wellness index summaries, alerts, cross-patient benchmarks, etc., and provide informed clinical communication and support back to the patient, as indicated by arrow 1580.

Another example of the system of the present invention is shown in FIG. 18B. FIG. 18B depicts a system that includes a syringe 15107, a receiver 15105, a glucometer 15110, a wireless communication unit 15115, communication links 15150B-E, and a dosage manager 15160. The system generally provides intelligent mechanisms for controlling the delivery of a dosage by the syringe 15107 (e.g., subcutaneous needle insertion or luer connection with an Intra Venous access device). This control may include, for example, detecting that the syringe 15107 is proximate to the patient, measuring the amount of the dose administered by the syringe 15107, communicating the measurement information to other devices, such as the receiver 15105, the glucometer 15110, the wireless devices 15115, and/or the dosage manager 15160, and providing feedback information to one or more of those devices. In some implementations, the feedback information may prevent the administration of the dosage to the patient using, for example, an interlock at the syringe 15107 to prevent giving the dosage. The syringe 15107 may, based on the feedback, output a visual indication (e.g., a light emitting diode (LED)) or an aural signal to indicate that the dosage is not to be administered to the patient. For example, the interlock mechanism, LED, and/or sound at the syringe 15107 may signal that the patient is receiving the wrong type of medication, receiving the dosage at the wrong time, and/or receiving the wrong amount of medication.

In some implementations, the syringe 15107 may be configured in an interlock mode as a default state to prevent the administration of a dosage until the dosage manager 15160 provides feedback information to unlock the syringe 15107 to allow the administration of the agent or medication.

Moreover, the syringe 15107 may, in some embodiments, include a measurement mechanism to provide measurement information representative of the amount of the dosage. When that is the case, the measurement information may be used by the dosage manager 160 along with other patient information, such as blood pressure, glucose level, heart rate, ingestible event marker (IEM) data, etc., to control when, and/or how much of, a dosage is provided to the patient. Furthermore, the syringe 15107 may activate the measurement mechanism (which provides the measured information) when the syringe 15107 is proximate to (e.g., enters or is close to) the patient's body, at which time the measurement information and other information, such as an identifier associated with the syringe 15107, a patient identifier, etc, are carried by a signal to other devices, such as the receiver 15105, the glucometer 15110, and/or the wireless device 15115, for communication to the dosage manager 15160. Moreover, these other devices may monitor the time when the dosage is administered by the syringe 15107. As such, the dosage manager 15160 may receive a precise time when the dosage is administered rather than rely on user-provided dosage administration times. As such, the system may be used to evaluate a specific fluid transfer event between a parenteral fluid delivery device, such as syringe 15107, and a patient While various details have been set forth in the foregoing description, it will be appreciated that the various aspects of the personal authentication apparatus, system, and method may be practiced without these specific details. For example, for conciseness and clarity selected aspects have been shown in block diagram form rather than in detail. Some portions of the detailed descriptions provided herein may be presented in terms of instructions that operate on data that is stored in a computer memory. Such descriptions and representations are used by those skilled in the art to describe and convey the substance of their work to others skilled in the art. In general, an algorithm refers to a self-consistent sequence of steps leading to a desired result, where a "step" refers to a manipulation of physical quantities which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities.

Unless specifically stated otherwise as apparent from the foregoing discussion, it is appreciated that, throughout the foregoing description, discussions using terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

It is worthy to note that any reference to "one aspect," "an aspect," "one embodiment," or "an embodiment" means that a particular feature, structure, or characteristic described in connection with the aspect is included in at least one aspect. Thus, appearances of the phrases "in one aspect," "in an aspect," "in one embodiment," or "in an embodiment" in various places throughout the specification are not necessarily all referring to the same aspect. Furthermore, the particular features, structures or characteristics may be combined in any suitable manner in one or more aspects.

Some aspects may be described in accordance with the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other.

It is worthy to note that any reference to "one aspect," "an aspect," "one embodiment," or "an embodiment" means that a particular feature, structure, or characteristic described in connection with the aspect is included in at least one aspect. Thus, appearances of the phrases "in one aspect," "in an aspect," "in one embodiment," or "in an embodiment" in various places throughout the specification are not necessarily all referring to the same aspect. Furthermore, the particular features, structures or characteristics may be combined in any suitable manner in one or more aspects.

Although various embodiments have been described herein, many modifications, variations, substitutions, changes, and equivalents to those embodiments may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed embodiments. The following claims are intended to cover all such modification and variations.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

All of the above-mentioned U.S. patents, U.S. patent application publications, U.S. patent applications, foreign patents, foreign patent applications, non-patent publications referred to in this specification and/or listed in any Application Data Sheet, or any other disclosure material are incorporated herein by reference, to the extent not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory. Further, implementation of at least part of a system for performing a method in one territory does not preclude use of the system in another territory.

Although various embodiments have been described herein, many modifications, variations, substitutions, changes, and equivalents to those embodiments may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed embodiments. The following claims are intended to cover all such modification and variations.

In summary, numerous benefits have been described which result from employing the concepts described herein. The foregoing description of the one or more embodiments has been presented for purposes of illustration and description. It is not intended to be exhaustive or limiting to the precise form disclosed. Modifications or variations are possible in light of the above teachings. The one or more embodiments were chosen and described in order to illustrate principles and practical application to thereby enable one of ordinary skill in the art to utilize the various embodiments and with various modifications as are suited to the particular use contemplated. It is intended that the claims submitted herewith define the overall scope.

The invention claimed is:

1. An apparatus, comprising:
a physiological sensing module for receiving an electrical signal from a body associated device,
the electrical signal including a profile of biometric signals including heart rate, body temperature, and circadian rhythm detected by at least one electrode coupled to a body of a user;
the body-associated device placed in electrical contact with the body of a user of a target authentication device, wherein the body-authentication device is configured with a non-physiological secret code;
wherein the electric signal comprises the profile of biometric signals hashed by the body associated device with the non-physiological secret code to yield a signature;
an authentication receiver module coupled to the at least one electrode, the authentication receiver module configured to receive the electrical signal from the at least one electrode and to authenticate an identity of the user when the received electrical signal matches a predetermined criterion;
wherein the predetermined criterion includes a baseline biometric signature stored in a database comprising a running average of previously detected biometric signals including heart rate, body temperature, and circadian rhythm received by the physiological sensing module as a running series of signatures generated by the body associated device, each signature in the running series including a different profile of biometric signals including heart rate, body temperature, and circadian rhythm to be used to calculate the running average.

2. The apparatus of claim 1, further comprising a trans-body conductive communication module to receive a trans-body conductive signal representing the authentication code for the target authentication device.

3. The apparatus of claim 1, further comprising a decoder to decode the detected electrical signal.

4. The apparatus of claim 3, further comprising a compare module to compare the decoded detected electrical signal with established criteria.

5. The apparatus of claim 1, wherein the body-associated device is implanted in the body of the user.

6. The apparatus of claim 1, wherein the body-associated device is adhesively attached to the user's skin.

7. The apparatus of claim 1, wherein the body-associated device is embedded in an object in physical contact with the user's skin.

8. The apparatus of claim 1, wherein the body-associated device comprises a transmission device that is configured with the authentication code.

9. The apparatus of claim 1, wherein the body-associated device transmits an electrical signal at regular time intervals.

10. The apparatus of claim 1, wherein the body-associated device comprises an input device, wherein the input device triggers the body-associated device to transmit the electrical signal.

11. The apparatus of claim 1, wherein the body-associated device transmits an electrical signal when an event marker system is activated.

12. The apparatus of claim 1, wherein the body-associated device is configured to transmit the authentication code a predetermined number of times, and wherein the body-associated device is configured to be de-authorized and to stop transmitting the authentication code after it has transmitted the authentication code the predetermined number of times.

13. A system, comprising:
a physiological sensing module for receiving an electrical signal from a body associated device,
the electrical signal including a profile of biometric signals including heart rate, body temperature, and circadian rhythm detected by at least one electrode coupled to a body of a user;
the body-associated device placed in electrical contact with the body of a user of a target authentication device, wherein the body-associated device is configured with a non-physiological secret code;
wherein the electric signal comprises the profile of biometric signals hashed by the body associated device with the non-physiological secret code to yield a signature;
an authentication receiver module coupled to the at least one electrode, the authentication receiver module configured to receive the electrical signal from the at least one electrode and to authenticate an identity of the user when the received electrical signal matches a predetermined criterion;
wherein the predetermined criterion includes a baseline biometric signature stored in a database comprising a running average of previously detected biometric signals including heart rate, body temperature, and circadian rhythm received by the physiological sensing module as a running series of signatures generated by the body associated device, each signature in the running series including a different profile of biometric signals including heart rate, body temperature, and circadian rhythm to be used to calculate the running average;
and
a compare module, wherein the authorization receiver module is configured to encode the detected electrical signal with a second secret code and to transmit the encoded signal to the compare module where it is compared to an expected result dependent on mathematical properties of the encoding and the second secret code.

14. A method, comprising: placing a body associated device in electrical contact with a user's body; using the body-associated device to generate an electrical signal associated with a user of the target authentication device, the electric signal representing an authentication code for the target authentication device and including a profile of biometric signals including heartrate, body temperature, and circadian rhythm detected by at least one electrode coupled to the body of the user, and wherein the electrical signal comprises the profile of biometric signals hashed by the body-associated device with the non-physiological secret code to yield a signature; detecting the electrical signal by at least one electrode; receiving by an authentication receiver module coupled to the at least one electrode, the electrical signal froM the at least one electrode; and authenticating an identity of the user when the received electrical signal matches a predetermined criterion, wherein the predetermined criterion includes a baseline biometric signature stored in a database comprising a running average of previously detected biometric signals including heart rate body temperature, and circadian rhythm received by physiological sensing as a running series of signatures generated by the body associated device, each signature in the running series including a different profile of biometric signals including heart rate, body temperature, and circadian rhythm to be used to calculate the running average.

15. The method of claim 14, wherein the step of using the body-associated device to generate an electrical signal associated with a user of the target authentication device is repeated at regular time intervals.

16. The method of claim 14, wherein the step of using the body-associated device to generate an electrical signal associated with a user of the target authentication device is performed after a user triggers it by using an input device associated with the body-associated device.

17. The method of claim 14, wherein the step of using the body-associated device to generate an electrical signal associated with a user of the target authentication device can only be repeated a predetermined number of times, and wherein the body-associated device is deactivated after the predetermined number of times is reached.

* * * * *